US011433126B2

(12) United States Patent
Lowry et al.

(10) Patent No.: US 11,433,126 B2
(45) Date of Patent: Sep. 6, 2022

(54) PROTECTION FROM STRESS, ANXIETY, NEUROINFLAMMATION, AND COGNITIVE DYSFUNCTION

(71) Applicant: The Regents of the University of Colorado, a body corporate, Denver, CO (US)

(72) Inventors: Christopher A. Lowry, Boulder, CO (US); Matthew G. Frank, Lousville, CO (US); Laura Fonken, Austin, TX (US); Steven F. Maier, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 25 days.

(21) Appl. No.: 17/125,422

(22) Filed: Dec. 17, 2020

(65) Prior Publication Data
US 2021/0275659 A1 Sep. 9, 2021

Related U.S. Application Data

(63) Continuation-in-part of application No. PCT/US2019/038014, filed on Jun. 19, 2019.

(60) Provisional application No. 62/687,093, filed on Jun. 19, 2018, provisional application No. 62/703,574, filed on Jul. 26, 2018.

(51) Int. Cl.
| | |
|---|---|
| A61K 39/04 | (2006.01) |
| A61K 35/741 | (2015.01) |
| C07K 14/35 | (2006.01) |
| A61K 39/00 | (2006.01) |

(52) U.S. Cl.
CPC ............ *A61K 39/04* (2013.01); *A61K 35/741* (2013.01); *C07K 14/35* (2013.01); *A61K 2039/521* (2013.01); *A61K 2039/542* (2013.01)

(58) Field of Classification Search
None
See application file for complete search history.

(56) References Cited

U.S. PATENT DOCUMENTS

2009/0318676 A1  12/2009  Manoharan et al.

FOREIGN PATENT DOCUMENTS

WO  2017037141 A1  3/2017

OTHER PUBLICATIONS

Fonken LK et al. *Mycobacterium vaccae* immunization protects aged rats from surgery-elicited neuroinflammation and cognitive dysfunction. In: PsychoNeuroImmunology Research Society's 25th Annual Scientific Meeting, Jun. 6, 2018-Jun. 9, 2018, #3175, Miami Beach, Florida, United States.*
Smith et al. Psychopharmacology (Berl) 236: 1653-1670, pp. 1-4, May 2019.*
Stanford et al. Immunobiology 191: 555-563, 1994, Abstract.*
Alawneh, AG. "Synthesis and Biochemical Evaluation of Aminoboranephosphonate Phosphoramidimidate and Phosphoramidate DNA"; Jan. 1, 2018, pp. 1-208 [online], [retrieved on Aug. 29, 2019). Retrieved from the Internet <URL: https ://pdfs. semanticscholar. org/3 7 0a/50a6 73e08fbc5063034b 15b242f 56144fd43. pdf>; p. 11, second paragraph; p. 60, figure 4.2; p. 60, figure 4.3; p. 85, figure 5.3; p. 85, first paragraph; p. 86, figure 5.4; p. 112, first paragraph, 70 pages.
International Search Report dated Oct. 16, 2019 in International Application No. PCT/US19/37346, 2 pages.

* cited by examiner

*Primary Examiner* — Sarvamangala Devi
(74) *Attorney, Agent, or Firm* — Berg Hill Greenleaf Ruscitti LLP

(57) ABSTRACT

Methods of treating or preventing stress, anxiety, or post-operative cognitive dysfunction. Also provided are methods of improving resilience in a subject by administering a therapeutically effective amount of isolated *Mycobacterium*.

14 Claims, 34 Drawing Sheets

Specification includes a Sequence Listing.

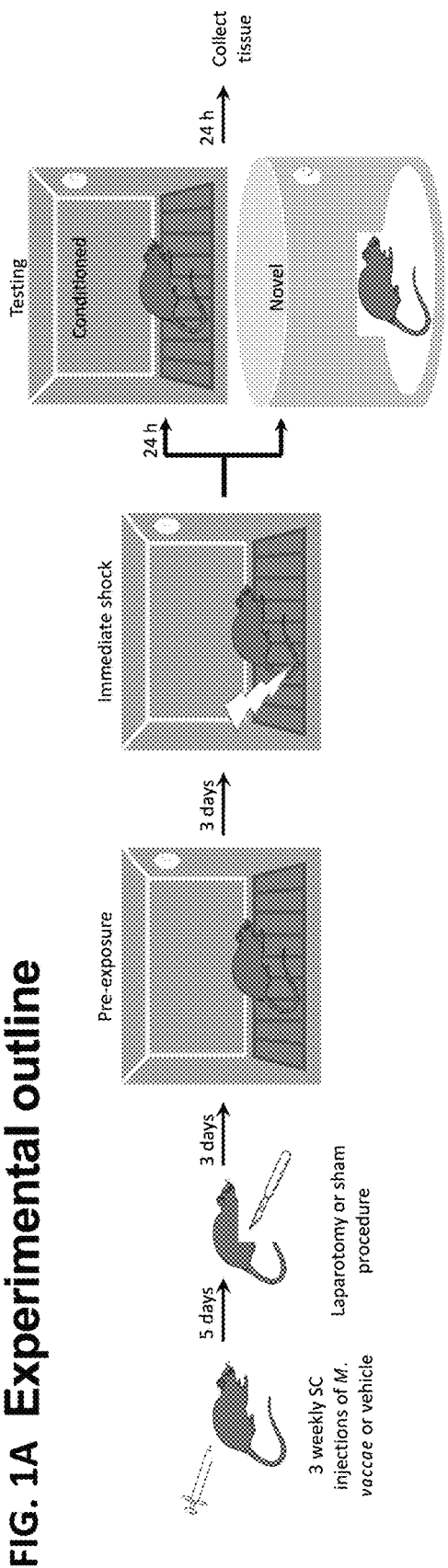
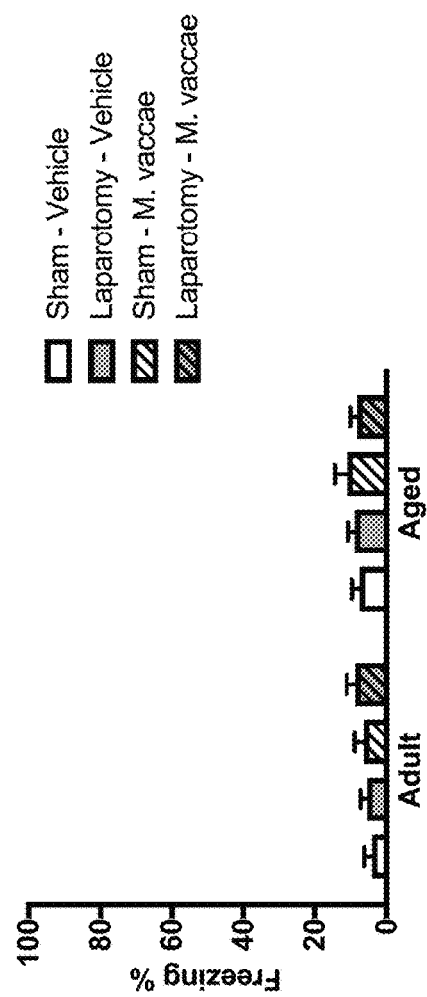
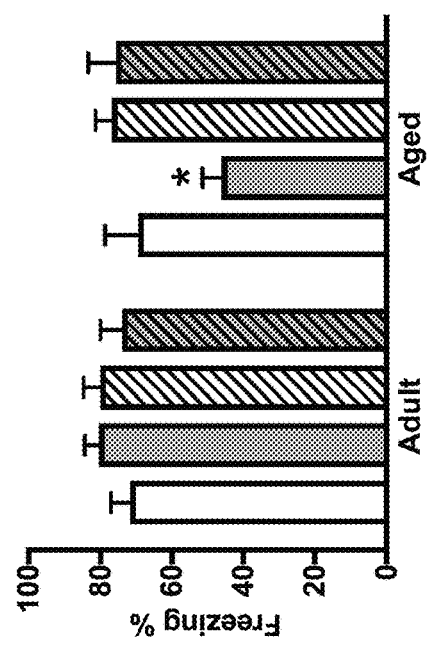
FIG. 1A Experimental outline
FIG. 1B Conditioned context
FIG. 1C Novel context

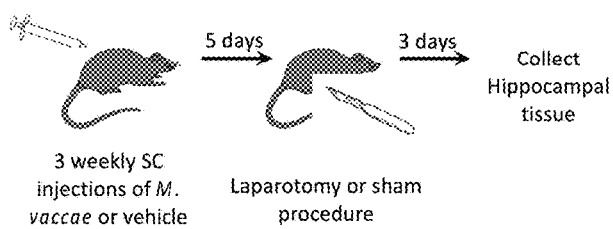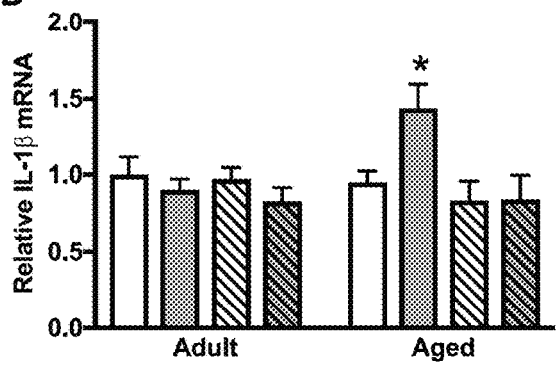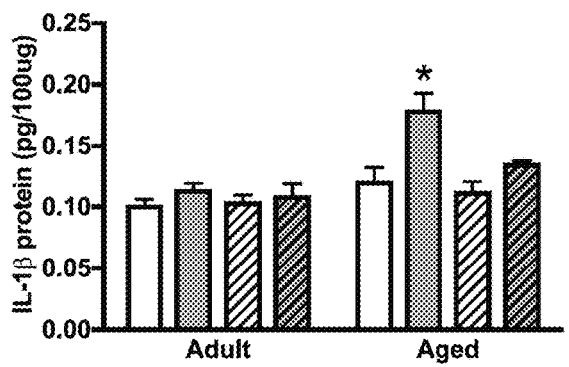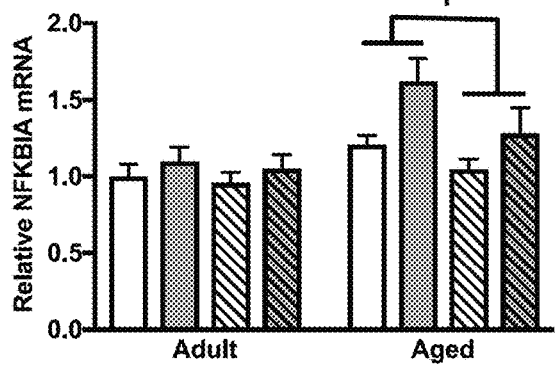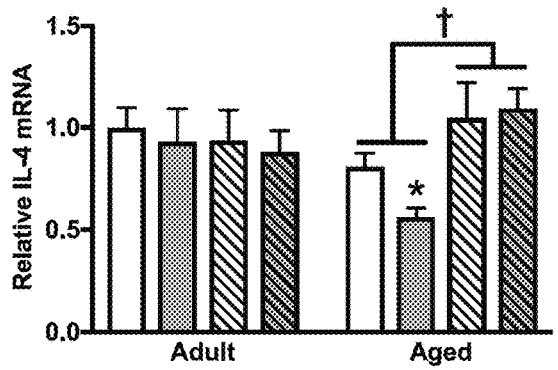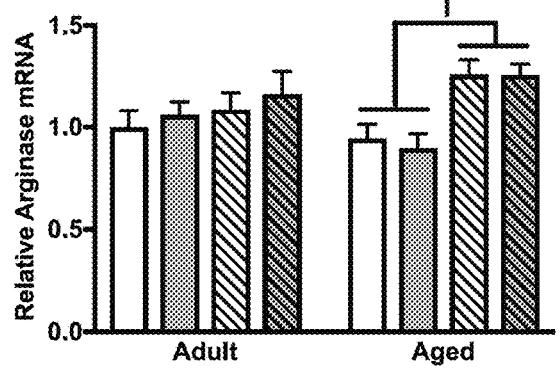

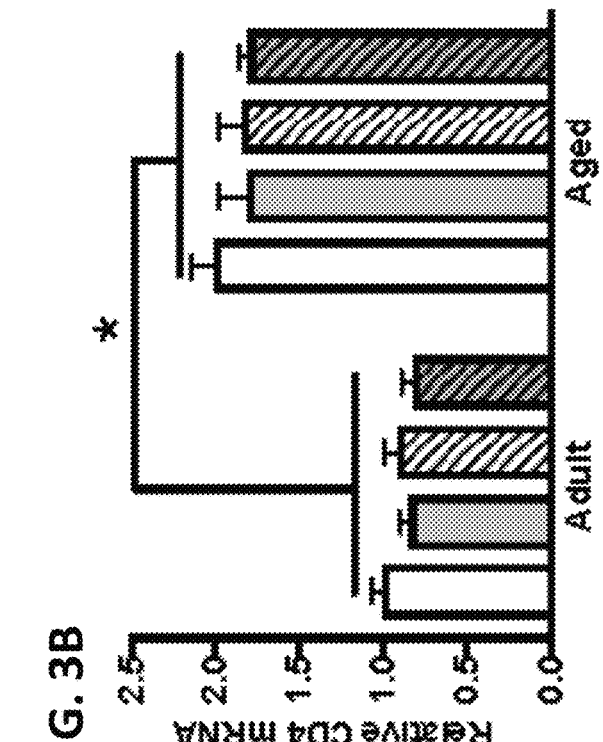
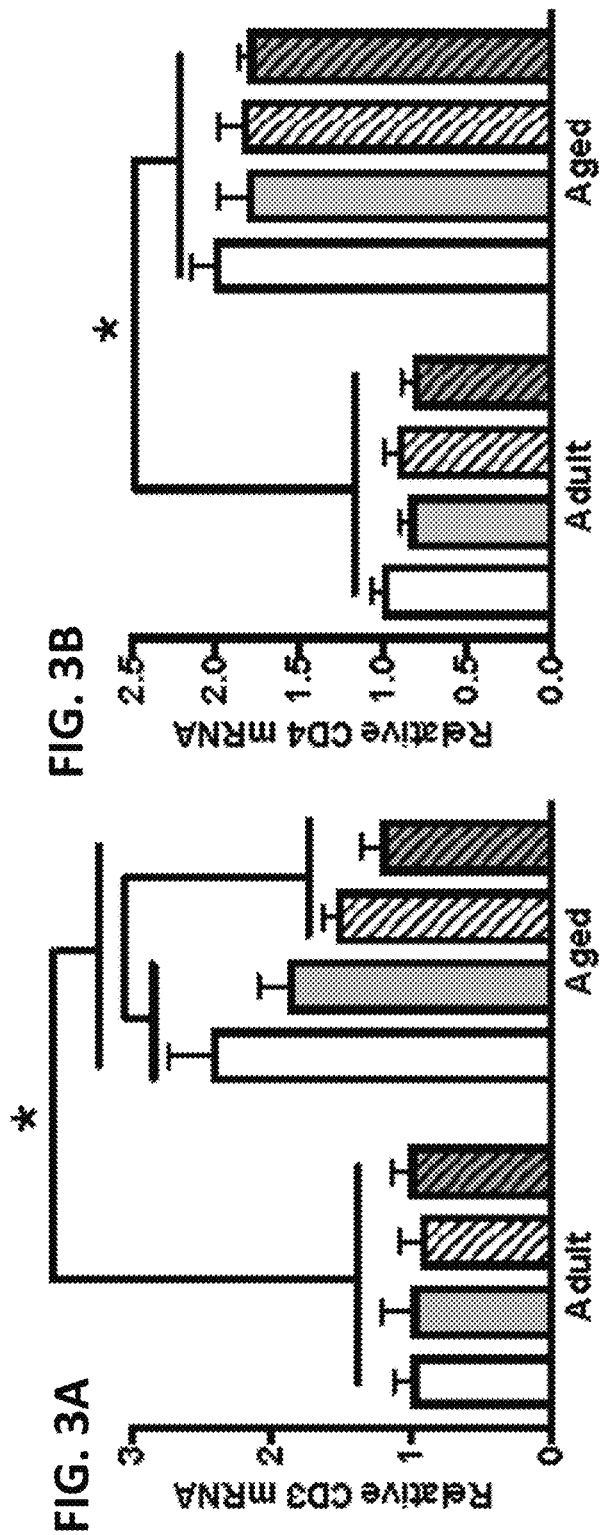
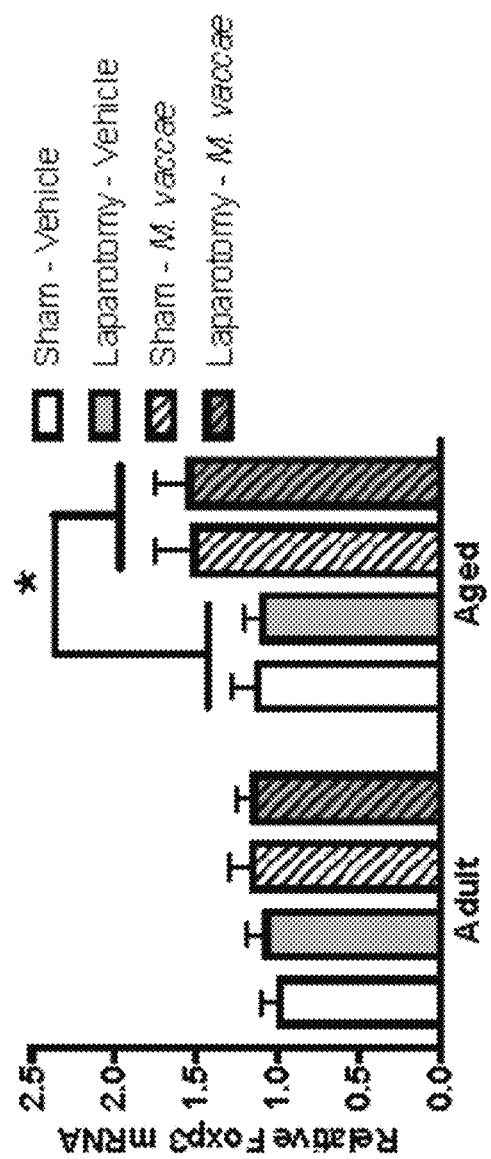

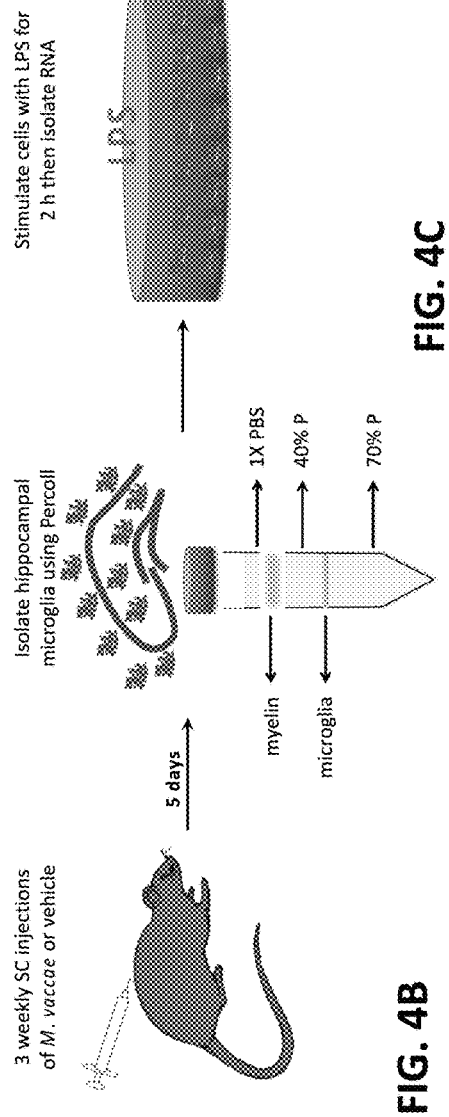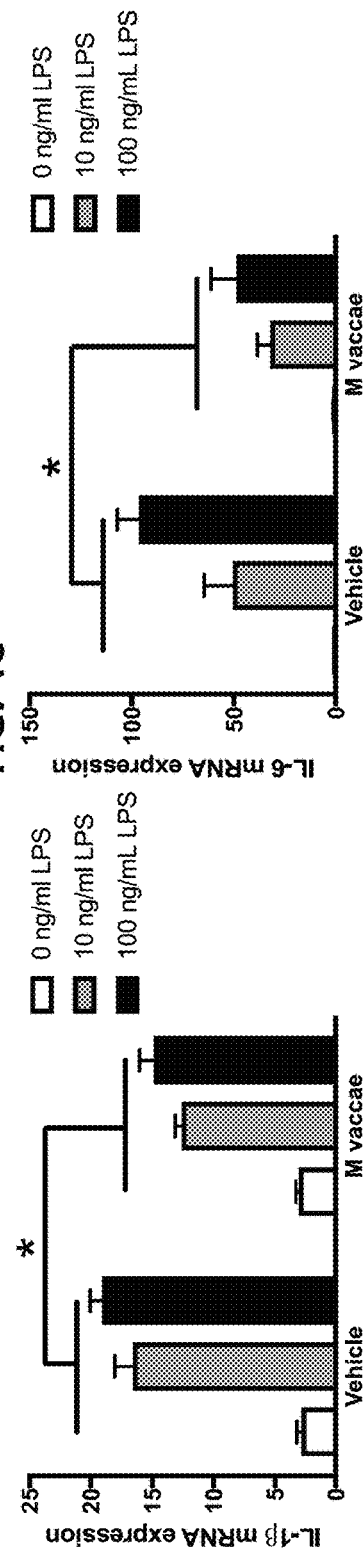

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial
<220> FEATURE:
<223> OTHER INFORMATION: Actb

<400> SEQUENCE: 1
ttccttcctg ggtatggaat                                              20

<210> SEQ ID NO 2
<211> LENGTH: 20
<212> TYPE: DNA
<213> ORGANISM: Artificial
<220> FEATURE:
<223> OTHER INFORMATION: Actb

<400> SEQUENCE: 2
gaggagcaat gatcttgatc                                              20

<210> SEQ ID NO 3
<211> LENGTH: 19
<212> TYPE: DNA
<213> ORGANISM: Artificial
<220> FEATURE:
<223> OTHER INFORMATION: Arg1

<400> SEQUENCE: 3
ctacctgctg ggaaggaag                                               19

<210> SEQ ID NO 4
```

```
<211> LENGTH: 20
<212> TYPE: DNA
<213> ORGANISM: Artificial
<220> FEATURE:
<223> OTHER INFORMATION: Arg1

<400> SEQUENCE: 4
gtcctgaaag tagccctgtc                                                     20

<210> SEQ ID NO 5
<211> LENGTH: 20
<212> TYPE: DNA
<213> ORGANISM: Artificial
<220> FEATURE:
<223> OTHER INFORMATION: Cd3e

<400> SEQUENCE: 5
aaagccagag tgtgcgagaa                                                     20

<210> SEQ ID NO 6
<211> LENGTH: 20
<212> TYPE: DNA
<213> ORGANISM: Artificial
<220> FEATURE:
<223> OTHER INFORMATION: Cd3e

<400> SEQUENCE: 6
ccttcctttt cttgctccag                                                     20

<210> SEQ ID NO 7
<211> LENGTH: 22
<212> TYPE: DNA
<213> ORGANISM: Artificial
<220> FEATURE:
<223> OTHER INFORMATION: Cd163

<400> SEQUENCE: 7
gtagtagtca ttcaaccctc ac                                                  22

<210> SEQ ID NO 8
<211> LENGTH: 20
<212> TYPE: DNA
<213> ORGANISM: Artificial
<220> FEATURE:
<223> OTHER INFORMATION: Cd163

<400> SEQUENCE: 8
cggcttacag tttcctcaag                                                     20

<210> SEQ ID NO 9
<211> LENGTH: 21
<212> TYPE: DNA
<213> ORGANISM: Artificial
<220> FEATURE:
<223> OTHER INFORMATION: Cd200

<400> SEQUENCE: 9
ctctctatgt acagcccata g                                                   21

<210> SEQ ID NO 10
<211> LENGTH: 21
<212> TYPE: DNA
<213> ORGANISM: Artificial
<220> FEATURE:
<223> OTHER INFORMATION: Cd200

<400> SEQUENCE: 10
```
gggagtgact ctcagtacta t                                              21

<210> SEQ ID NO 11
<211> LENGTH: 20
<212> TYPE: DNA
<213> ORGANISM: Artificial
<220> FEATURE:
<223> OTHER INFORMATION: Cd200r1

<400> SEQUENCE: 11 tagaggggt gaccaattat                                                 20

<210> SEQ ID NO 12
<211> LENGTH: 20
<212> TYPE: DNA
<213> ORGANISM: Artificial
<220> FEATURE:
<223> OTHER INFORMATION: Cd200r1

<400> SEQUENCE: 12
tacattttct gcagccactg                                                20

<210> SEQ ID NO 13
<211> LENGTH: 20
<212> TYPE: DNA
<213> ORGANISM: Artificial
<220> FEATURE:
<223> OTHER INFORMATION: Gfap

<400> SEQUENCE: 13
agatccgaga aaccagcctg                                                20

<210> SEQ ID NO 14
<211> LENGTH: 20
<212> TYPE: DNA
<213> ORGANISM: Artificial
<220> FEATURE:
<223> OTHER INFORMATION: Gfap

<400> SEQUENCE: 14
ccttaatgac ctcgccatcc                                                20

<210> SEQ ID NO 15
<211> LENGTH: 20
<212> TYPE: DNA
<213> ORGANISM: Artificial
<220> FEATURE:
<223> OTHER INFORMATION: Iba1

<400> SEQUENCE: 15
ggcaatggag atatcgatat                                                20

<210> SEQ ID NO 16
<211> LENGTH: 20
<212> TYPE: DNA
<213> ORGANISM: Artificial
<220> FEATURE:
<223> OTHER INFORMATION: Iba1

<400> SEQUENCE: 16
agaatcattc tcaagatggc                                                20

<210> SEQ ID NO 17
<211> LENGTH: 20
<212> TYPE: DNA

```
<213> ORGANISM: Artificial
<220> FEATURE:
<223> OTHER INFORMATION: Il1b

<400> SEQUENCE: 17
ccttgtgcaa gtgtctgaag                                              20

<210> SEQ ID NO 18
<211> LENGTH: 20
<212> TYPE: DNA
<213> ORGANISM: Artificial
<220> FEATURE:
<223> OTHER INFORMATION: Il1b

<400> SEQUENCE: 18
gggcttggaa gcaatcctta                                              20

<210> SEQ ID NO 19
<211> LENGTH: 20
<212> TYPE: DNA
<213> ORGANISM: Artificial
<220> FEATURE:
<223> OTHER INFORMATION: Il4

<400> SEQUENCE: 19
gaactcactg agaagctgca                                              20

<210> SEQ ID NO 20
<211> LENGTH: 20
<212> TYPE: DNA
<213> ORGANISM: Artificial
<220> FEATURE:
<223> OTHER INFORMATION: Il4

<400> SEQUENCE: 20
gaagtgcagg actgcaagta                                              20

<210> SEQ ID NO 21
<211> LENGTH: 22
<212> TYPE: DNA
<213> ORGANISM: Artificial
<220> FEATURE:
<223> OTHER INFORMATION: Il6

<400> SEQUENCE: 21
agaaaagagt tgtgcaatgg ca                                           22

<210> SEQ ID NO 22
<211> LENGTH: 22
<212> TYPE: DNA
<213> ORGANISM: Artificial
<220> FEATURE:
<223> OTHER INFORMATION: Il6

<400> SEQUENCE: 22
ggcaaatttc ctggttatat cc                                           22

<210> SEQ ID NO 23
<211> LENGTH: 21
<212> TYPE: DNA
<213> ORGANISM: Artificial
<220> FEATURE:
<223> OTHER INFORMATION: Il10

<400> SEQUENCE: 23
ggactttaag ggttacttgg g                                            21
```

```
<210> SEQ ID NO 24
<211> LENGTH: 20
<212> TYPE: DNA
<213> ORGANISM: Artificial
<220> FEATURE:
<223> OTHER INFORMATION: Il10

<400> SEQUENCE: 24
agaaatcgat gacagcgtcg                                              20

<210> SEQ ID NO 25
<211> LENGTH: 20
<212> TYPE: DNA
<213> ORGANISM: Artificial
<220> FEATURE:
<223> OTHER INFORMATION: Il13

<400> SEQUENCE: 25
agaccagaag acttccctgt                                              20

<210> SEQ ID NO 26
<211> LENGTH: 20
<212> TYPE: DNA
<213> ORGANISM: Artificial
<220> FEATURE:
<223> OTHER INFORMATION: Il13

<400> SEQUENCE: 26
tcaatatcct ctgggtcctg                                              20

<210> SEQ ID NO 27
<211> LENGTH: 20
<212> TYPE: DNA
<213> ORGANISM: Artificial
<220> FEATURE:
<223> OTHER INFORMATION: Mrc1

<400> SEQUENCE: 27
ggggttgttg ctgttgatgt                                              20

<210> SEQ ID NO 28
<211> LENGTH: 20
<212> TYPE: DNA
<213> ORGANISM: Artificial
<220> FEATURE:
<223> OTHER INFORMATION: Mrc1

<400> SEQUENCE: 28
gctcgaaacg gaaaaggttc                                              20

<210> SEQ ID NO 29
<211> LENGTH: 20
<212> TYPE: DNA
<213> ORGANISM: Artificial
<220> FEATURE:
<223> OTHER INFORMATION: Nts

<400> SEQUENCE: 29
tgcatcgaag gtcagcaaag                                              20

<210> SEQ ID NO 30
<211> LENGTH: 20
<212> TYPE: DNA
<213> ORGANISM: Artificial
<220> FEATURE:
```

```
<223> OTHER INFORMATION: Nts

<400> SEQUENCE: 30
tccttttcgc aacaaggtcg                                                 20

<210> SEQ ID NO 31
<211> LENGTH: 20
<212> TYPE: DNA
<213> ORGANISM: Artificial
<220> FEATURE:
<223> OTHER INFORMATION: Nfkbia

<400> SEQUENCE: 31
caccaactac aacggccaca                                                 20

<210> SEQ ID NO 32
<211> LENGTH: 20
<212> TYPE: DNA
<213> ORGANISM: Artificial
<220> FEATURE:
<223> OTHER INFORMATION: Nfkbia

<400> SEQUENCE: 32
gctcctgagc gttgacatca                                                 20

<210> SEQ ID NO 33
<211> LENGTH: 21
<212> TYPE: DNA
<213> ORGANISM: Artificial
<220> FEATURE:
<223> OTHER INFORMATION: Nlrp3

<400> SEQUENCE: 33
agaagctggg gttggtgaat t                                               21

<210> SEQ ID NO 34
<211> LENGTH: 21
<212> TYPE: DNA
<213> ORGANISM: Artificial
<220> FEATURE:
<223> OTHER INFORMATION: Nlrp3

<400> SEQUENCE: 34
gttgtctaac tccagcatct g                                               21

<210> SEQ ID NO 35
<211> LENGTH: 20
<212> TYPE: DNA
<213> ORGANISM: Artificial
<220> FEATURE:
<223> OTHER INFORMATION: Nr2f2

<400> SEQUENCE: 35
tgttcacctc agatgcctgt                                                 20

<210> SEQ ID NO 36
<211> LENGTH: 20
<212> TYPE: DNA
<213> ORGANISM: Artificial
<220> FEATURE:
<223> OTHER INFORMATION: Nr2f2

<400> SEQUENCE: 36
agggagacga agcaaaagct                                                 20
```

-continued

```
<210> SEQ ID NO 37
<211> LENGTH: 20
<212> TYPE: DNA
<213> ORGANISM: Artificial
<220> FEATURE:
<223> OTHER INFORMATION: Tgfb1

<400> SEQUENCE: 37
tactgcttca gctccacaga                                              20

<210> SEQ ID NO 38
<211> LENGTH: 20
<212> TYPE: DNA
<213> ORGANISM: Artificial
<220> FEATURE:
<223> OTHER INFORMATION: Tgfb1

<400> SEQUENCE: 38
tgtccaggct ccaaatgtag                                              20

<210> SEQ ID NO 39
<211> LENGTH: 19
<212> TYPE: DNA
<213> ORGANISM: Artificial
<220> FEATURE:
<223> OTHER INFORMATION: Tnf

<400> SEQUENCE: 39
caaggaggag aagttccca                                               19

<210> SEQ ID NO 40
<211> LENGTH: 19
<212> TYPE: DNA
<213> ORGANISM: Artificial
<220> FEATURE:
<223> OTHER INFORMATION: Tnf

<400> SEQUENCE: 40
ttggtggttt gctacgacg                                               19

<210> SEQ ID NO 41
<211> LENGTH: 20
<212> TYPE: DNA
<213> ORGANISM: Artificial
<220> FEATURE:
<223> OTHER INFORMATION: IL-4

<400> SEQUENCE: 41
caacaaggaa caccacggag                                              20

<210> SEQ ID NO 42
<211> LENGTH: 20
<212> TYPE: DNA
<213> ORGANISM: Artificial
<220> FEATURE:
<223> OTHER INFORMATION: IL-4

<400> SEQUENCE: 42
caacaaggaa caccacggag                                              20

<210> SEQ ID NO 43
<211> LENGTH: 20
<212> TYPE: DNA
<213> ORGANISM: Artificial
<220> FEATURE:
<223> OTHER INFORMATION: CD206
```

```
<400> SEQUENCE: 43
aatgggtgcc tccctggttt                                               20

<210> SEQ ID NO 44
<211> LENGTH: 19
<212> TYPE: DNA
<213> ORGANISM: Artificial
<220> FEATURE:
<223> OTHER INFORMATION: CD206

<400> SEQUENCE: 44
gggtcacccg ttttccagt                                                19

<210> SEQ ID NO 45
<211> LENGTH: 20
<212> TYPE: DNA
<213> ORGANISM: Artificial
<220> FEATURE:
<223> OTHER INFORMATION: MHCII

<400> SEQUENCE: 45
agcactggga gtttgaagag                                               20

<210> SEQ ID NO 46
<211> LENGTH: 20
<212> TYPE: DNA
<213> ORGANISM: Artificial
<220> FEATURE:
<223> OTHER INFORMATION: MHCII

<400> SEQUENCE: 46
aagccatcac ctcctggtat                                               20
```

PROTECTION FROM STRESS, ANXIETY, NEUROINFLAMMATION, AND COGNITIVE DYSFUNCTION

STATEMENT OF FEDERALLY SPONSORED RESEARCH

This invention was made with government support under grant numbers MH116263, MH108523, and AG048672 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 7, 2021, is named "90245-00323-sequence-listing-1" and is 7.94 Kbytes in size.

TECHNICAL FIELD

This invention relates generally to the field of neuroinflammation and in particular to an isolated *Mycobacterium*, for use in the prevention of neuroinflammation and the symptoms associated with such neuroinflammation. Also provided are methods of improving resilience in a subject by administering a therapeutically effective amount of an isolated *Mycobacterium*.

BACKGROUND

Anxiety and trauma-related disorders are the most commonly occurring of all mental disorders, with estimated lifetime prevalence as high as 25%. In addition to high prevalence, these disorders have an early age at onset, high chronicity, and involve substantial role impairment. Furthermore, anxiety and trauma-related disorders have significant psychiatric comorbidities including major depression, non-affective psychosis, and alcohol and drug abuse/dependence. Recent studies suggest that chronic inflammation contributes to risk of anxiety disorders, trauma, and stress-related disorders, as well as affective disorders, and it has been proposed that an enhanced stress-induced inflammatory immune activation plays a causal role in the development of these disorders. This is supported by studies demonstrating that interleukin (IL)-6, a pleiotropic cytokine released in association with inflammatory responses, is predictive for subsequent development of anxiety and depressive-like symptoms. Furthermore, lower numbers of regulatory T cells (Tregs) have been found in individuals with a diagnosis of anxiety, trauma, and stress-related disorders such as post-stressful or surgical stress disorder (PSSD) as well as in major depression.

Mental, behavioral, and neurological disorders have increased substantially in the elderly population in recent years and aging is a significant risk factor for cognitive decline in response to hospitalization and surgery. Postoperative cognitive dysfunction (POCD) is a loss in cognitive function after surgery. The loss may include memory, the ability to learn, the ability to concentrate, and/or the ability to reason and comprehend. The cognitive decline may be subtle, such that psychological testing is needed to detect it, or it may be profound and obvious. POCD does not refer to delirium that may occur immediately after surgery, but instead refers to cognitive loss that may persist weeks, months, or even permanently after surgery.

Age is the most salient predictor for the development of POCD, which is characterized by impairments in memory, concentration, and information processing following surgery and these impairments significantly impact quality of life and increase the risk of disability and mortality.

Amplified neuroinflammatory responses to challenge occur with normal aging and likely contribute to POCD vulnerability. In humans, inflammation is positively associated with the development of POCD. Factors that potentiate neuroinflammatory responses, such as opioids (e.g., fentanyl), increase the risk for developing delirium and POCD, whereas anti-inflammatory strategies (e.g., ketamine) reduce the risk for the development of POCD. There is also substantial evidence from animal models that age-related changes in neuroinflammatory dynamics are causal factors in the development of POCD. Peripheral immune stimuli (e.g., infection or surgery) induce potentiated neuroinflammatory and behavioral changes in aged mice and rats.

Elevations in hippocampal interleukin (IL)-1$\beta$, a cytokine that is considered a master regulator of neuroinflammation, likely mediate these cognitive impairments following surgery, as several lines of evidence demonstrate that aged rodents exhibit protracted elevations in IL-1$\beta$ post-surgery and that blocking IL-1$\beta$ signaling with pharmacological or transgenic approaches can prevent surgery-induced cognitive deficits. Importantly, aged but not senescent animals do not necessarily exhibit declines in cognition or increased pro-inflammatory cytokines under steady-state conditions. Rather, in aged animals, the neuroimmune response to immune challenge (e.g., surgery or infection) is potentiated; a phenomenon termed "priming." Age-associated inflammatory priming also occurs at the cellular level, in that microglia show potentiated responses to immune stimuli ex vivo. Primed inflammatory responses may develop with aging due to a combination of exogenous (environmental pollutants, pathogens, injury) and endogenous (changes in glucocorticoids, accumulation of danger signals, etc.) factors that accumulate over the lifespan.

Increases in chronic low-grade inflammation in modern urban societies have been attributed in part to reduced immunoregulation secondary to decreases in microbial exposures, as proposed by the hygiene hypothesis, "Old Friends" hypothesis, and biodiversity hypothesis. "Old Friends" needed to be tolerated by the immune system, as they were either part of host physiology (human microbiota), were harmless but inevitably contaminating air, food and water (environmental microbiota), or caused severe tissue damage when attacked by the host immune system (e.g., helminthic parasites).

There is a need for the development of treatments or preventative therapies for neuroinflammation and the associated behaviors and symptoms that are safe and effective.

SUMMARY OF THE INVENTION

The inventors have studied the effect of immunization with *Mycobacterium vaccae* (such as for example NCTC11659 among others) on neuroimmune regulation, stress-induced neuroinflammatory processes, and anxiety-like behavior, and discovered that exemplary mammals immunized with a heat-killed preparation of *M. vaccae* developed an anti-inflammatory immunophenotype in the hippocampus (increased interleukin (Il)4, Cd200r1, and Mrc1 mRNA expression), and increased IL4 protein. *M. vaccae* blocked stress-induced decreases in Cd200r1, increases in the alarmin HMGB1, and priming of the microglial response to immune challenge. Furthermore, *M. vaccae* prevented stress-induced increases in anxiety-like behavior, showing that *M. vaccae* enhances immunomodulation in the CNS and mitigates the neuroinflammatory and behavioral effects of stress, which may underpin its capacity to impart a stress resilient phenotype.

*M. vaccae* immunization also ameliorated age-associated neuroinflammatory priming in aged rats but not young rats. *M. vaccae* immunization protected aged rats from these surgery-induced cognitive impairments. *M. vaccae* immunization also shifted the aged proinflammatory hippocampal microenvironment towards an anti-inflammatory phenotype. Furthermore, M *vaccae* immunization reduced age-related hyperinflammatory responses in isolated hippocampal microglia. These data suggest that *M. vaccae* induces an anti-inflammatory milieu in the aged brain and mitigates the neuroinflammatory and behavioral effects of stress and the neuro-inflammatory and cognitive impairments induced by surgery.

Thus, this disclosure provides methods of using an isolated *Mycobacterium*, or its constituent parts, to prevent the development, or reduce the incidence, of stress and the neuro-inflammatory and cognitive impairments induced by surgery, and the symptoms of such behaviors and impairments.

This disclosure also provides methods of using an isolated *Mycobacterium*, or its constituent parts, to prevent or reduce a subject's levels of neuroinflammatory markers, including hippocampal microglial priming and the alarmin HMGB1, from being elevated following exposure to a surgery or other stress-inducing event.

These methods overcome deficiencies in the prior art by providing a safe, better tolerated, and effective methods for preventing neuroinflammation in subjects experiencing anxiety, stress, and/or postoperative subjects.

This disclosure also provides methods of treating or preventing stress, anxiety, or postoperative cognitive dysfunction (POCD) and the symptoms associated with such disorders in a subject, by administering a therapeutically effective amount of an isolated *Mycobacterium*, or its constituent parts, to the subject.

This disclosure also provides methods of inhibiting postoperative cognitive dysfunction (POCD) by administering an isolated *Mycobacterium M. vaccae*, or its constituent parts, to a subject in temporal proximity to administering a surgical anesthetic to the subject.

This disclosure also provides methods of treating or reducing the incidence of postoperative cognitive dysfunction (POCD) in a patient by administering a therapeutically effective amount of an isolated *Mycobacterium M. vaccae*, or its constituent parts, to the subject.

In these methods, the *Mycobacterium* may be *M. vaccae* such as a whole cell *M. vaccae*. Alternatively, or additionally, *M. vaccae* may comprise a non-pathogenic heat-killed *M. vaccae*. In these methods, the *Mycobacterium* may be *M. vaccae* strain NCTC 11659. In these methods, constituent parts of the *M. vaccae* may include organelles or biomolecules isolated from (e.g, extracted from) *M. vaccae*. The isolated biomolecules may include triacylglycerol lipid constituents of *M. vaccae*, and free fatty acid forms thereof. In exemplary embodiments, the triacylglycerol lipid constituent is the triglyceride, 1,2,3-tri[Z-10-hexadecenoyl]glycerol, and/or the free fatty acid form of the molecule, 10(Z)-hexadecenoic acid.

In these methods, the *M. vaccae* may be in the form of a vaccine composition optionally comprising an adjuvant. In these methods, the *M. vaccae* may be administered in two or more repeated doses. Alternatively, or additionally, in these methods, the *Mycobacterium* may be administered in a unit dose comprising an effective amount of non-pathogenic heat-killed *M. vaccae* from $10^1$ to $10^9$ cells. In these methods, the *M. vaccae* may be administered as a vaccination, which may be administered weekly, for example three separate vaccinations administered weekly to the subject.

In these methods, the *M. vaccae* may be formulated for administration via the parenteral, oral, sublingual, nasal or pulmonary route. In these methods, the parenteral route is selected from subcutaneous, intradermal, subdermal, intraperitoneal, intravenous, or intravesicular injection. In particular, the *M. vaccae* may be formulated for administration via the oral route.

In these methods, the administration may prevent at least one sign or symptom of stress, anxiety, or POCD wherein the sign or symptom is selected from disorganized or agitated behavior, problems with pain perception and pain tolerance, headache, difficult falling or staying asleep, or frightening dreams.

In these methods, the administration may prevent at least one sign or symptom of POCD selected from brain death, stroke, neuropsychological impairment comprising a decline in one or more of neuropsychological domains including memory, executive functioning, and speed of processing.

In these methods, the subject may be a human older than 50 years.

Additional aspects of the current inventive technology may include one or more of the following preferred embodied in the claims as set forth herein.

BRIEF DESCRIPTION OF FIGURES

FIGS. 1A-1C show that *M. vaccae* prevents laparotomy-induced cognitive impairments in aged rats. FIG. 1A shows the experimental outline: aged and young rats received subcutaneous *M. vaccae* injections once per week for three weeks. Five days following the final injection, rats underwent a laparotomy or sham procedure. Three days post-surgery, rats underwent training in a pre-exposure fear-conditioning paradigm. Freezing behavior in the (FIG. 1B) conditioned and (FIG. 1C) novel context of the fear-conditioning paradigm is presented as percent of total time (6 min) freezing (Freezing %). Results were analyzed using a 2×2×2 ANOVA with age, surgery, and *M. vaccae* treatment as between-subjects' factors (n=6/group). Data are expressed as mean±SEM. *differs from all other groups, $p<0.05$.

FIGS. 2A-2F show the hippocampal pro-inflammatory environment in aged rats was abrogated by *M. vaccae* treatment. FIG. 2A is the experimental outline. Hippocampal IL-1β (FIG. 2B) gene and (FIG. 1C) protein expression were elevated in aged rats that underwent a laparotomy procedure and reduced by *M. vaccae* treatment. FIG. 1D shows NFKBIA was also elevated by surgery in aged rats and reduced by *M. vaccae*. *M. vaccae* treatment upregulated (FIG. 1E) IL-4 and (FIG. 1F) Arginasel mRNA expression. Results were analyzed using a 2×2×2 ANOVA with age, surgery, and *M. vaccae* treatment as between-subjects' factors (n=6-7/group). Data are expressed as mean±SEM. *differs from all other groups, †effect of *M. vaccae*, $p<0.05$.

FIGS. 3A-3C show that T cell markers are regulated by aging and *M. vaccae*. FIG. 3A shows CD3 mRNA expression was upregulated in the hippocampus of aged as compared to young rats and reduced by *M. vaccae* immunization. FIG. 3B shows CD4 mRNA expression was upregulated in the aged rat hippocampus and FIG. 3C shows that Foxp3 mRNA expression was elevated in aged rats by *M. vaccae* treatment. Results were analyzed using a 2×2×2

ANOVA with age, surgery, and *M. vaccae* treatment as between-subjects' factors (n=6-7/group). Data are expressed as mean±SEM. *p<0.05.

FIGS. 4A-4D show microglia isolated from aged rats are less inflammatory following in vivo *M. vaccae* treatment. FIG. 4A shows the experimental design: aged rats received subcutaneous *M. vaccae* injections once per week for three weeks. Five days following the final injection, microglia were isolated from the hippocampus and stimulated with LPS. FIG. 4B shows IL-1β, (FIG. 4C) IL-6, and (FIG. 4D) NFKBIA mRNA expression were reduced in microglia isolated from aged *M. vaccae*-treated rats compared to vehicle-treated rats. Data are expressed as mean±SEM. *p<0.05.

Figure 5:
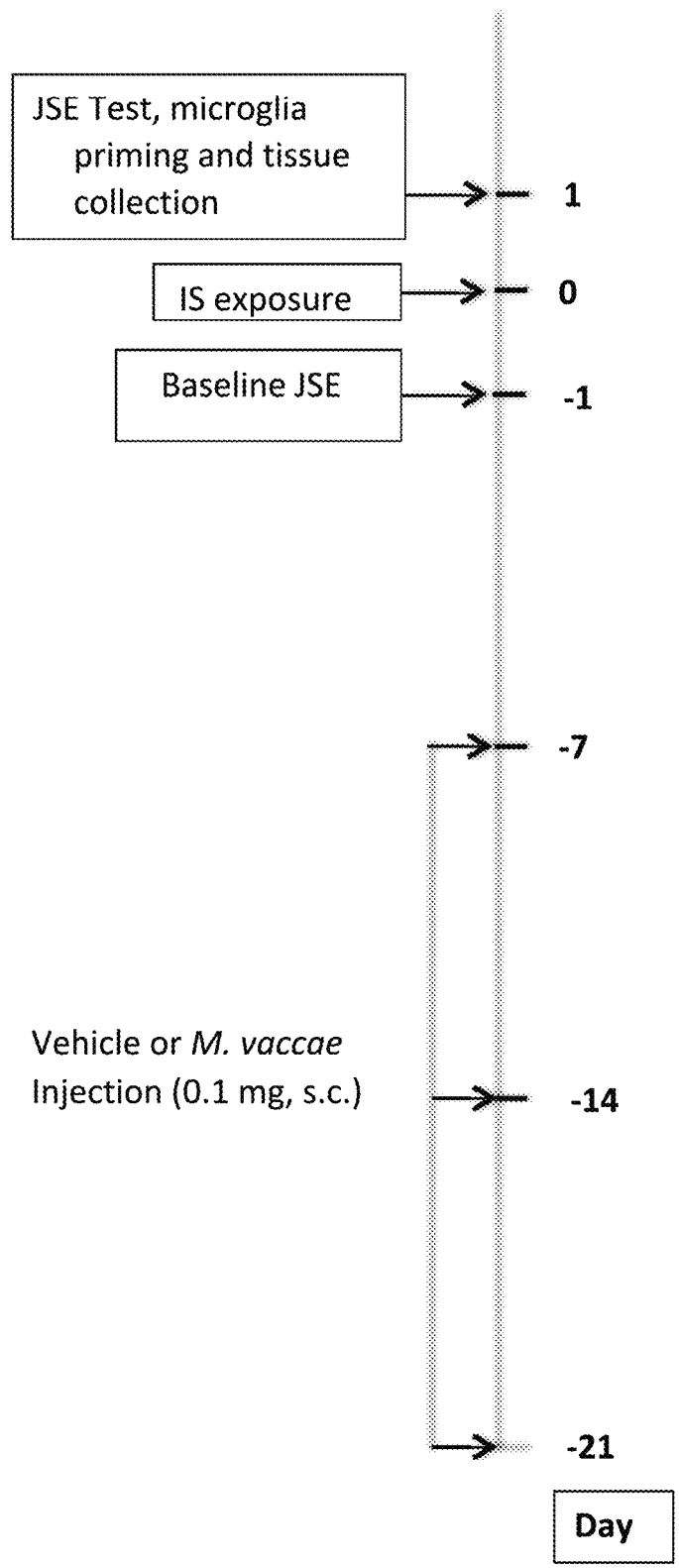

FIG. 5 is a schematic depicting the timing of *M. vaccae* treatment relative to stress exposure (IS; inescapable tailshock), behavioral testing (JSE; juvenile social exploration) and tissue collection.

Figure 6A:
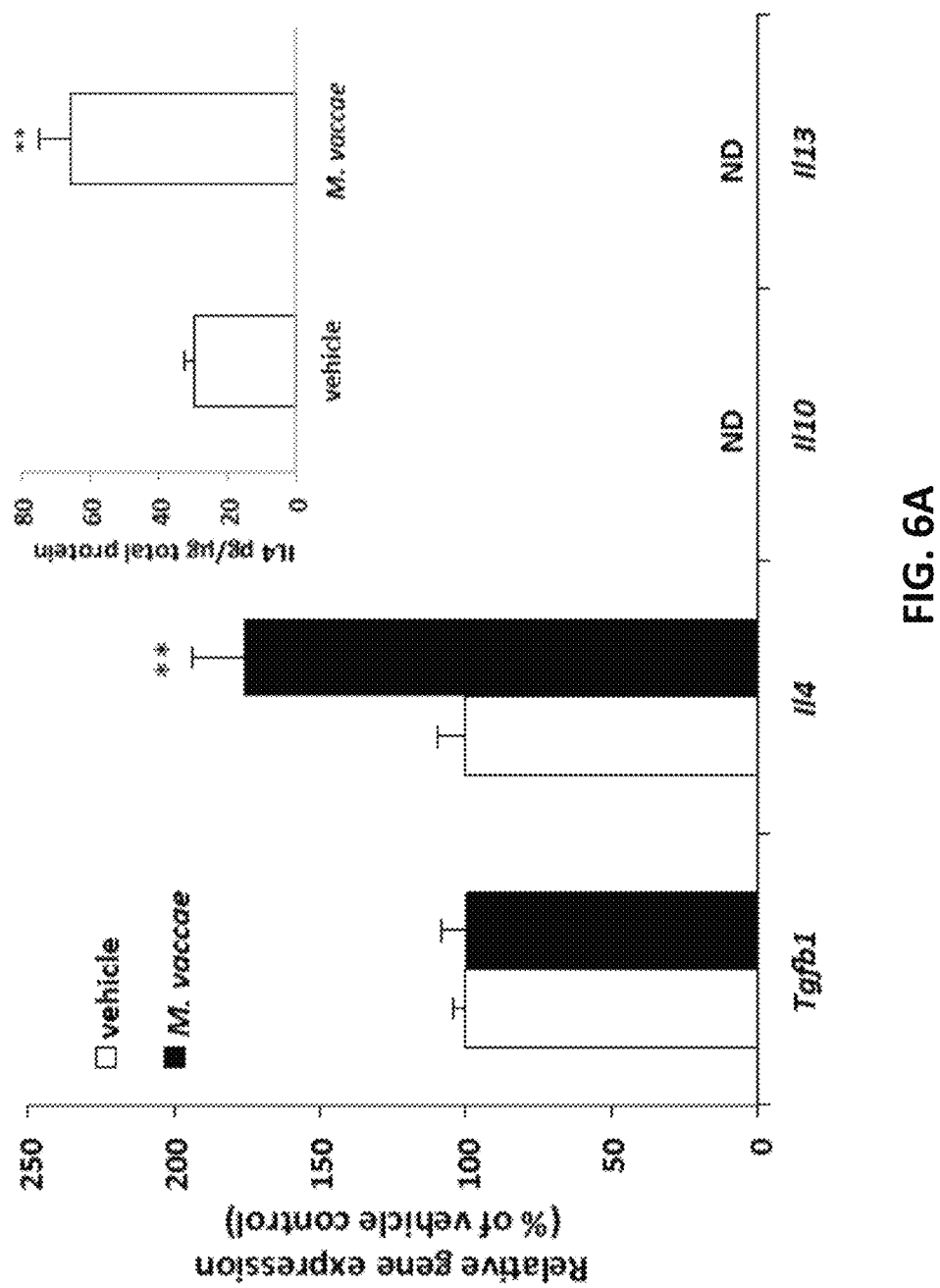
Figure 6B:
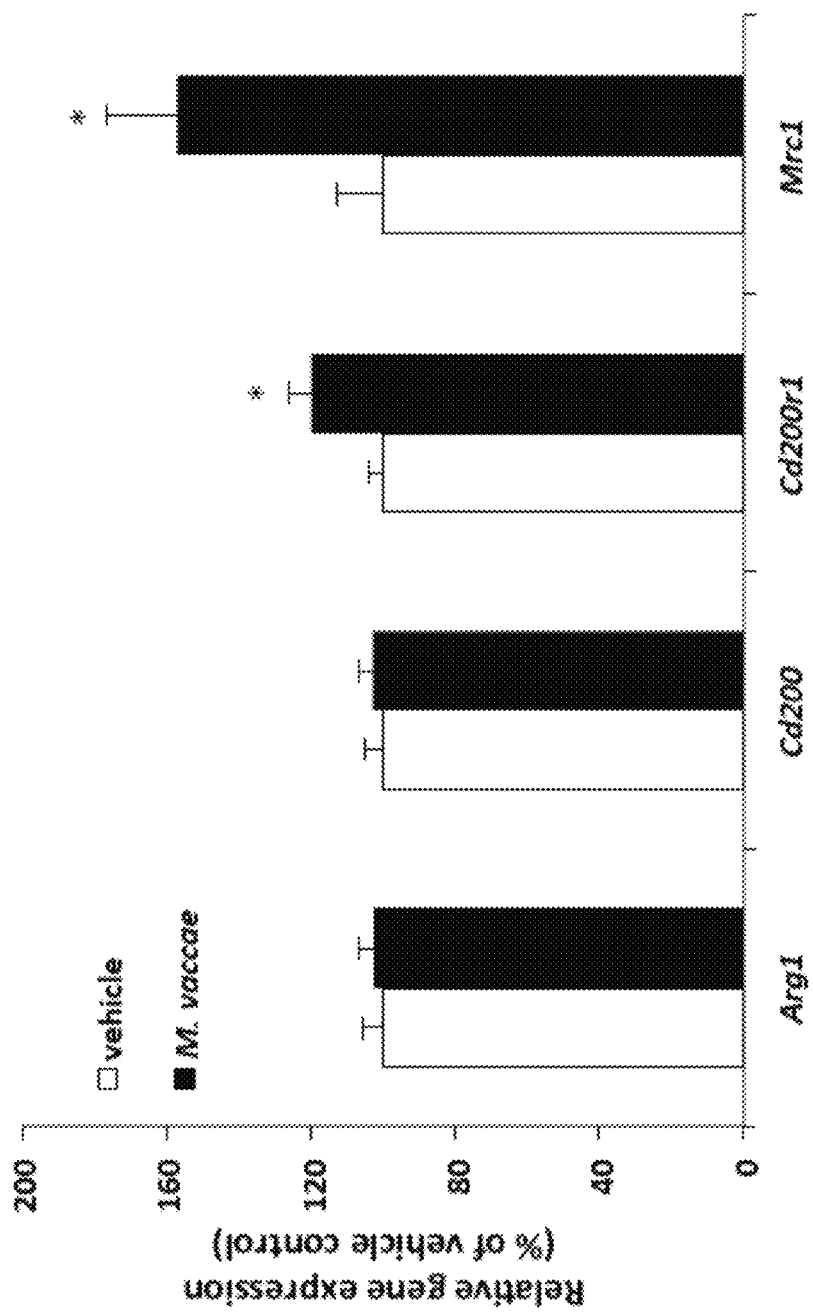

FIGS. 6A and 6B show the effect of *M. vaccae* on hippocampal anti-inflammatory mediators and markers of alternative activation. Animals received 3 injections of either vehicle or *M. vaccae* (0.1 mg, s.c.). Eight days after the third injection, gene expression of anti-inflammatory mediators (FIG. 6A) and markers of alternative macrophage activation (FIG. 6B) were measured in hippocampus. Data are presented as the mean+s.e.m. N=9-12 animals per experimental group. Significant *M. vaccae* effects compared to vehicle, * p<0.05, ** p<0.01. ND=non-detected.

Figure 7:
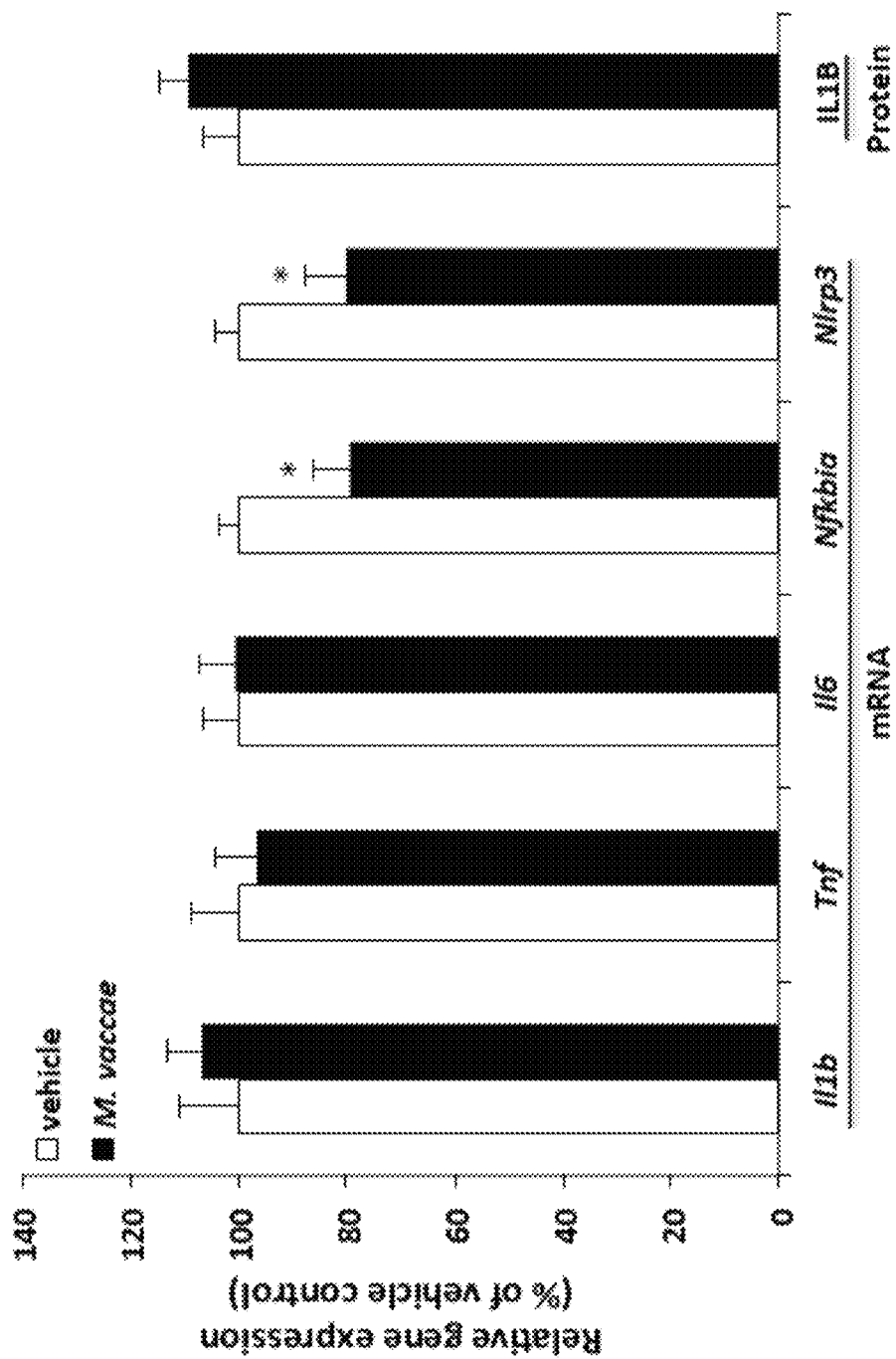

FIG. 7 shows the effect of *M. vaccae* on hippocampal proinflammatory mediators. Animals received 3 injections of either vehicle or *M. vaccae* (0.1 mg, s.c.). Eight days after the third injection, gene expression of hippocampal proinflammatory mediators was measured. Data are presented as the mean+s.e.m. N=9-12 animals per experimental group. Significant *M. vaccae* effects compared to vehicle, * p<0.05.

Figure 8:
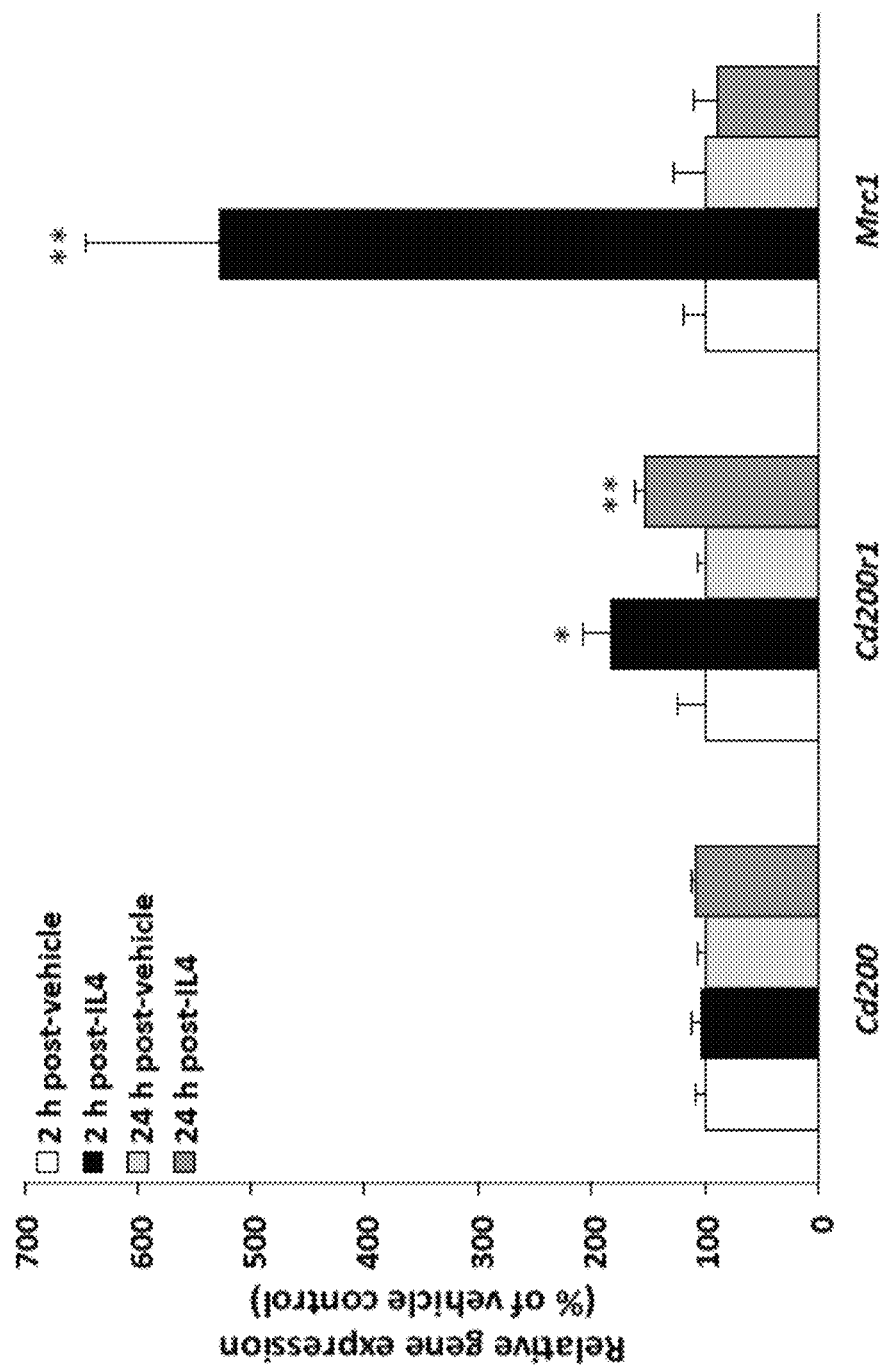

FIG. 8 shows the effect of recombinant interleukin 4 (rIL4) on the hippocampal immunophenotype. Animals received injections of either vehicle or rIL4 (100 ng, i.c.m.). IL4-sensitive target genes were measured in hippocampus at 2 h (N=6-8 per group) or 24 h post-injection (N=4 per group). Data are presented as the mean+s.e.m. Significant *M. vaccae* effects compared to vehicle at each timepoint post-injection, * p<0.05, ** p<0.01.

Figure 9B:
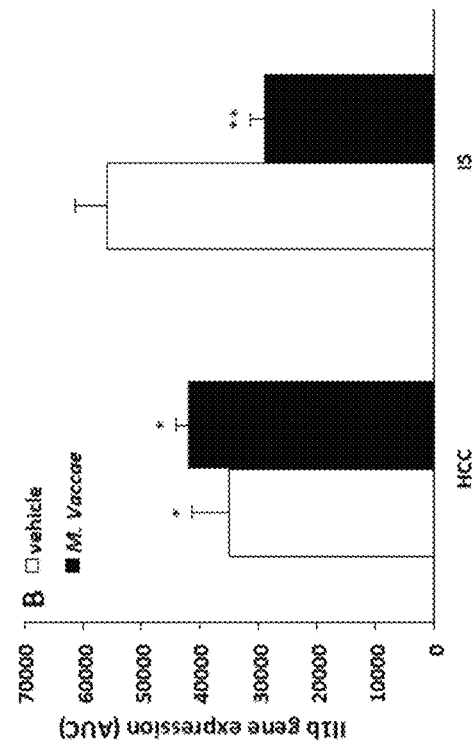
Figure 9D:
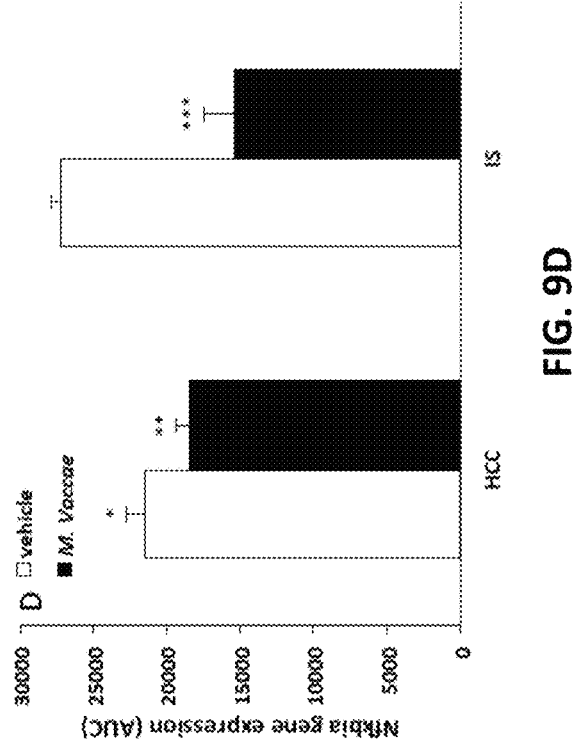
Figure 9A:
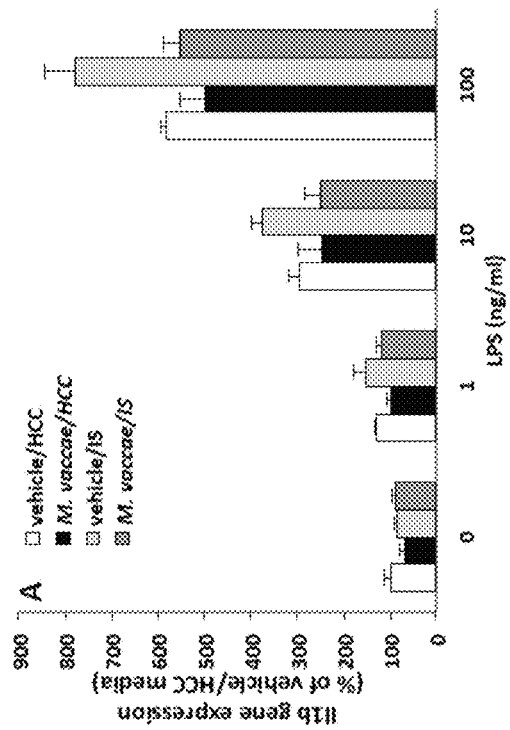
Figure 9C:
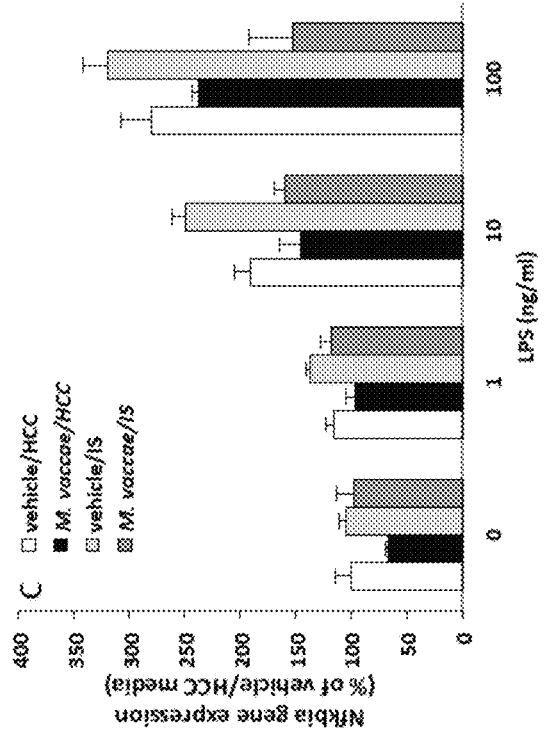

FIGS. 9A-9D show the effect of *M. vaccae* on stress-induced microglial priming. Animals received 3 injections of either vehicle or *M. vaccae* (0.1 mg, s.c.). Seven days after the third injection, animals were exposed to stress (IS; inescapable tailshock) or served as home cage controls (HCCs). 24 h post-IS, hippocampal microglia were isolated from all animals and exposed to several concentrations of LPS (0, 1, 10 and 100 ng/ml) for 2 h. FIGS. 9A and 9C show the cytokine response (Il1b and Nfkbia) at each concentration of LPS was captured, and FIGS. 9B and 9D show the overall magnitude of the cytokine response (area-under-the-curve; AUC) computed. N=4/experimental group. Data are presented as the mean+s.e.m. For the AUC data, the vehicle/IS treatment group significantly differed from all other treatment groups, * p<0.05,  p<0.01, * p<0.001.

Figure 10:
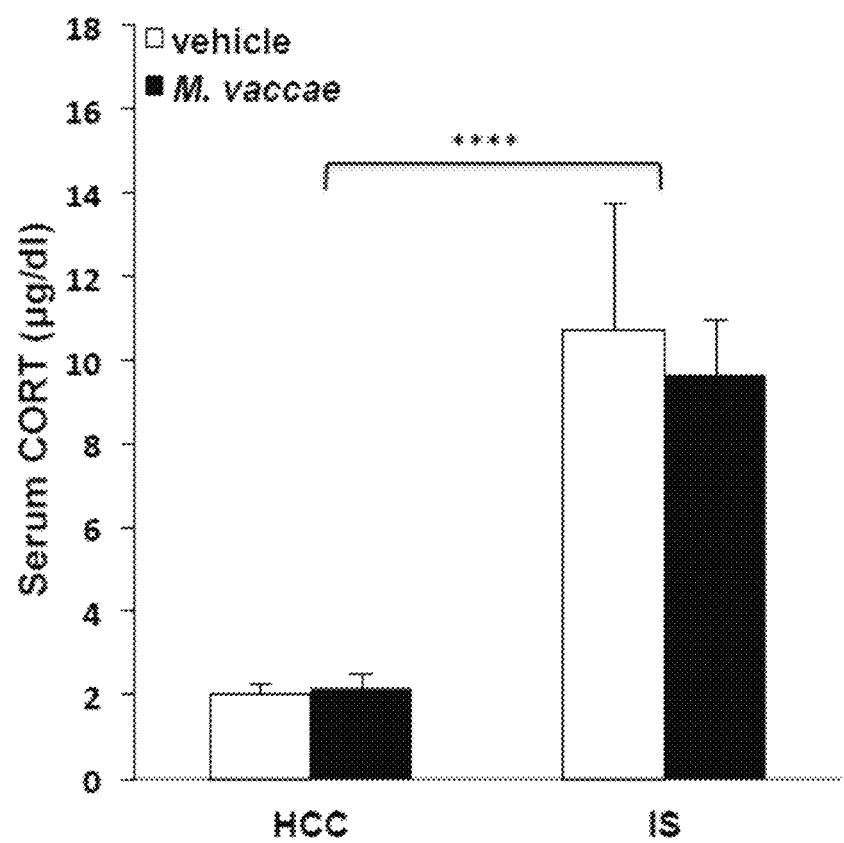

FIG. 10 shows the effect of *M. vaccae* on basal and stress-induced serum corticosterone (CORT) levels. Animals received 3 injections of either vehicle or *M. vaccae* (0.1 mg, s.c.). Seven days after the third injection, animals were exposed to stress (IS; inescapable tailshock) or served as home cage controls (HCCs). 24 h post-IS, serum CORT levels were measured. N=9-12 animals per group. Data are presented as the mean+s.e.m. IS independent of *M. vaccae* treatment increased serum CORT compared to HCC, **** p<0.0001.

Figure 11A:
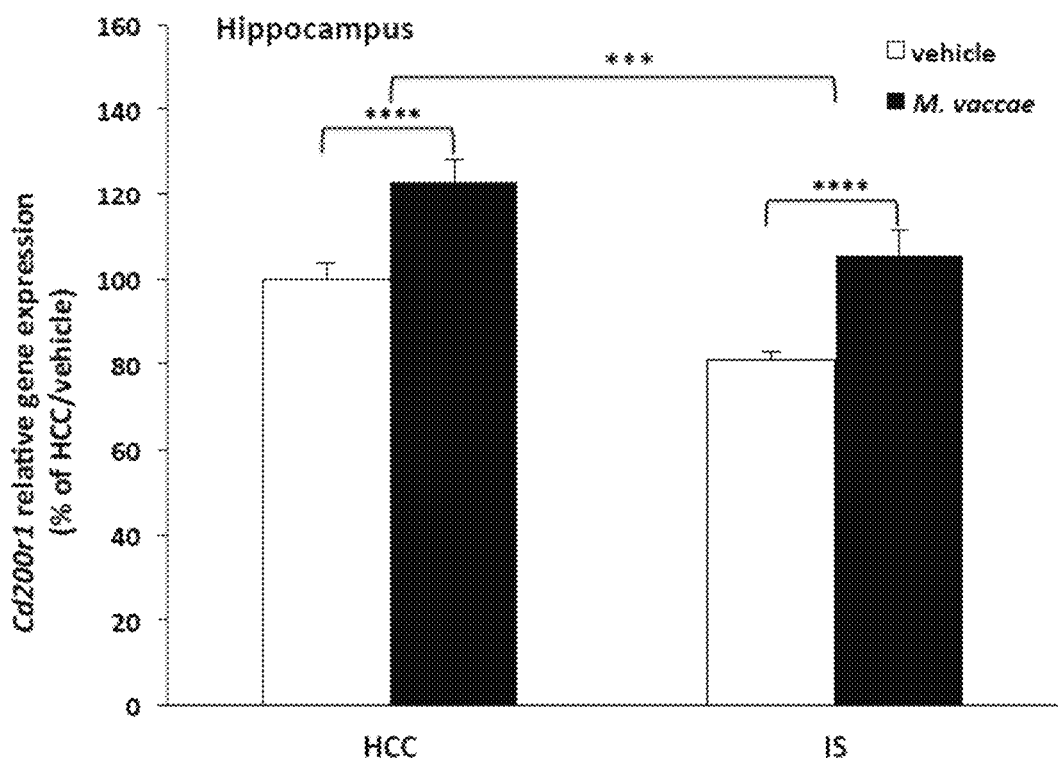
Figure 11B:
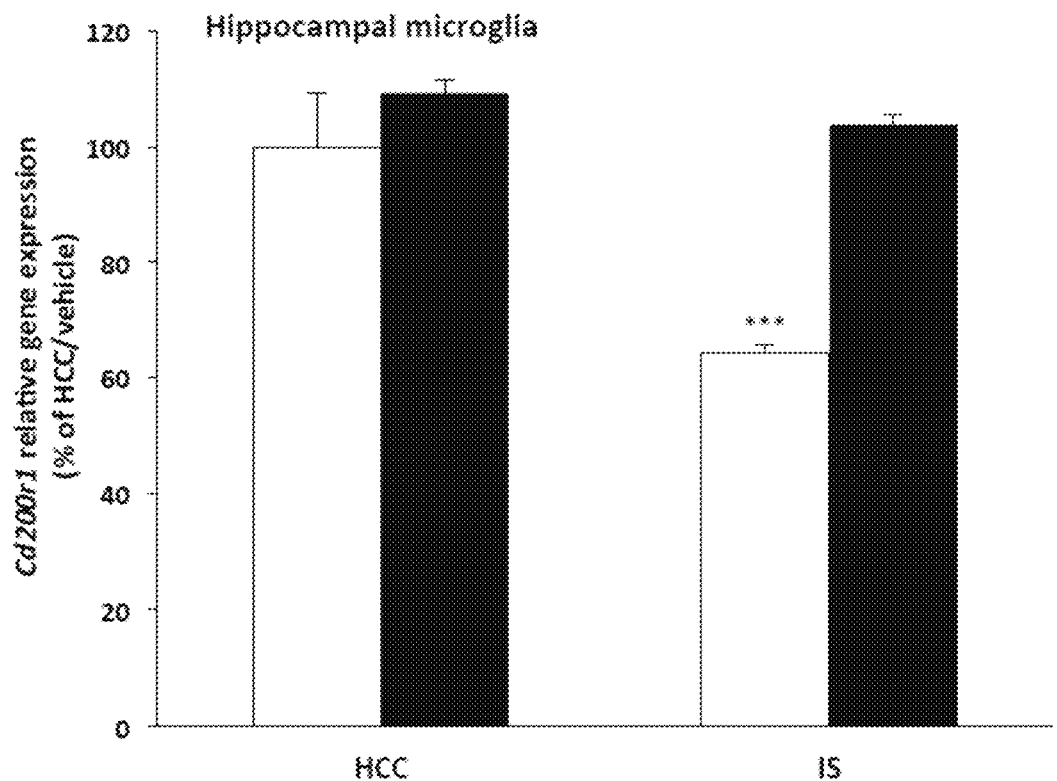

FIGS. 11A and 11B show the effect of *M. vaccae* on stress-induced reductions in Cd200r1. Animals received 3 injections of either vehicle or *M. vaccae* (0.1 mg, s.c.). Seven days after the third injection, animals were exposed to stress (IS; inescapable tailshock) or served as home cage controls (HCCs). Twenty-four h post-IS, Cd200r1 expression was measured in whole hippocampal tissue (FIG. 11A) (N=10-12 animals per group) and hippocampal microglia ex vivo (FIG. 11B) (N=4 animals per group). Data are presented as the mean+s.e.m. In FIG. 11A, the main effect of HCC vs IS, *** p<0.001; the main effect of vehicle vs *M. vaccae*, ** p<0.0001. In FIG. 11B, the vehicle/IS treatment group significantly differed from all other treatment groups, * p<0.001.

Figure 12:
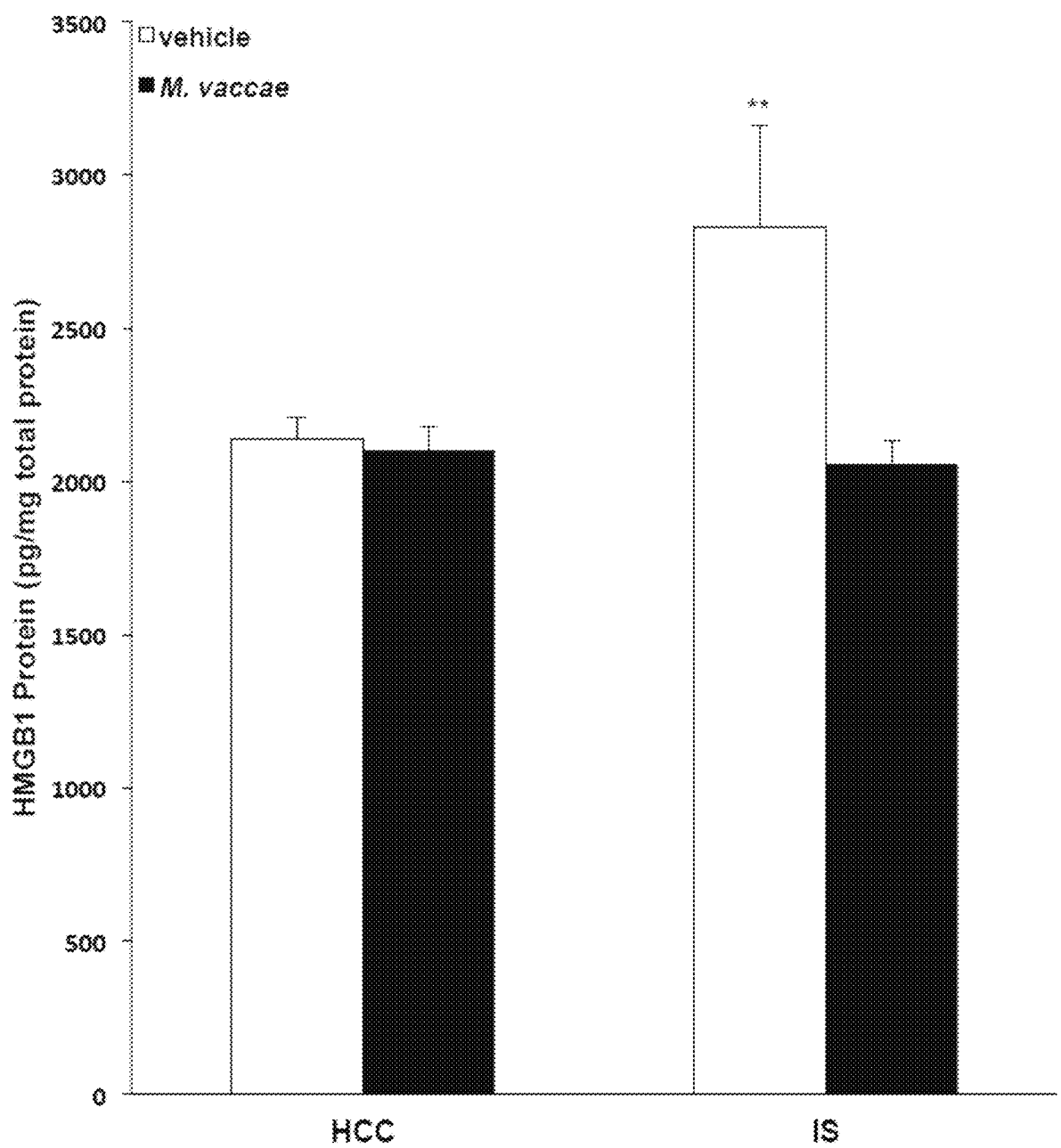

FIG. 12 shows the effect of *M. vaccae* on stress-induced HMGB1. Animals received 3 injections of either vehicle or *M. vaccae* (0.1 mg, s.c.). Seven days after the third injection, animals were exposed to stress (IS; inescapable tailshock) or served as home cage controls (HCCs). Twenty-four h post-IS, hippocampal HMGB1 protein levels were measured. N=9-12 animals per group. Data are presented as the mean+s.e.m. The vehicle/IS treatment group significantly differed from all other treatment groups, ** p<0.01.

Figure 13:
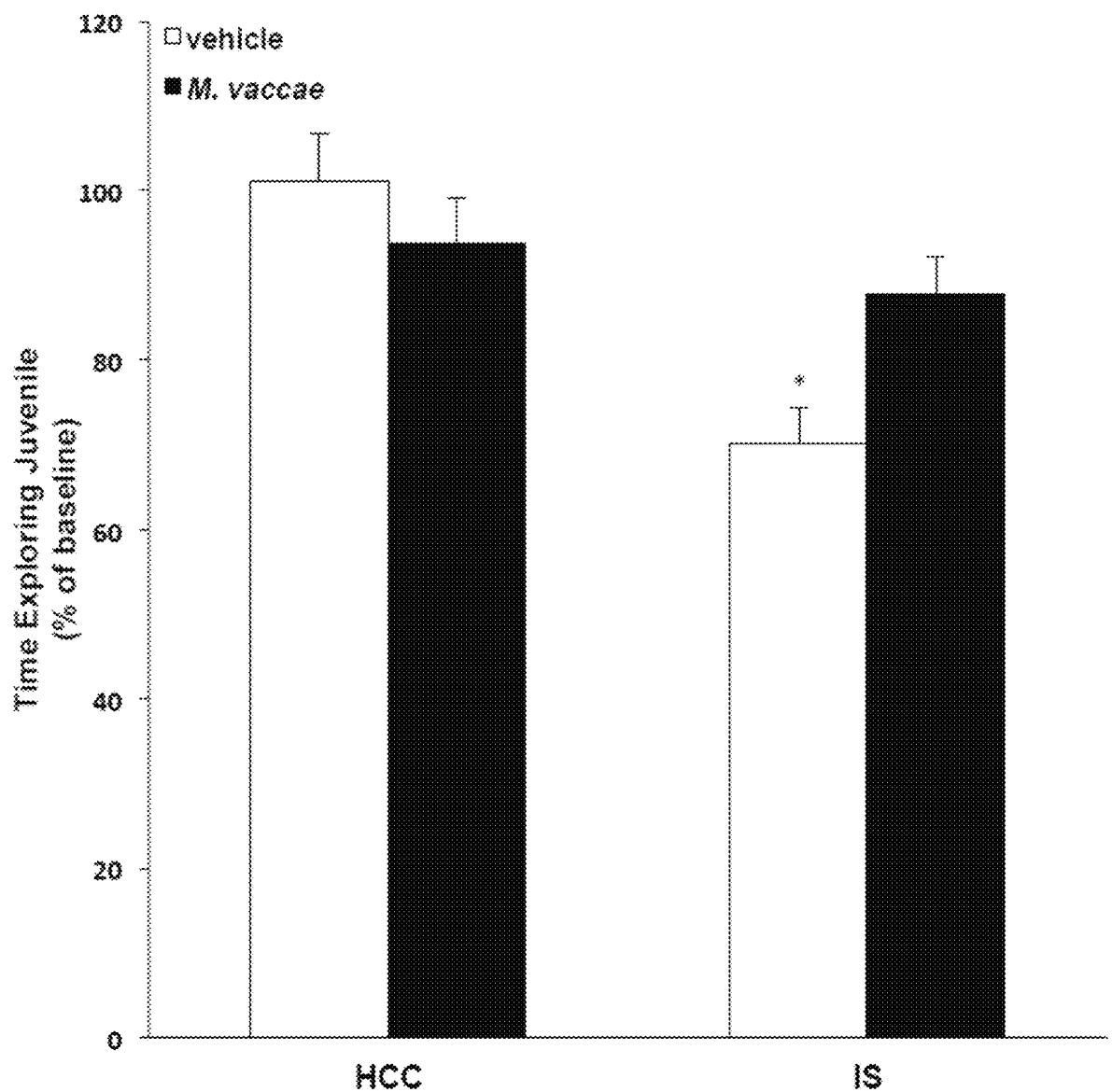

FIG. 13 shows the effect of *M. vaccae* on stress-induced anxiety-like behavior. Animals received 3 injections of either vehicle or *M. vaccae* (0.1 mg, s.c.). Six days after the third injection, baseline juvenile social exploration (JSE) was measured in all animals. Twenty-four hours after baseline testing, animals were exposed to stress (IS; inescapable tailshock) or served as home cage controls (HCCs). Twenty-four h post-IS, JSE was measured. Data are presented as a percent of baseline JSE. N=10-12 animals per group. Data are presented as the mean+s.e.m. The IS/vehicle treatment group significantly differed from all other groups, * p<0.05.

Figure 14A:
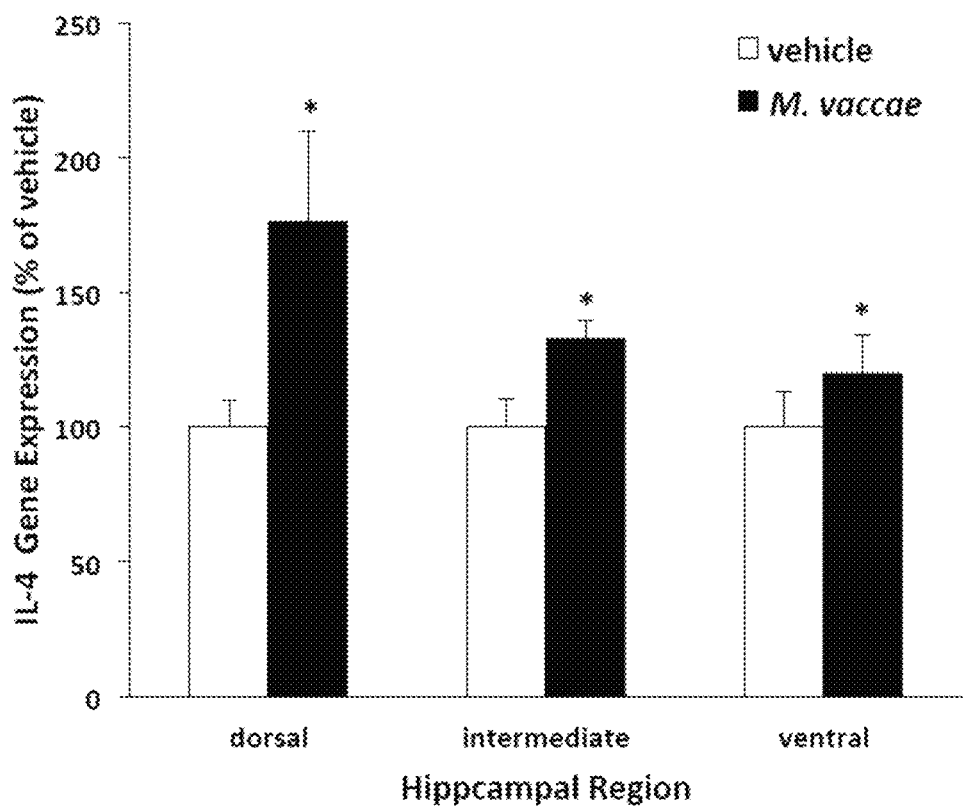
Figure 14B:
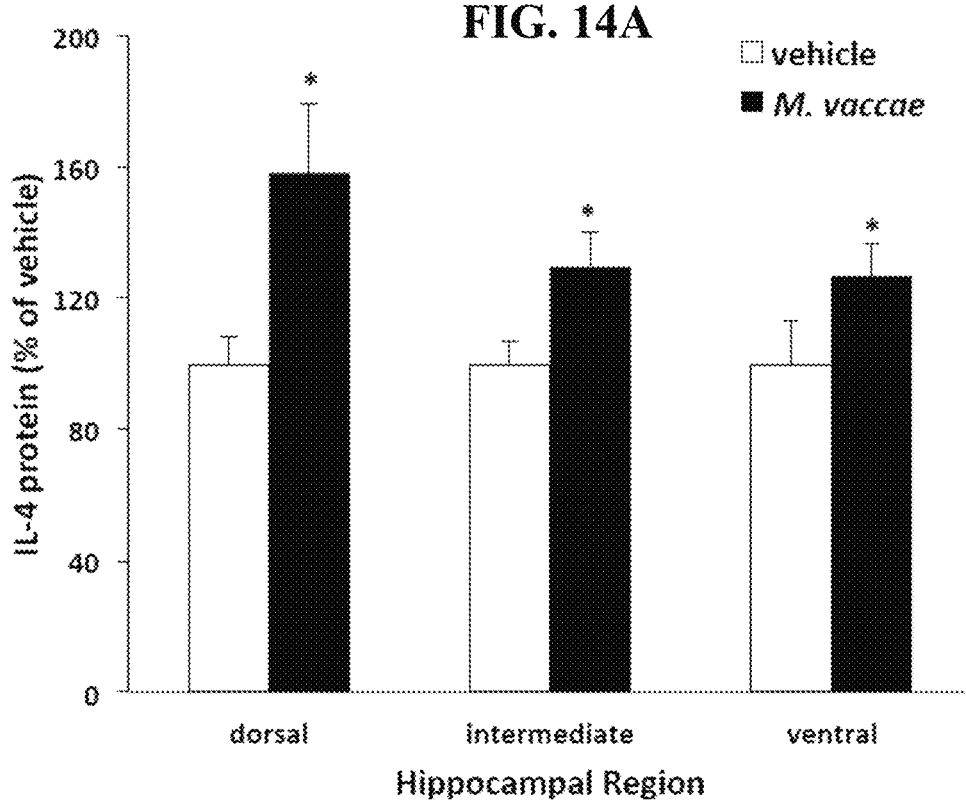

FIGS. 14A and 14B show the effect of *M. vaccae* on IL4 mRNA and protein expression in subregions of the hippocampus. Animals received 3 injections of either vehicle or *M. vaccae* (0.1 mg, s.c.). Eight days after the third injection, IL4 mRNA expression (FIG. 14A) and IL4 protein levels (FIG. 14B) were measured in dorsal, intermediate, and ventral hippocampus. Data are presented as the mean+s.e.m. N=8 animals per experimental group. Significant main effect of *M. vaccae* compared to vehicle, * p<0.05.

Figure 15:
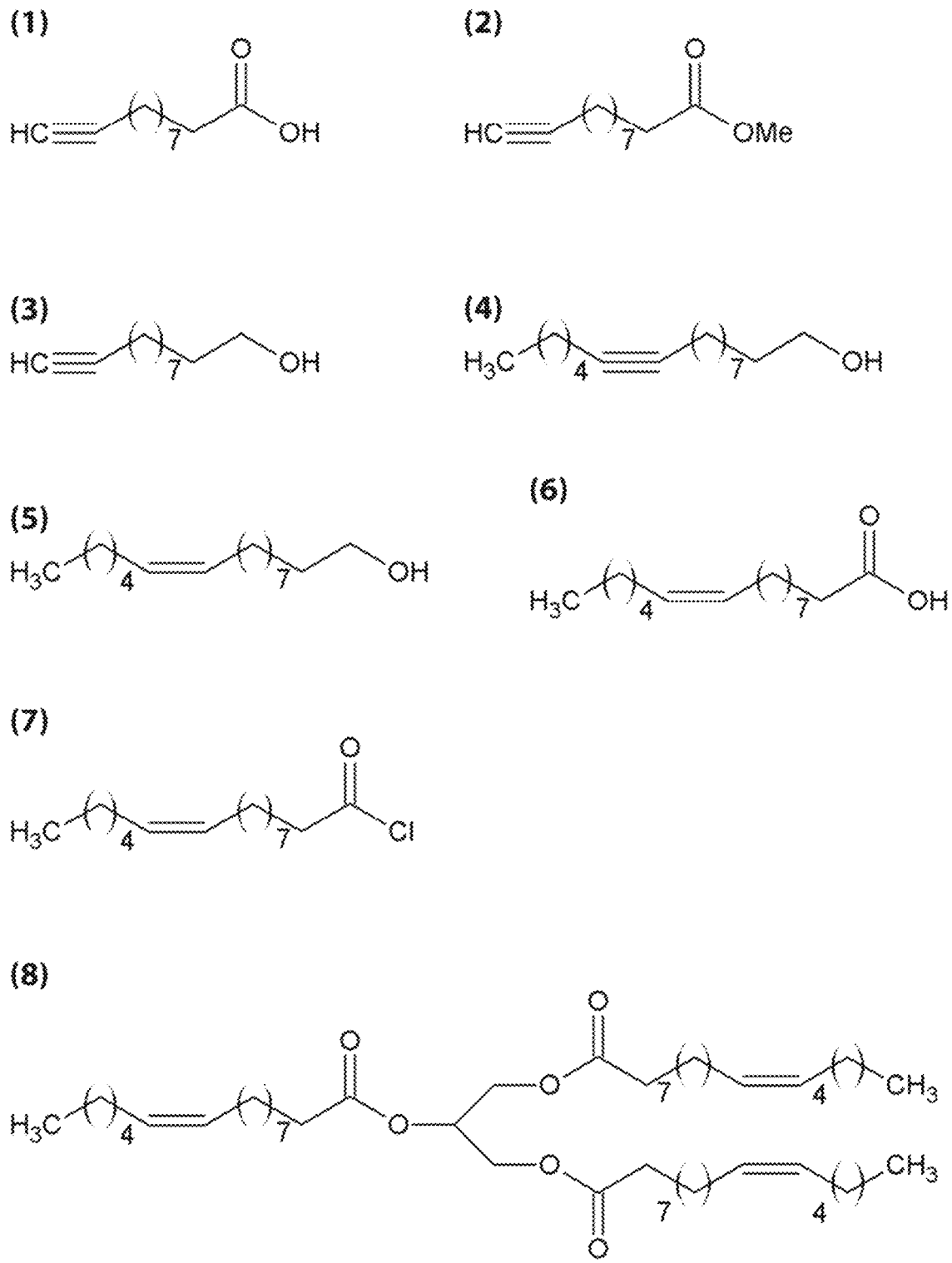

FIG. 15 shows the structures associated with the synthesis of the triacylglycerol, 1,2,3-tri[Z-10-hexadecenoyl]glycerol, isolated from extracts of *M. vaccae*.

Figure 16:
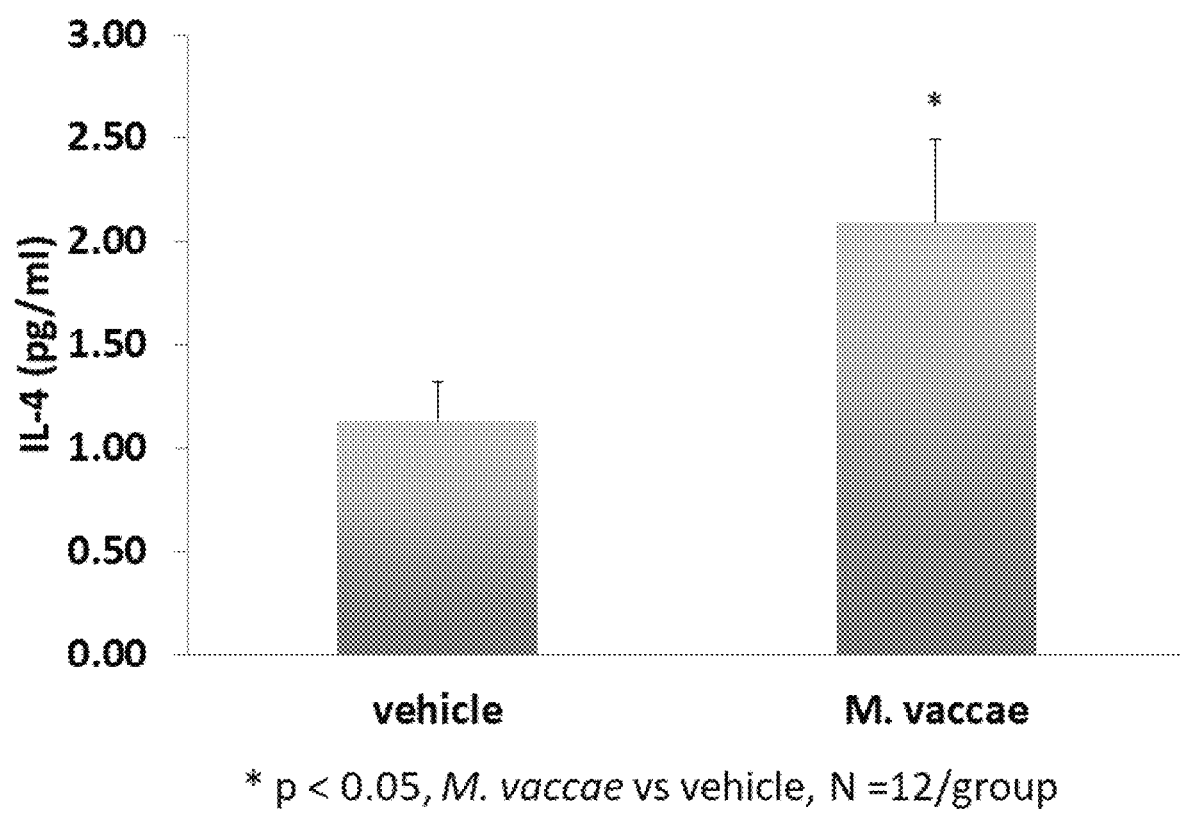

FIG. 16 shows the effect of *M. vaccae* on IL4 protein in serum. Serum ELISA data demonstrates that *M. vaccae* increases IL4 protein in serum compared to vehicle, * p<0.05, where N=12/group.

Figure 17:
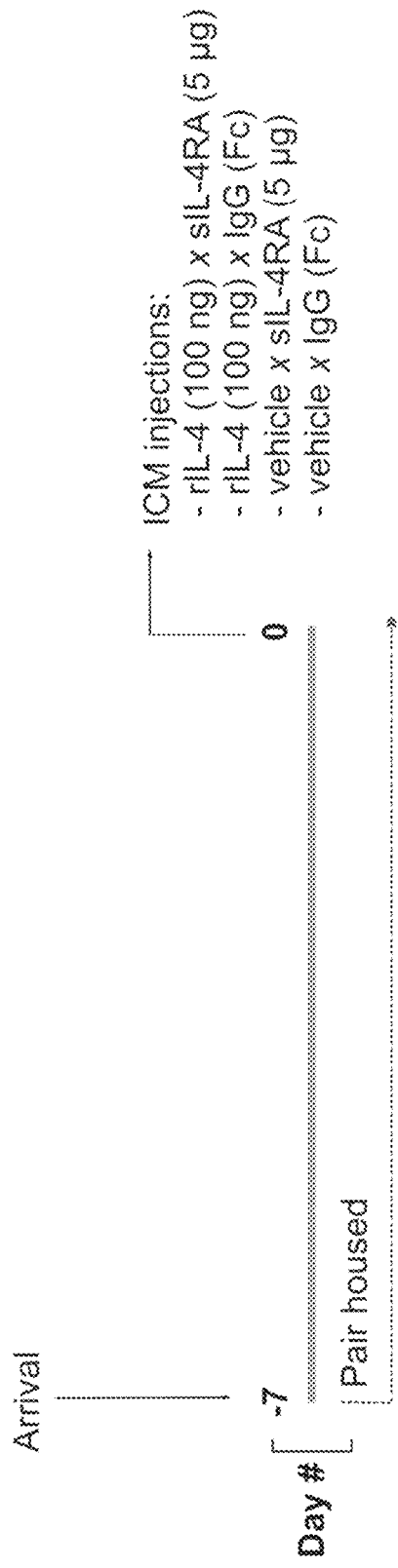

FIG. 17 is a schematic depicting an exemplary experimental design to demonstrate the relationship of *M. vaccae* and IL-4 increases via administration of recombinant IL-4.

Figure 18:
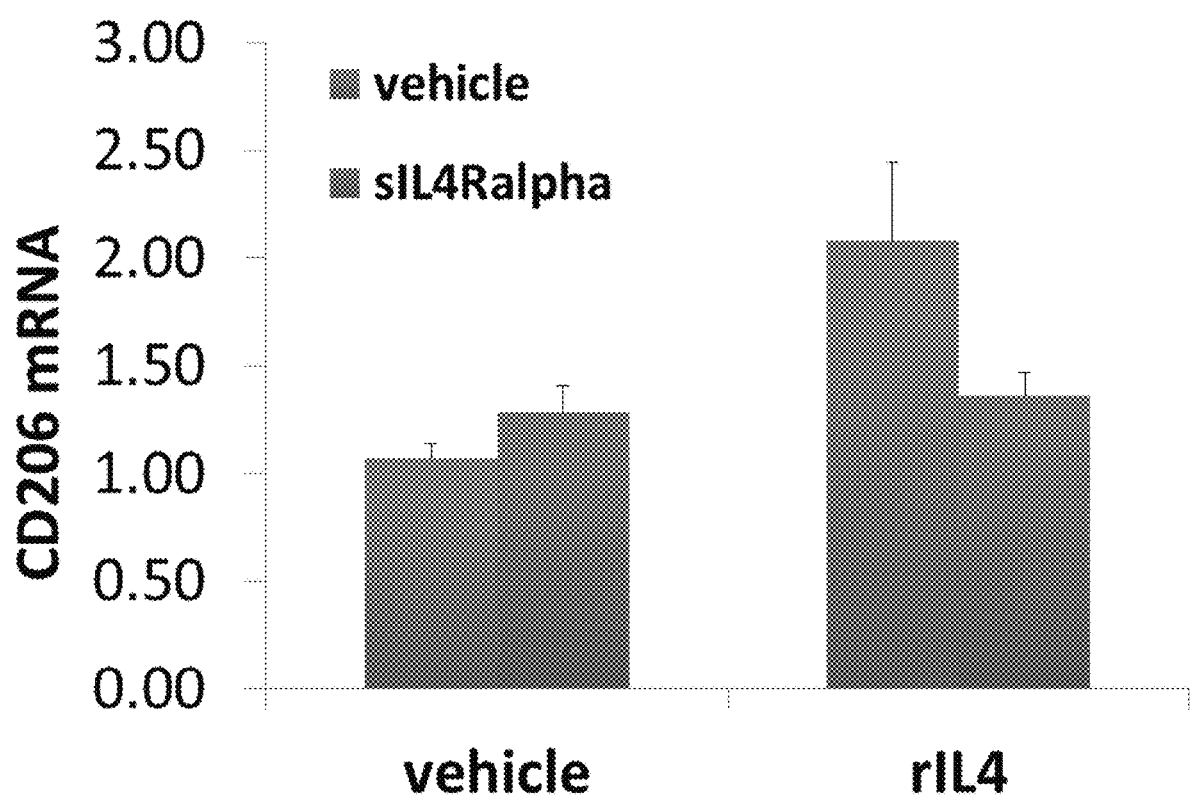

FIG. 18 shows experimental data establishing the relationship of *M. vaccae* and IL-4 increases via recombinant IL-4 utilizing rt-PCR procedures to measure the marker cluster of differentiation 206 (CD206) mRNA.

Figure 19:
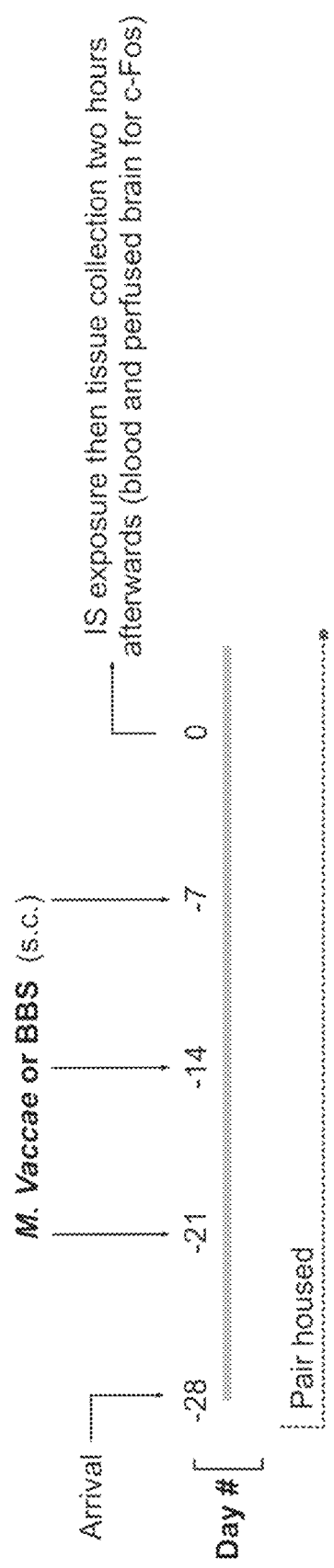

FIG. 19 is a schematic depicting the timing of *M. vaccae* or borate-buffered saline (BBS) treatment relative to IS (inescapable tail shock) and tissue collection and detection of C-Fos. Notably, C-fos is a proto-oncogene that is expressed within neurons following depolarization. The protein product, c-fos protein, can be identified by immunohistochemical techniques making it a useful marker of cell activation.

Figure 20A:
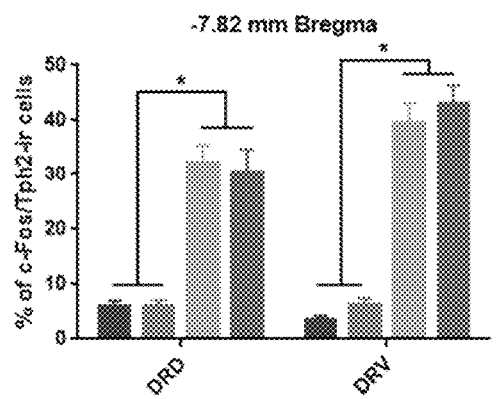
Figure 20B:
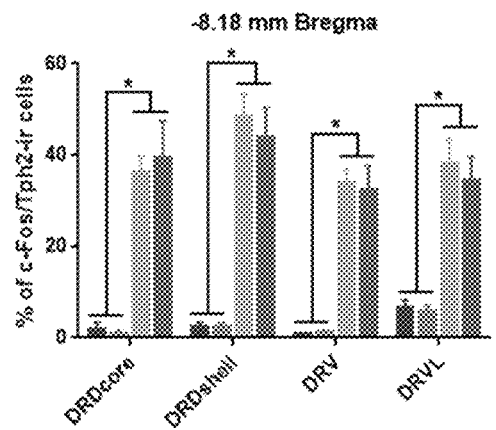
Figure 20C:
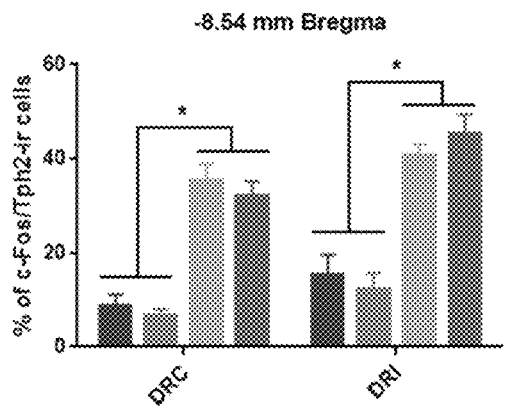
Figure 21:
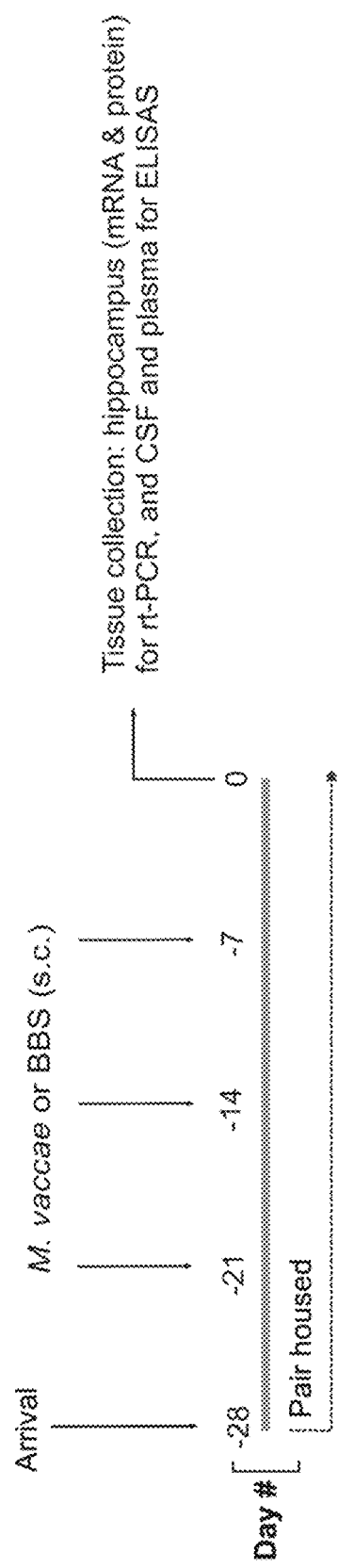

FIG. 20A-C shows c-Fos detection in *M. vaccae* after IS treatments. Data demonstrates percentage of c-Fos/Tph2 positive of total Tph2 positive cells FIG. 21 is a schematic depicting the timing of *M. vaccae* or BBS treatment in male and female rats relative to tissue collection for detection of IL-4.

Figures 22A, 22B:
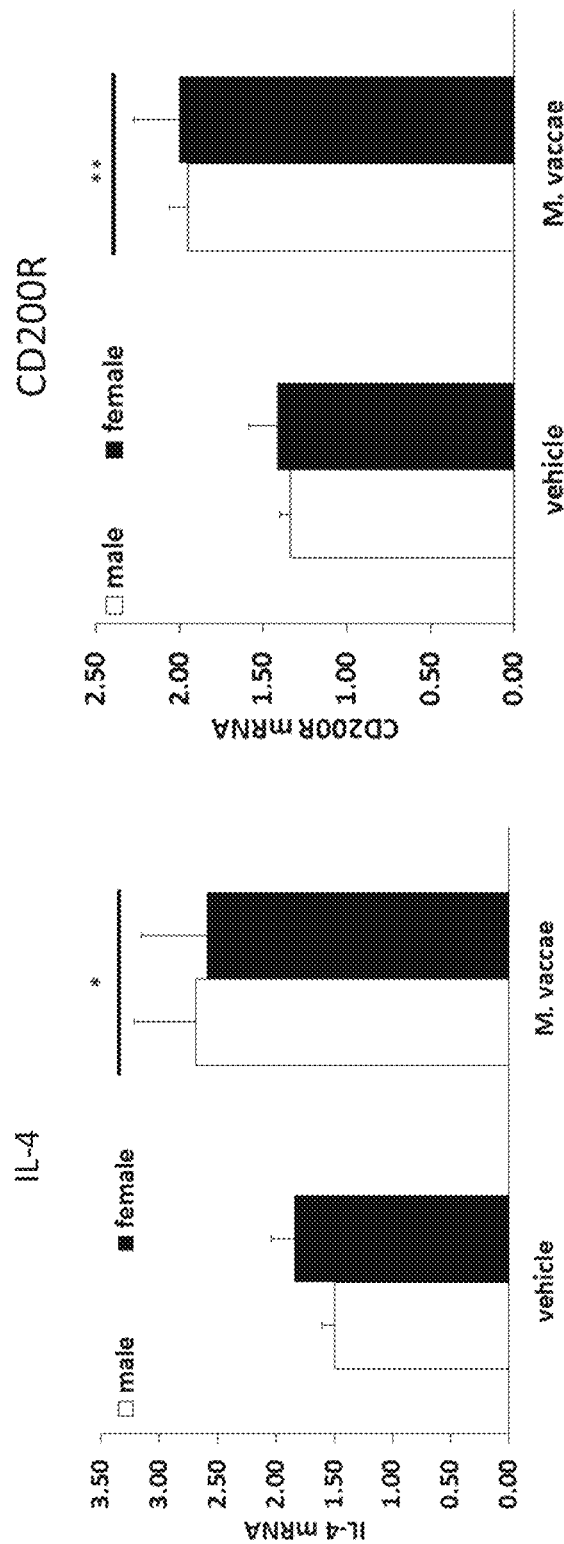

FIG. 22A-B shows experimental data establishing the gender effects on the administration of *M. vaccae* and IL-4 increases in both male and female rats utilizing rt-PCR procedures to measure IL-4 (A) and CD200R (B) mRNA.

Figures 23A, 23B:
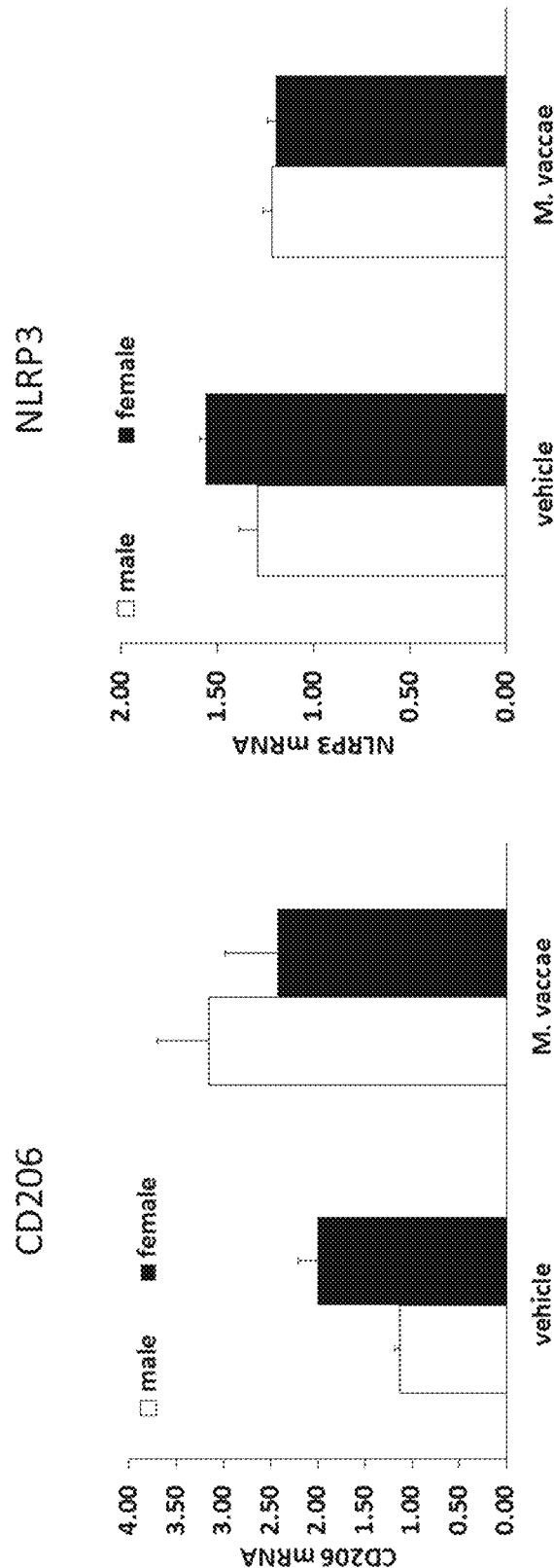

FIG. 23A-B shows experimental data establishing the gender effects on the administration of *M. vaccae* and in both male and female rats utilizing rt-PCR procedures to measure CD206 (A) and NLRP3 (B) mRNA.

Figure 24:
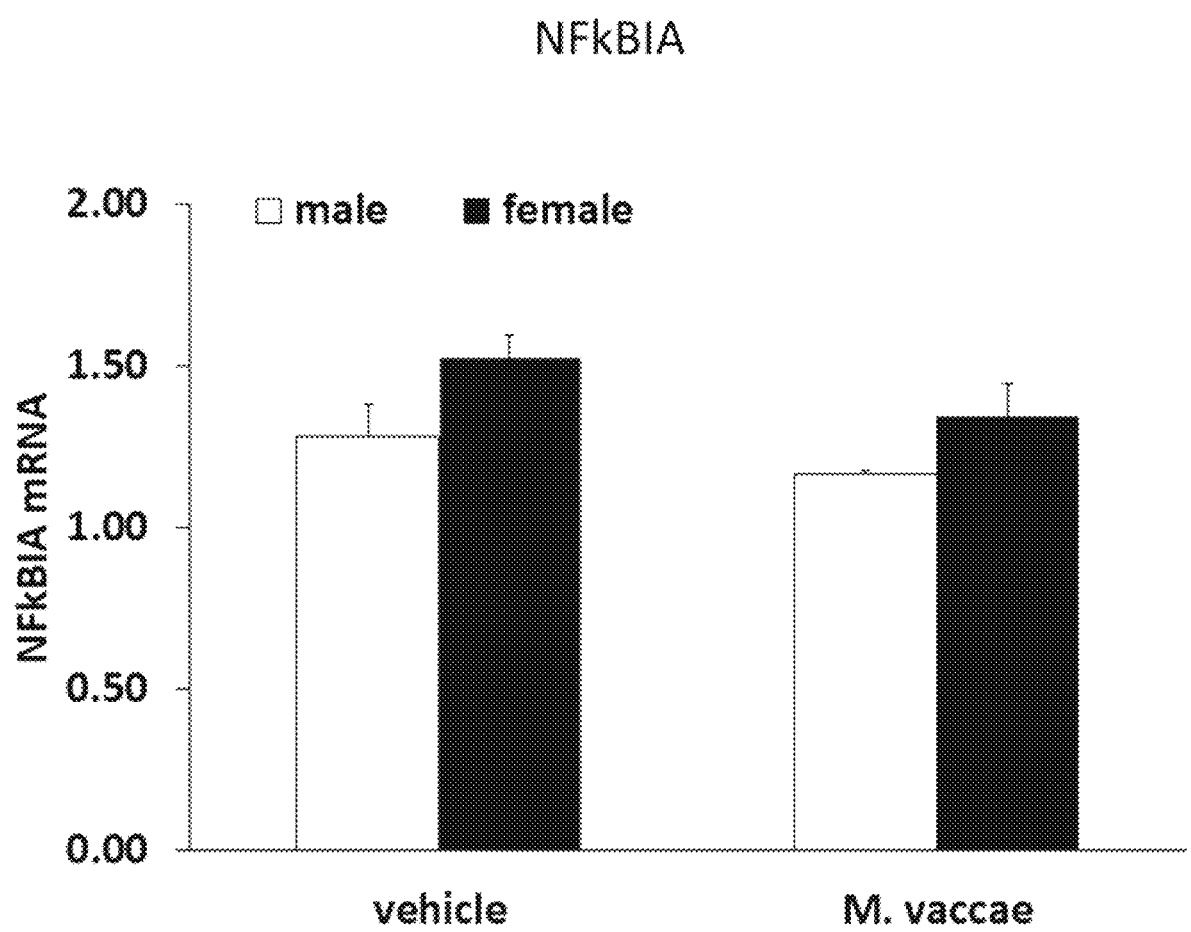

FIG. 24 shows experimental data establishing the gender effects on the administration of *M. vaccae* and in both male and female rats utilizing rt-PCR procedures to measure NFkBIA mRNA.

Figure 25:
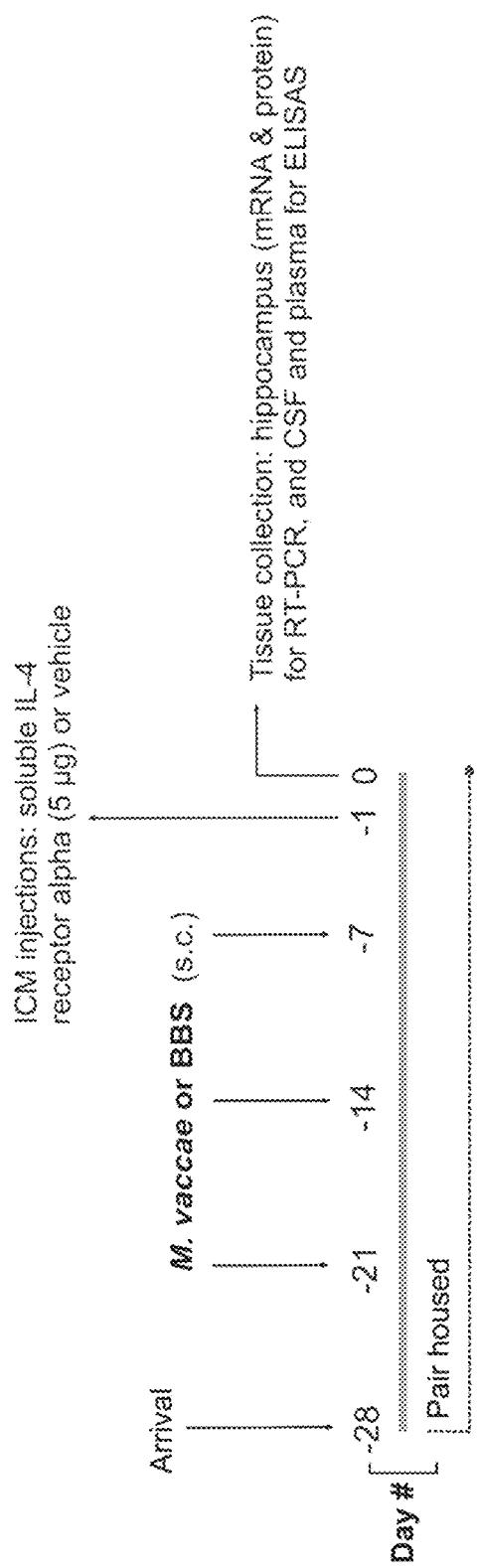

FIG. 25 is a schematic depicting the experimental design configured to develop and validate IL-4 blocking methods in the brain. The schematic depicts the timing of *M. vaccae* or BBS treatment and intra-cisterna magna (ICM) injections containing soluble IL-4 receptor alpha or vehicle followed by tissue collection and analysis.

Figure 26A:
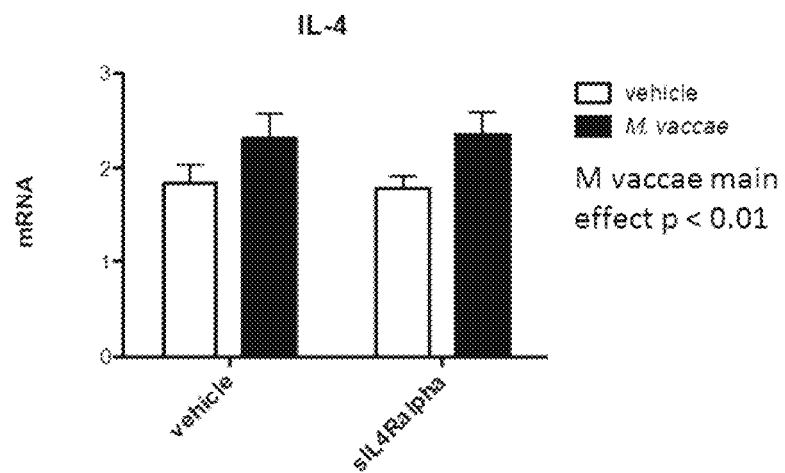
Figure 26B:
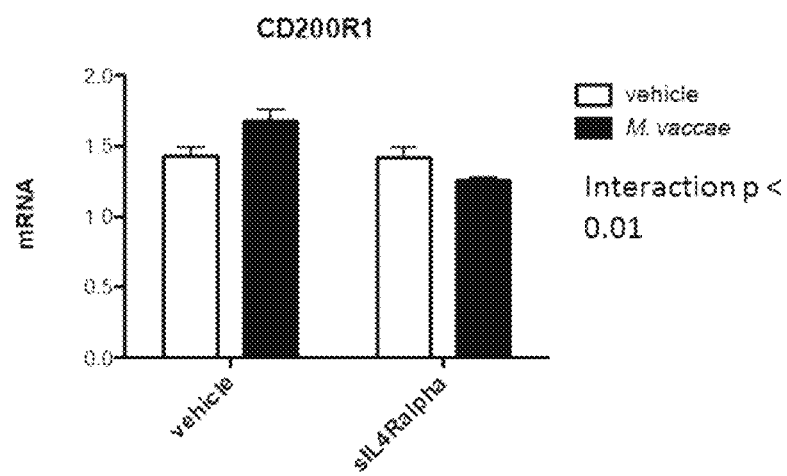
Figure 26C:
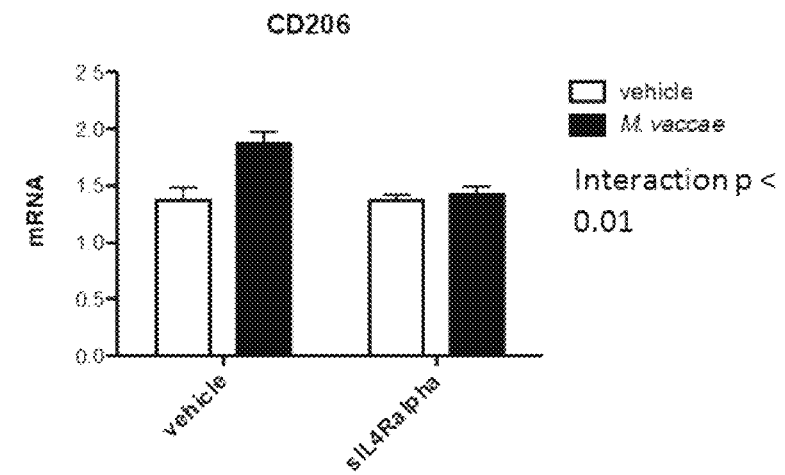

FIG. 26A-C show rtPCR detection in collection tissue samples after ICM injections for IL-4 (A); CD200R1 (B); and CD206 (C).

Figure 27:
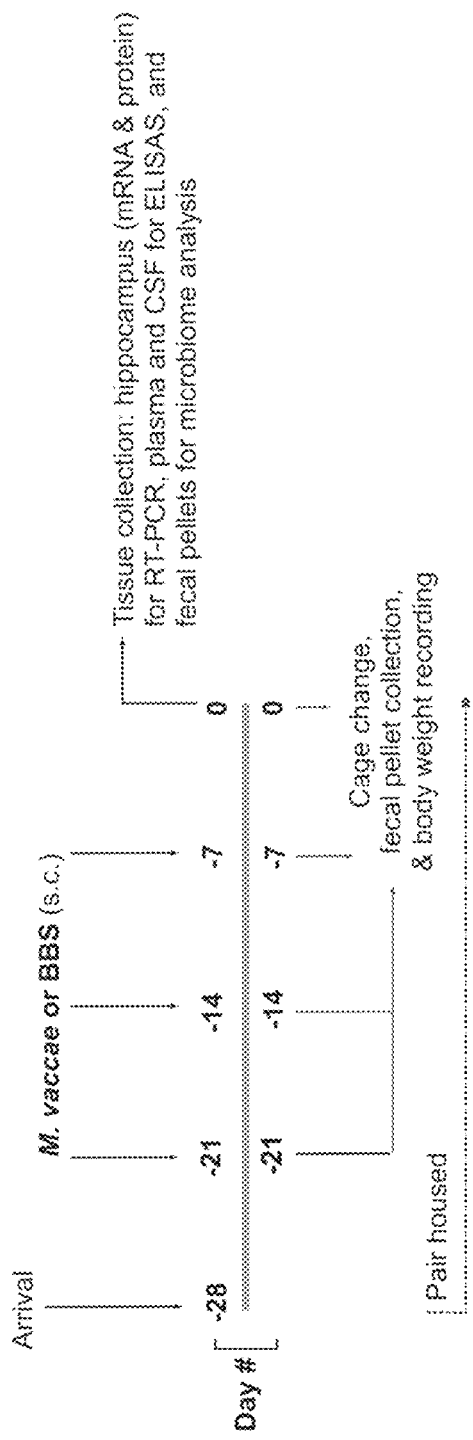

FIG. 27 is a schematic depicting the experimental design configured to evaluate administration of *M. vaccae* vs. oral administration of the probiotic *Lactobacillus rhamnosus* (LGG) followed by tissue collection.

Figure 28:
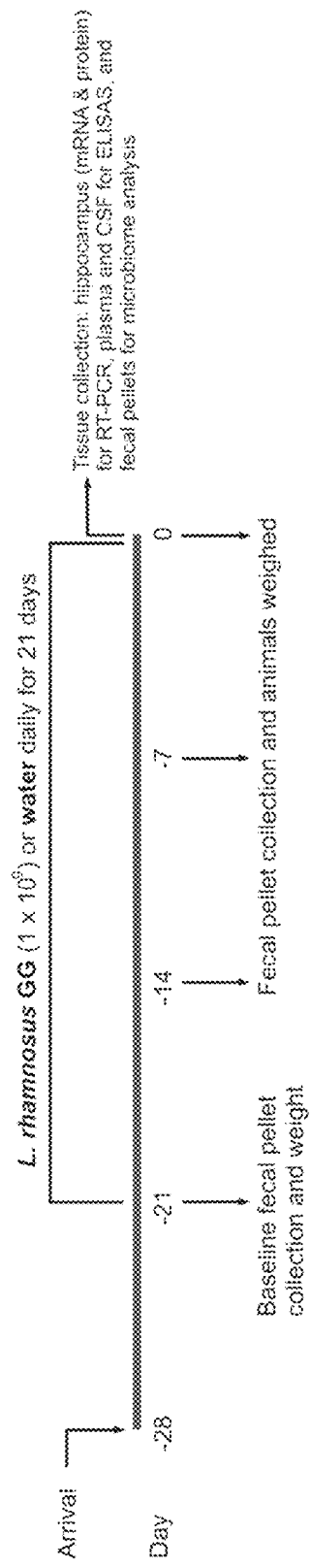

FIG. 28 is a schematic depicting the experimental design configured to evaluate oral administration of the probiotic *Lactobacillus rhamnosus* (LGG) vs. water followed by tissue collection.

Figure 29A:
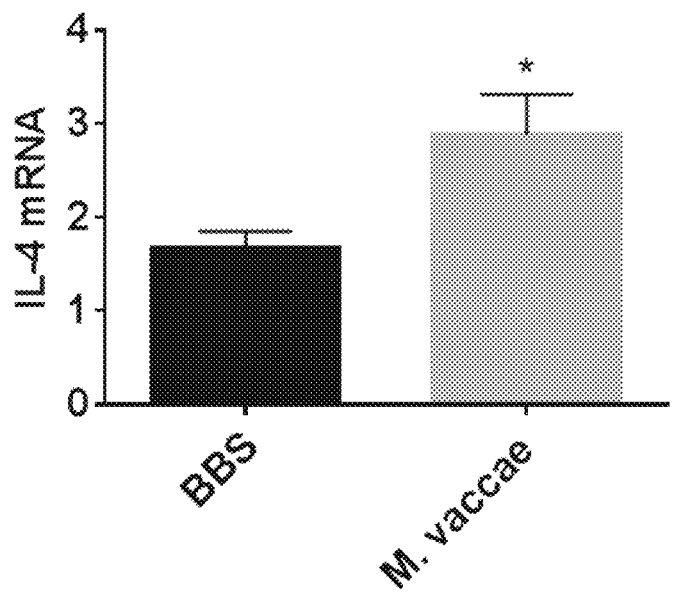
Figure 29B:
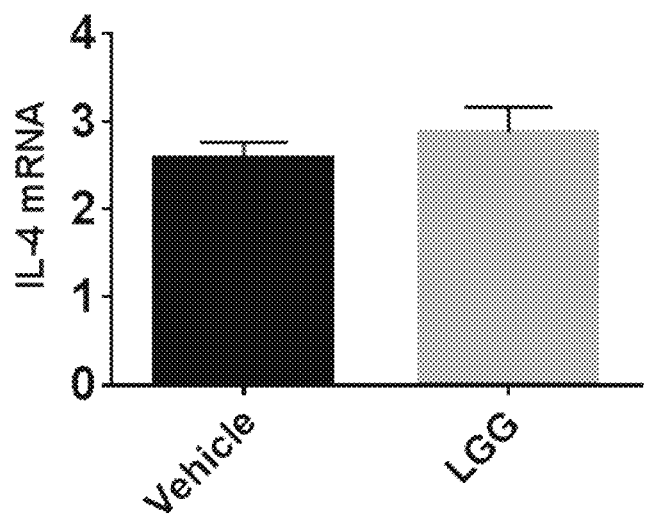

FIG. 29A-B shows experimental data demonstrating increase in IL-4 in rats after administration of *M. vaccae* compared to LGG and BBS and water respectively utilizing rt-PCR procedures to measure IL-4 mRNA.

Figure 30A:
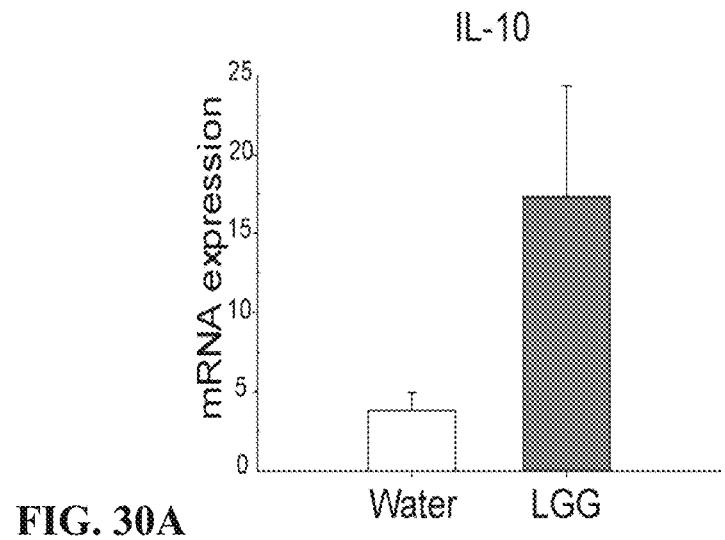
Figure 30B:
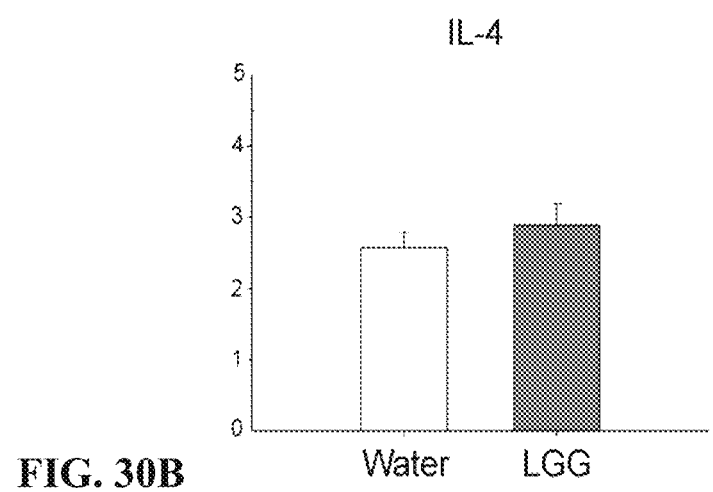
Figure 30C:
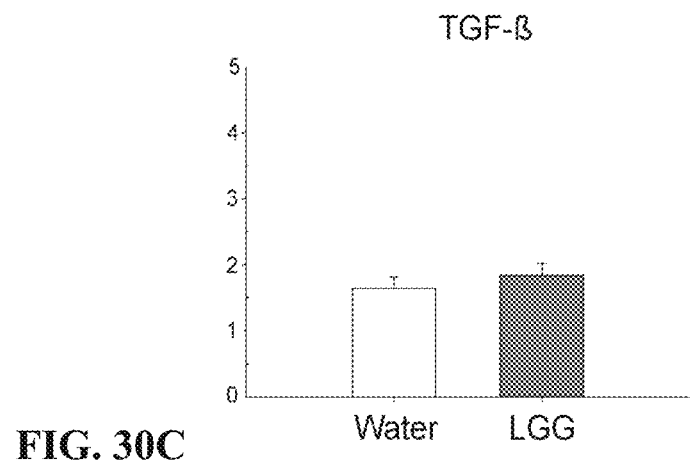
Figure 31A:
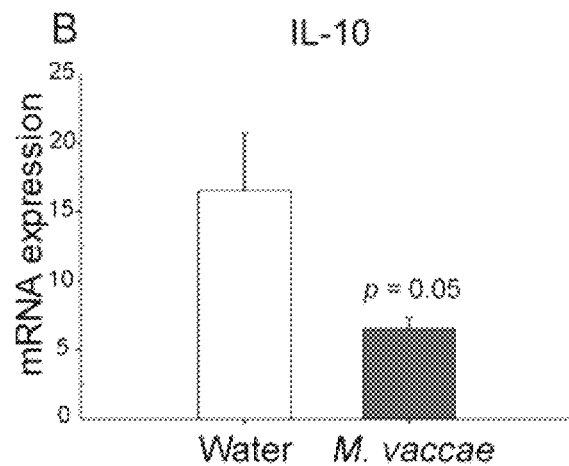
Figure 31B:
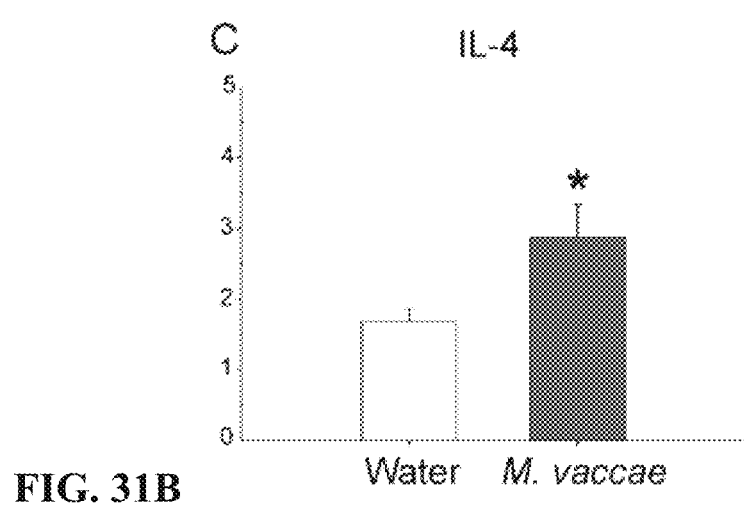
Figure 31C:
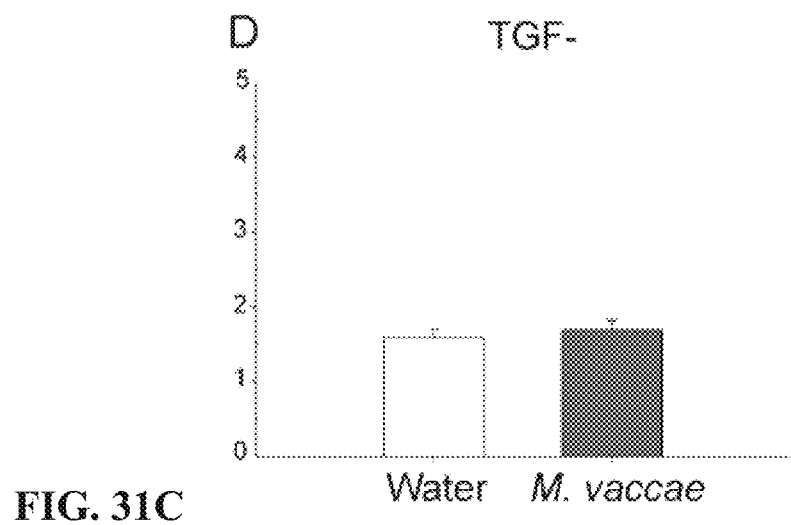

FIG. 30A-C shows levels of anti-inflammatory cytokines, including (A) IL-1β, (B) IL-4, and (C) TGFβ determined by rt:PCR after administration trials of water and LGG according to the schematic of FIG. 31A-C shows levels of anti-inflammatory cytokines, including (A) IL-1β, (B) IL-4, and (C) TGFβ determined by rt:PCR after administration trials of water and LGG.

Figure 32:
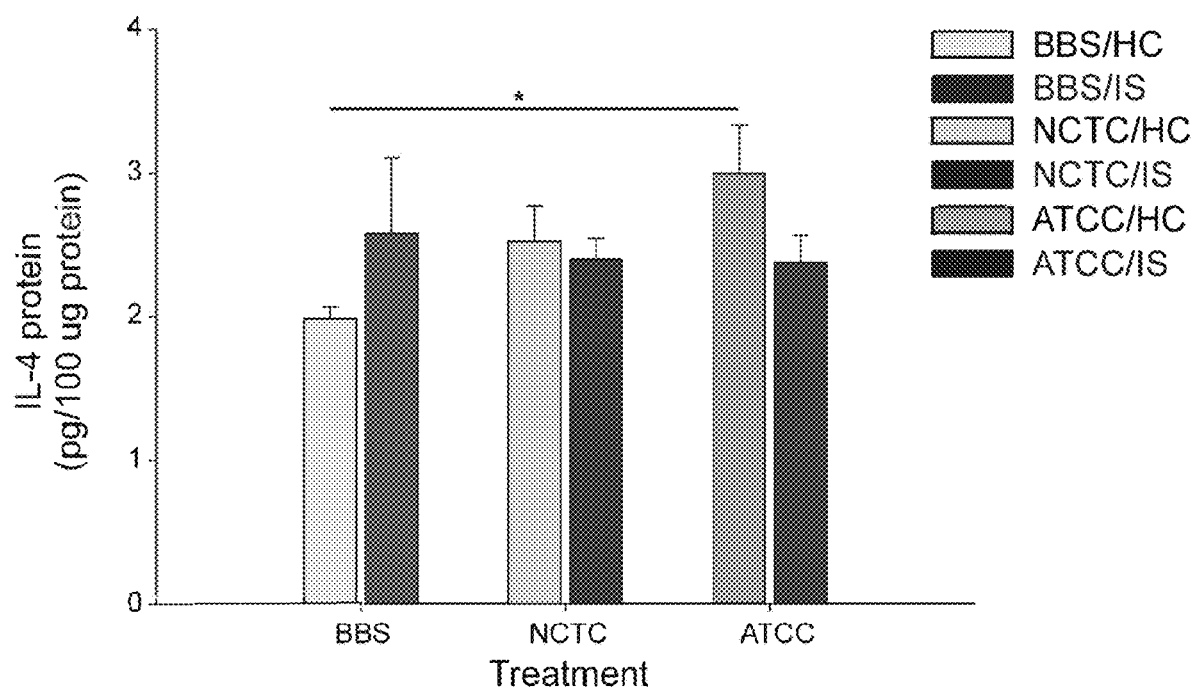

FIG. 32. These data show an increase in IL-4 in the hippocampus after ICM administration of *M. vaccae* (3× weekly injections).

Figure 33:
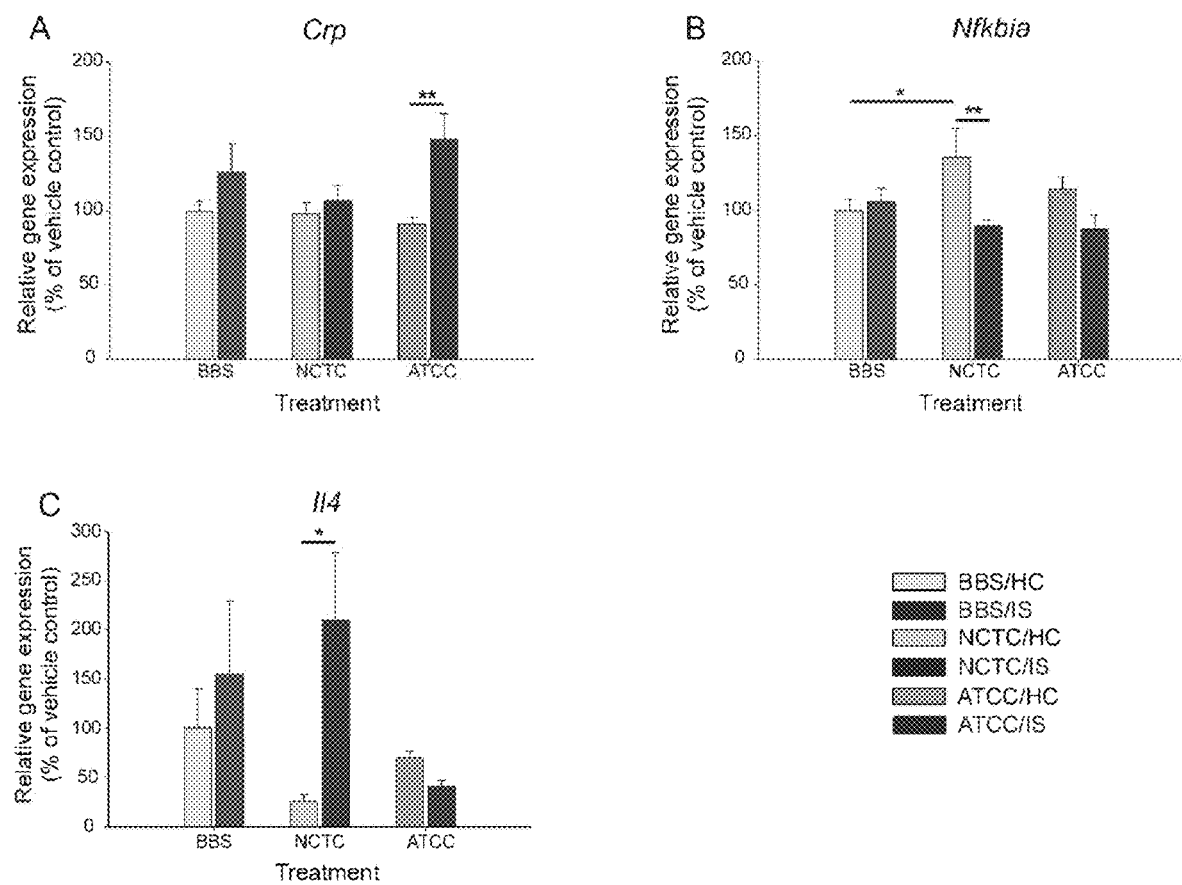

FIG. 33A-C. Effects of immunization with *M. vaccae* NCTC 11659 (NCTC) or *M. vaccae* ATCC 15483 (ATCC) and inescapable tail shock stress (IS) on mRNA expression of immune signaling genes in the liver. Data represent (A) Crp, (B) Nfkbia, and (C) Il4 mRNA expression in the left lobe of the liver. Sample sizes: Crp (BBS/HC, n=8; BBS/IS, n=8; NCTC/HC, n=8; NCTC/IS, n=7; ATCC/HC, n=8; ATCC/IS, n=8); Nfkbia (BBS/HC, n=8; BBS/IS, n=8; NCTC/HC, n=8; NCTC/IS, n=7; ATCC/HC, n=8; ATCC/IS, n=8); Il4 (BBS/HC, n=8; BBS/IS, n=7; NCTC/HC, n=7; NCTC/IS, n=8; ATCC/HC, n=7; ATCC/IS, n=8). Expression of Crp, Nfkbia, and Il4 mRNA were measured using quantitative real-time polymerase chain reaction (RT-qPCR), with beta-actin as a reference. Bars represent the mean+SEM. Post hoc testing was conducted using Fisher's least significant difference (LSD) test. $*p<0.05$, $**p<0.01$. Abbreviations: ATCC, *M. vaccae* ATCC 15483; BBS, borate-buffered saline; Crp, C-reactive protein; HC, home cage control conditions; Il, interleukin; IS, inescapable tail shock; NCTC, *M. vaccae* NCTC 11659; Nfkbia, NF-κB inhibitor α.

DETAILED DESCRIPTION OF THE INVENTION

This disclosure provides methods of utilizing mycobacteria, for the treatment or prevention of neuroinflammation associated with stress, anxiety, and postoperative cognitive dysfunction (POCD).

*M. vaccae* is a saprophytic bacterium found in soil, water, and mud, and is considered an "Old Friend" with potent immunoregulatory effects. *M. vaccae* is available commercially from National Collection of Type Cultures (NCTC), of Public Health England; Bio Elpida, Lyon, France; Anhui Longcom Biologic Pharmacy Co., Ltd.; Immodulon Therapeutics. *M. vaccae* increases induction of Tregs and production of anti-inflammatory cytokines, including IL-1β and TGFβ. Furthermore, immunization with *M. vaccae* in mice prevents development of a PTSD-like syndrome, stress-induced colitis, chemically-induced colitis in a model of inflammatory bowel disease, stress-induced exaggeration of proinflammatory cytokine secretion from freshly isolated and stimulated mesenteric lymph node cells, and anxiety-like behaviors.

As used herein, the terms "patient" and/or "subject" can be used interchangeably. For the avoidance of doubt, the present invention is intended preferably for use in humans, however non-human vertebrate animals (veterinary use) can also be subject to the treatment or preventative therapy. For example, horses and dogs are often used in military or police operations as well as in other instances, such as on racetracks, where they may become exposed to stressful or surgical conditions. The therapy of the invention can therefore be of use to restore performance in such animals.

As used herein, the term "preventing" refers to any manner in which at least one sign, symptom, or symptom cluster of a disease or disorder is beneficially altered so as to prevent or delay the onset, retard the progression, prevent relapse, or ameliorate the symptoms or associated symptoms of the disease or disorder. For example, in anxiety, preventing the disorder can prevent the occurrence of at least one of a sign, symptom, and/or symptom cluster of anxiety. Similarly, in POCD, preventing the disorder can prevent the occurrence of at least one sign, symptom, and/or symptom cluster of PCOD.

The present invention also relates to the treatment of stress, anxiety, or PCOD, or one or more symptoms of stress, anxiety, or PCOD in a subject. Treatment may retard progression, prevent relapse, or ameliorate stress, anxiety, or PCOD, or one or more symptoms of these disorders.

Postoperative cognitive dysfunction or decline (POCD) is an increasingly common phenomenon after major surgery, and older age is a strong preoperative risk factor of POCD. Thus, the incidence of POCD is expected to increase as the population of older surgical patients grows. POCD is associated with impairments in daily functioning, premature departure from the labor market, and dependency on government economic assistance after hospital discharge.

As used herein, POCD refers to problems in thinking and memory after surgery. POCD commonly includes a decline in a variety of neuropsychological domains including memory, executive functioning, and speed of processing. POCD has been defined in a consensus statement as "a spectrum of postoperative central nervous system (CNS) dysfunction, both acute and persistent, including brain death, stroke, subtle neurologic signs and neuropsychological impairment." (Murkin, et al, Annals of Thoracic Surgery 1995; 59:1289-95).

POCD is distinguished from delirium or dementia. Delirium describes an acute confused state featuring disturbances in attention and decreased awareness of the environment, which symptoms fluctuate during the course of the day, and the patient often is disoriented. In addition, hallucinations and inappropriate communication or behavior may be observed in the presence of delirium. In contrast, a typical patient with POCD is oriented but exhibits significant declines from his or her own baseline level of performance on one or more neuropsychological domains. After surgery, changes in cognitive status may present in the form of a frank delirium or POCD, or both. POCD differs from dementia, which describes a chronic, often insidious, decline in cognitive function.

No general consensus has been established thus far regarding the optimum timing of assessments after surgery. In previous studies, cognitive function was measured beginning 1 day to as long as 5 years after surgery.

POCD can be broadly divided into acute, intermediate, and late or long-term changes based on information from previous studies. Specifically, acute POCD has been used to describe cognitive decline detected within one week after surgery, intermediate POCD for changes within 3 months, and long-term POCD for changes 1-2 years following surgery. Early assessments of POCD may capture a different phenomenon than what late assessments of POCD capture, and each are accompanied by a unique set of issues. Surgery related factors may affect test performance in the immediate postoperative period, including acute pain, the use of drugs, nausea, limited mobility, and fatigue. Thus, it has been argued that patients should not be evaluated for POCD until at least one week postoperatively. Recent evidence suggested this delay might be arbitrary, as negative outcomes are associated with POCD detected in the first week after surgery. In a 2008 study of patients undergoing noncardiac surgery, POCD detected at hospital discharge (mean duration of stay, <7 days) was associated with an increased risk of death within the first 3 months after surgery (Monk T G, et al., Anesthesiology 2008; 108:18-30).

Potential precipitating risk factors for POCD have been investigated, and an early ISPOCD study reported that the duration of anesthesia, a second operation, postoperative infections, and pulmonary complications increase the risk of POCD (Moller J, et al., Lancet 1998; 351:857-61). In cardiac surgery, the use of cardiopulmonary bypass has been implicated as one of the precipitating factors. But more recent studies suggest the type of surgery and anesthetic type and management do not appear to influence rates of POCD.

As used herein the phrase "diagnosed with POCD" refers to having a sign, symptom, or symptom cluster indicative of POCD. If the patient has at least one sign, symptom, or symptom cluster of POCD following a surgical procedure, the patient is diagnosed with the disorder. In certain embodiments, a scale is used to measure a sign, symptom, or symptom cluster of POCD, and the disorder is diagnosed on the basis of the measurement using that scale. In certain embodiments, a "score" on a scale is used to diagnose or assess a sign, symptom, or symptom cluster of POCD. In certain embodiments, a "score" can measure at least one of the frequency, intensity, or severity of a sign, symptom, or symptom cluster of POCD.

As used herein, the term "symptom" and "symptoms" refer to subjective indications that characterize a disorder. POCD symptoms include difficulty staying focused on a task, inability to multitask, difficulty finding words and recalling information recently acquired; disturbances of psychomotor dexterity, memory, attention, consciousness, information processing, and sleep-wake cycle, leading to postoperative morbidity and mortality. In more severe cases, POCD symptoms may include a catastrophic loss of cognitive function, with associated increased mortality, risk of prematurely leaving work, and dependence on social welfare.

As used herein, the term "symptom cluster" refers to a set of signs, symptoms, or a set of signs and symptoms, which are grouped together because of their relationship to each other or their simultaneous occurrence.

As used herein, the term "significantly" refers to a set of observations or occurrences that are too closely correlated to be attributed to chance. For example, in certain embodiments, "significantly changes", "significantly reduces", and "significantly increases" refers to alterations or effects that are not likely to be attributed to chance. In certain embodiments, statistical methods can be used to determine whether an observation can be referred to as "significantly" changed, reduced, increased, or altered.

As used herein, the phrase "improving resilience" refers to increasing the ability of a patient to experience stressful or anxiety-inducing events or stimuli without suffering anxiety or stress or with less post-event anxiety or stress symptomatology or disruption of normal activities of daily living. In certain embodiments, improving resilience can, in certain embodiments, reduce at least one of the signs, symptoms, or symptom clusters of stress or anxiety.

Stress or anxiety may manifest as at least one of difficulty falling or staying asleep, irritability or outbursts of anger, difficulty concentrating, hyper-vigilance, exaggerated startle response, and fear from potentially threatening stimuli.

The immunization with the isolated *Mycobacterium* may reduce the difficulty of staying asleep by reducing neuroinflammation associated with anxiety, stress, or POCD.

In certain embodiments the human patient is an adult or "senior" older than 50 years.

In certain embodiments the isolated *Mycobacterium* may prevent at least one sign or symptom of stress or anxiety in the patient, wherein the sign or symptom is selected from disorganized or agitated behavior, problems with pain perception and pain tolerance, headache, difficult falling or staying asleep.

In certain embodiments the isolated *Mycobacterium* reduces the incidence of at least one disorder comorbid with anxiety or stress selected from drug abuse, alcohol abuse, and depression in the patient.

In certain embodiments the isolated *Mycobacterium* is administered to the patient before or immediately after a stressful event or surgical procedure.

In a further embodiment, the isolated *Mycobacterium* prevents and/or reduces low-grade neuroinflammation concomitant with stress, anxiety and POCD. Such low-grade inflammation may be indicated by elevated levels of the alarmin HMGB1, and priming of the microglial response to immune challenge, or decreases in Cd200r1, which may be measured in samples of cerebrospinal fluid.

In one embodiment, administration, as defined herein, includes the administration of the isolated *Mycobacterium* in multiple aliquots and/or doses and/or on separate occasions. Preferably the isolated *Mycobacterium* is administered before and continued to be administered to the patient after a stressful or surgical event occurs. More preferably, the isolated *Mycobacterium* is continued to be administered to the patient after a stressful or surgical event occurs.

In one aspect of the present invention the isolated *Mycobacterium* comprises a heat-killed *Mycobacterium*. Preferred mycobacterial species for use in the methods of this disclosure include *M. vaccae*. A particularly preferred mycobacterial species is *M. vaccae* strain NCTC 11659 (commercially available from Bio Elpida).

Preferably, the heat-killed *M. vaccae* is non-pathogenic. The amount of isolated *Mycobacterium* administered to the patient is sufficient to elicit a protective neuroimmune response in the patient such that it prevents at least one sign or symptom of the impaired cognitive function, anxiety, stress, or POCD associated with neuroinflammation in the patient, wherein the sign or symptom is selected from disorganized or agitated behavior, problems with pain perception and pain tolerance, headache, difficult falling or staying asleep, and frightening dreams. Preferably, administration of an effective amount of isolated *M. vaccae* is one which prevents at least one symptom cluster of the impaired cognitive function, stress, anxiety or POCD in the patient, wherein the symptom cluster is selected from re-experiencing/intrusion, avoidance/numbing, and hyper-arousal.

In certain embodiments of the invention, it is preferable that a particular dosage of isolated *M. vaccae* be administered to a subject. Thus, in certain embodiments of the invention, there is provided a composition comprising the effective amount of heat-killed *Mycobacterium M. vaccae* for use in the methods of this disclosure, which typically may be from $10'$ to $10^{11}$ organisms, preferably from $10^4$ to $10^{10}$ organisms, more preferably from $10^6$ to $10^{10}$ organisms, and even more preferably from $10^6$ to $10^9$ organisms per unit dose. The effective amount of heat-killed *M. vaccae* for use in the methods of this disclosure is from $10^7$ to $10^9$ cells or organisms. Typically, the composition according to the present invention may be administered at a dose of from $10^8$ to $10^9$ cells for human and animal use.

In a further embodiment, the administration of the isolated *M. vaccae* produces a neuro-immunomodulatory effect, wherein an anti-inflammatory milieu is induced in the brain of a subject.

The term "combination" as used throughout the specification, is meant to encompass the administration of the therapeutic agents in the same or separate pharmaceutical formulations, and at the same time or at different times. Thus, an isolated *M. vaccae* and the pharmaceutical agent may be provided as separate medicaments for administration at the same time or at different times. Preferably, an isolated *Mycobacterium* and pharmaceutical agent are provided as separate medicaments for administration at different times. When administered separately and at different times, either an isolated *Mycobacterium* or pharmaceutical agent may be administered first; however, it is preferable to administer an isolated *Mycobacterium* followed by pharmaceutical agent. In addition, both drugs can be administered in the same day or at different days, and they can be administered using the same schedule or at different schedules during the treatment cycle.

Preferably, the isolated *Mycobacterium* is administered to the patient before any anticipated stressful or surgical event.

Dose delays and/or dose reductions and schedule adjustments are performed as needed depending on individual patient tolerance to treatments.

Before any anticipated stressful or surgical event, effective amounts of *M. vaccae* may be administered in multiple (repeat) doses, for example two or more, three or more, four or more, five or more, ten or more, or twenty or more repeat doses, at intervals of about 2 weeks, or about 4 weeks or about 8 weeks.

The isolated *Mycobacterium* may be administered to the patient via the parenteral, oral, sublingual, nasal or pulmonary route. In a preferred embodiment, the isolated *Mycobacterium M. vaccae* is administered via a parenteral route selected from subcutaneous, intradermal, subdermal, intraperitoneal, intravenous and intravesicular injection. More preferably, administration by the parenteral route does not comprise injection of mycobacterial cell wall extract.

In another preferred embodiment, the isolated *Mycobacterium* is administered orally, including by suspension, tablets and the like. Liquid formulations could be administered by inhalation of lyophilized or aerosolized microcapsules. Additional pharmaceutical vehicles could be used to control the duration of action of the preparation. They could be entrapped in microcapsules prepared by coacervation techniques or by interfacial polymerization (hydroxymethylcellulose or gelatin microcapsules) in colloidal drug delivery systems (for example, liposomes, albumin microspheres, micro-emulsions, nanoparticles and nanocapsules) or in macro-emulsions. Excipients, for example, salts, various bulking agents, additional buffering agents, chelating agents, antioxidants, cosolvents and the like can be included in the final formulation.

A suitable dosage schedule according to this embodiment includes administration of the isolated *Mycobacterium* followed by further doses of the isolated *Mycobacterium* 2 weeks later and continuing every 2 weeks for the next 3 doses followed by 4 weeks without treatment. Thereafter, patients may receive the isolated *Mycobacterium* every 4 weeks for up to 12 months or longer following the first dose given. Alternatively, dosing may involve weekly administration following the priming or initial dose.

The patient who is to be exposed to a stressful or surgical event may do so simultaneously, separately or sequentially with administration of the isolated *Mycobacterium*. Preferably the isolated *Mycobacterium* is administered to the patient prior to the anticipated stressful or surgical event. More specifically, the isolated *Mycobacterium* may be administered to the patient between about 4 weeks and 1 week prior to any anticipated stressful or surgical event. Preferably, the isolated *Mycobacterium* may be administered as one or more aliquots each containing an effective amount of the isolated *Mycobacterium* which may be administered at one or more time intervals between 4 weeks and 1 week prior to any anticipated stressful or surgical event. Even more preferably, the isolated *Mycobacterium* may be administered as one or more aliquots each containing an effective amount of the isolated *Mycobacterium* which may be administered at one or more time intervals between 4 weeks and 1 week before any anticipated stressful or surgical event and/or the isolated *Mycobacterium* may be administered, and repeated on at least about 2, 4, 6, 8, 10, 12, 15, 20 or more occasions before and/or after any anticipated stressful or surgical event.

In one embodiment of the present invention, the isolated *Mycobacterium* may be in the form of a medicament administered to the patient in a dosage form and/or in a schedule as set out in the Examples of this disclosure.

The effective amount of the isolated *Mycobacterium* may be administered as a single dose. Alternatively, the effective amount of the isolated *Mycobacterium* may be administered in multiple (repeat) doses, for example two or more, three or more, four or more, five or more, ten or more, or twenty or more repeat doses. Preferably, the isolated *Mycobacterium* is administered between about 4 weeks and 1 day prior to an anticipated stressful or surgical event, more preferably between about 4 weeks and 1 week, or about between 3 weeks and 1 week, or about between 3 weeks and 2 weeks. Administration may be presented in single or multiple doses.

The isolated *Mycobacterium* may be lyophilized and formulated for re-suspension prior to administration. However, in other cases, the mycobacteria are suspended in a volume of a pharmaceutically acceptable liquid. In some of the most preferred embodiments there is provided a container comprising a single unit dose of mycobacteria suspended in pharmaceutically acceptable carrier wherein the unit dose comprises about $1 \times 10^6$ to about $1 \times 10^{10}$ mycobacteria. In some very specific embodiments, the liquid comprising suspended mycobacteria is provided in a volume of between about 0.1 ml and 10 ml, or about 0.5 ml and 2 ml. The composition comprising the Mycobacteria may be frozen. The foregoing compositions provide ideal units for applications described herein.

Embodiments discussed in the context of a methods and/or composition of the invention may be employed with respect to any other method or composition described herein. Thus, an embodiment pertaining to one method or composition may be applied to other methods and compositions of the invention as well.

In some cases, attenuated mycobacteria is administered to specific sites on or in a subject. For example, the mycobacterial compositions may be administered into the central nervous system, such as administration to the brain or spinal cord. Alternatively, sites of administration of a mycobacterial composition may be near the posterior cervical, tonsillar, axillary, inguinal, anterior cervical, sub-mandibular, sub mental or superclavicular lymph nodes. Such sites of administration may be on the right side, on the left side, or on both sides of the body.

A dosage of mycobacteria may be administered to a subject by intradermal injection.

In some further embodiments of the invention, methods of the invention involve the administration of 2, 3, 4, 5, 6, 7, 8, 9, 10 or more doses of mycobacteria separated by a period of one day or more. In certain preferred embodiments such separate doses will be separated by several days, one week, two weeks, one month or more. For example, methods according to the invention may comprise administering 1 to 5 doses of mycobacteria over a period of three weeks or more. In yet further embodiments, methods of the invention comprise administering 1 to 5, 1 to 4, 1 to 3, 1 to 2 or 2 doses of mycobacteria over a period of about three weeks. Each dose administered may be the same or different dosage relative to a previous or subsequent dose administration. For example, in certain cases, it is preferred that a dosage of mycobacteria is lower than any dosage that was previously administered. Thus, in some specific cases, a dose of mycobacteria will be administered at about half of the dosage that was administered in any previous treatment. Such methods may be preferred in certain instances where the subject's immune response to the mycobacteria is greater during subsequent therapies. Thus, in certain cases, the isolated *Mycobacterium* may be administered a minimal number of times for example, in less than 10, 9, 8, 7, 6, 5, 4, 3 or fewer separate dosage administrations. In some cases, the mycobacterial composition is administered twice.

Mycobacterial compositions according to the invention will comprise an effective amount of mycobacteria typically dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that parenteral preparations should meet sterility, pyrogenicity, general safety and purity standards. A specific example of a pharmacologically acceptable carrier as described herein is borate buffer saline.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

In a preferred embodiment, the isolated *Mycobacterium* is administered via a parenteral route selected from subcutaneous, intradermal, subdermal, intraperitoneal, intravenous, intravesicular injection or orally. Intradermal injection enables delivery of an entire proportion of the mycobacterial composition to a layer of the dermis that is accessible to immune surveillance and thus capable of electing appropriate immune response at local lymph nodes.

The invention is further described with reference to the following non-limiting Examples.

EXAMPLES

Example 1: Aging is a Major Risk Factor for Developing Postoperative Cognitive Dysfunction (POCD)

The following materials and methods were used to conduct the experiments described in this Example:

Animals: Adult (3 months) and aged (24 months) male F344XBN F1 rats were used in these experiments. Rats of this age and strain were selected to study healthy, non-neurodegenerative aging (these rats live for >30 mos). Rats were received from NIA and pair-housed (52 cm L×30 cm W×21 cm H) with an age-matched conspecific. Food and water were available ad libitum and rats were maintained at an ambient temperature of 22±2° C. on a 12:12 light cycle with lights on at 0700. Upon arrival, rats were acclimated for 7+ days prior to any experimental manipulation.

Experiment 1: Does *M. vaccae* immunization protect aged rats against surgery-induced memory impairments? Adult and aged rats (n=6/group) received three subcutaneous injections of *M. vaccae* or vehicle spaced one week apart (i.e., one injection per week for three weeks). Five days following the final injection of *M. vaccae*, rats underwent a laparotomy or sham surgery. Three days post-surgery, rats received a contextual fear conditioning pre-exposure paradigm, to evaluate hippocampal dependent memory. The pre-exposure paradigm separates the construction of the conjunctive representation of the conditioning context from the association of that representation with the shock. This behavioral procedure allows for detection of memory impairments more selective to the hippocampus than does a standard fear-conditioning paradigm. On the first day of the paradigm (3 days post-laparotomy), rats were placed in a novel clear plastic conditioning chamber (26 length×21 width×24 height cm) with a removable floor of stainless steel rods (1.5 mm diameter) that was placed inside a white ice chest that was open to the front. Rats were exposed to the context six times over the course of 6 h during the light phase. The duration of the first context exposure was 5 min and subsequent exposures lasted 40 sec. Three days later, rats were placed in the conditioning context and immediately received a 2 sec 1.5 mA shock (in context for <5 sec). 24 h following the immediate shock, animals were placed back into the conditioning context or a control context and freezing behavior was assessed, as an index of contextual memory, over a 6 min period. Freezing behavior was scored by a condition-blind observer. Twenty-four h following fear conditioning testing, tissue was collected. This experiment is outlined in FIG. 1A.

Experiment 2: Does *M. vaccae* immunization shift the inflammatory profile of aged rats' post-surgery? Adult and aged rats were immunized with *M. vaccae* or vehicle (3 subcutaneous injections, once per week). Five days following the final injection of *M. vaccae*, rats underwent laparotomy or sham surgery (n=6-7 per group). Three days post-surgery, hippocampal tissue was collected following a PBS perfusion. This time-point post-surgery was selected for assessment of inflammatory mediators because it corresponds to the time post-surgery when conditioning to the context occurred in Experiment 1. Surgery-induced inflammatory mediators can interfere with subsequent memory consolidation.

Experiment 3: Can *M. vaccae* immunization reduce inflammatory priming in microglia isolated from aged rats? Adult and aged rats were immunized with *M. vaccae* or vehicle (3 subcutaneous injections, once per week). Five days following the final injection, hippocampal tissue was collected following a PBS perfusion. Highly pure microglia were isolated (see section 2.7.) from whole hippocampus and stimulated ex vivo with lipopolysaccharide (LPS) for 2 h, which elicits a pro-inflammatory immune response in a concentration-dependent manner. *M. vaccae* preparation and delivery: Rats were treated with a heat-killed *M. vaccae* suspension as previously described. Rats received either subcutaneous injections of 0.1 mg whole heat killed *M. vaccae* suspension (10 mg/ml sterile stock solution diluted to 1 mg/ml with sterile borate buffered saline; NCTC 11659 strain, batch ENG 1, provided by Bio Elpida, Lyon, France) or vehicle (sterile borate-buffered saline). Rats received three injections, each spaced 1 week apart (see experimental outline in FIG. 1A). No adverse physiological or behavioral consequences of *M. vaccae* were observed: there were no overt signs of sickness behavior and *M. vaccae* did not affect weight gain in adult or aged rats.

Laparotomy procedure: This subcostal laparotomy procedure was developed to model human abdominal exploratory surgery by Martin et al and has previously been used in our laboratory. The surgery was performed under aseptic conditions. Rats were anesthetized with halothane anesthesia, the abdominal region was shaved, and the surgical site was cleaned with 70% EtOH followed by surgical scrub. A 3-cm vertical incision was made through the skin, muscle wall, and abdominal wall approximately 0.5 cm below the lower right rib. The surgical opening and viscera were then manipulated. Approximately 10 cm of intestine was exteriorized and vigorously rubbed for 30 sec. The intestines were then placed back into the rat peritoneal cavity and the muscle and abdominal wall were sutured separately using sterile chromic gut sutures (3-0, PS-2, Ethicon). The skin was closed using reflex clips (9 mm, WPI) and a triple antibiotic ointment was applied (CVS). For the sham procedure, rats were anesthetized, shaved, and prepped in the same manner as laparotomy rats, but no incision was made. Sham and laparotomy procedures occurred in parallel: the halothane anesthesia delivery line was bi-furcated such that a sham rat and laparotomy rat were maintained on the same concentration of anesthesia and exposed to anesthesia for the same duration (~25 min).

Tissue and blood collection: 10 Animals were given a lethal intraperitoneal injection of sodium pentobarbital (Fatal-plus; 150 mg/kg). After rats were completely unresponsive (as assessed by pedal reflex), they were transcardially perfused with ice-cold phosphate buffered saline (0.9% saline) for 3 min to remove peripheral immune leukocytes from the central nervous system (CNS) vasculature. Brains were rapidly extracted, placed on ice, and the hippocampus was dissected out. Hippocampus was collected given that this brain region is particularly vulnerable to age-associated neuroinflammatory priming. For experiments involving measurement of in vivo cytokine mRNA expression, hippocampus was flash frozen in liquid nitrogen and stored at −80° C. For experiments involving ex vivo LPS stimulation of isolated hippocampal microglia, hippocampal microglia were immediately isolated. ELISA: Hippocampal samples were sonicated on ice using a tissue extraction reagent (Invitrogen) supplemented with protease inhibitor cocktail (Sigma-Aldrich). Homogenates were centrifuged (14,000×g for 10 min at 4° C.) and supernatants collected and stored at −20° C. Total protein was quantified using a Bradford assay. An ELISA for rat IL-1β (R&D systems) was run according to the manufacturer's instructions and IL-1β protein levels normalized to total protein (pg IL-1β/100 µg total protein).

Microglia isolations and ex vivo treatments: Hippocampal microglia were isolated using a Percoll density gradient as previously described. Rats were PBS-perfused, brains were removed, and the hippocampus was dissected out on ice. The hippocampus was homogenized in 3 mL of 0.2% glucose in 1× Dulbecco's Phosphate Buffered Saline (DPBS). The hippocampal homogenate was passed through a 40-µm filter and the filter was rinsed with an additional 2 mL of DPBS. Cells were pelleted in 5-ml falcon tubes at 1000 g for 10 min at 22° C. and then the supernatant was poured off. A Percoll (GE Healthcare) gradient was created by re-suspending the pellet in 2 mL of 70% isotonic Percoll (isotonic Percoll consists of 10:1 Percoll:10×DPBS; 100% isotonic Percoll is then diluted with 1×DPBS), followed by a layer of 2 mL 40% isotonic Percoll and topped with 1 mL DPBS. The gradient was spun at 1200 g for 30 min at 22° C. with no acceleration or brake. Myelin debris was removed and then microglia were extracted from the 40%/70% interface. Microglia were washed in DPBS and pelleted at 1000 g for 10 min at 22° C. Microglia were resuspended in media (filtered Dulbecco's Modified Eagle Medium (DMEM (Gibco)+10% fetal bovine serum (FBS)) and microglia concentration and viability were determined by trypan blue exclusion. Microglia were plated at a density of 8,000 cells/100 µL in a 96-well v-bottom plate. To assess microglia cytokine responsiveness, cells were challenged ex vivo with lipopolysaccharide (LPS; *E. coli* serotype 0111:B4; Sigma-Aldrich) at a concentration of 10 or 100 ng/mL or media alone at 37° C., 5% $CO_2$.

The LPS concentrations, incubation time, and cell density were based on previous publications from our laboratory. After 2 h, plates were centrifuged at 1000 g for 10 min at 4° C. to pellet cells and wells were aspirated. Cells were washed with 1×DPBS, centrifuged at 1000 g for 10 min at 4° C., and RNA was isolated using a CellsDirect Kit (Invitrogen) according to the manufacturer's instructions.

qPCR: Rat primers were previously designed using Genbank at the National Center for Biotechnology Information (NCBI), the Operon Oligo Analysis Tool, and the Basic Local Alignment Search Tool at NCBI and obtained from Invitrogen. Primers were designed to span exon/exon boundaries and thus exclude amplification of genomic DNA. Primer specificity was verified by melt curve analysis. Primers included:

```
Arg1
(F: CTACCTGCTGGGAAGGAAG (SEQ ID NO. 3) and R:
GTCCTGAAAGTAGCCCTGTC) (SEQ ID NO. 4), β-actin (F: TTCCTTCCTGGGTATGGAAT (SEQ ID NO. 1)
and R:
GAGGAGCAATGATCTTGATC) (SEQ ID NO. 2), IL-1β (F: CCTTGTGCAAGTGTCTGAAG (SEQ ID NO. 17)
and R:
GGGCTTGGAAGCAATCCTTA) (SEQ ID NO. 18), IL-4 (F: CAACAAGGAACACCACGGAG (SEQ ID NO. 41)
and R:
GGTGCAGCTTCTCAGTGAGT) (SEQ ID NO. 42)
IL-6 (F: AGAAAAGAGTTGTGCAATGGCA (SEQ ID NO. 21)
and R:
GGCAAATTTCCTGGTTATATCC) (SEQ ID NO. 22), IL-10 (F: GGACTTTAAGGGTTACTTGGG (SEQ ID NO. 23)
and R:
AGAAATCGATGACAGCGTCG) (SEQ ID NO. 24), CD200 (F: CTCTCTATGTACAGCCCATAG (SEQ ID NO. 9)
and R:
GGGAGTGACTCTCAGTACTAT) (SEQ ID NO. 10), CD206 (F: AATGGGTGCCTCCCTGGTTT (SEQ ID NO. 43)
and R:
AGGGTCACCCGTTTTCCAGT) (SEQ ID NO. 44), and MHCII (F: AGCACTGGGAGTTTGAAGAG (SEQ ID NO. 45)
and R:
AAGCCATCACCTCCTGGTAT) (SEQ ID NO. 46).
```

RNA was extracted from hippocampal homogenates using TRIZOL reagent and 2 µg of RNA was reversed transcribed to cDNA using Superscript II (Invitrogen) according to the manufacturer's instructions. RNA was isolated from microglia and reversed transcribed to cDNA using SuperScript III CellsDirect cDNA Synthesis System (Invitrogen). PCR amplification of cDNA was performed using the Quantitect SYBR Green PCR Kit (Qiagen) with a MyiQ Single-Color Real-Time PCR Detection System (Bio-Rad). Gene expression was run in duplicate and analyzed with the 2^ΔΔCt method relative to β-actin. There were no group differences in β-actin expression.

Statistical analysis: All data are presented as mean±standard error of the mean (SEM). Data were analyzed with StatView and Prism 7 (GraphPad Software). Data were analyzed using analysis of variance (ANOVA) with age, surgery, and M. vaccae treatment as the between-subjects' factors (2×2×2). F values are reported for each ANOVA and serve as the criteria for post hoc analysis (Tukey's HSD). Threshold for statistical significance was set at two-tailed $p<0.05$.

The inventors tested whether exposure to a microorganism, Mycobacterium vaccae NCTC11659 (M. vaccae), with immunoregulatory and anti-inflammatory properties, can ameliorate age-associated neuroinflammatory priming.

Example 2: M. vaccae Immunization Prevented Memory Deficits in Aged Rats Following Surgery Young (3 months) and aged (24 months) rats received three subcutaneous injections of M. vaccae or vehicle, each injection spaced 7 days apart (experiment outlined in FIG. 1A). Five days following the final injection of M. vaccae rats underwent a laparotomy or sham procedure. After a 3-day recovery period, rats were tested in a pre-exposure fear conditioning paradigm. Freezing behavior is used as an index of memory in this task as freezing is a dominant fear response in rats. There were no differences in baseline freezing (prior to conditioning) between the groups (data not shown, $p>0.05$). During the testing portion of the fear conditioning paradigm, there was a three-way interaction for freezing behavior in the conditioned context (age×M. vaccae× surgery: $F_{1,36}=5.7$, $p<0.05$, FIG. 1B). In agreement with previous findings, aged vehicle-treated rats that underwent a laparotomy procedure had reduced freezing in the context where they previously received a foot shock (conditioned context), which is suggestive of an impairment in memory (post hoc, $p<0.05$). Indeed, postoperative aged rats showed a 25% reduction in freezing compared to aged rats that underwent the sham procedure; however, this freezing deficit was completely abolished by M. vaccae treatment. Aged rats that were immunized with M. vaccae prior to a laparotomy procedure displayed comparable freezing to aged sham animals (post hoc, $p>0.05$). There were no differences in freezing behavior in adult rats, or between any of the groups in the novel context (FIGS. 1B and 1C). Thus, postoperative memory deficits in aged rats were completely ameliorated by M. vaccae immunization.

Example 3: M. vaccae Immunization Altered Neuroinflammatory Responses in Aged Rats that Underwent a Laparotomy Young and aged rats received three subcutaneous injections of M. vaccae or vehicle, each injection spaced seven days apart. Five days following the final injection with M. vaccae, rats underwent a laparotomy or sham procedure and tissue was collected three days later (FIG. 2A). Previous work indicates that age-related POCD in rats is dependent on increases in hippocampal IL-1β. In agreement with these findings, aged rats that received a laparotomy procedure had elevated IL-1β mRNA expression (age×surgery: $F_{1,45}=5.3$, $p<0.05$; FIG. 2B). The three-way interaction of age×surgery×M. vaccae was not statistically significant ($p=0.1$); however, treatment with M. vaccae, reduced IL-1β mRNA (main effect of M. vaccae: $F_{1,45}=6.5$, $p<0.05$). Hippocampal IL-1 protein was regulated in a similar manner as IL-1β mRNA (FIG. 2C). Aged vehicle-treated rats that underwent a laparotomy procedure had enhanced IL-1β protein and M. vaccae immunization protected against the increase in IL-1β. Age- and surgery-induced elevations in NFKBIA mRNA expression (age: $F_{1,45}=13.9$, surgery: $F_{1,45}=8.8$, $p<0.05$) were also ameliorated by M. vaccae pre-treatment (M. vaccae: $F_{1,45}=4.3$, $p<0.05$; FIG. 2C).

M. vaccae can buffer against the pro-inflammatory effects of stress by upregulating anti-inflammatory pathway genes in the periphery (IL-10 and transforming growth factor beta [TGFβ]) and central nervous system (IL-4). Here the inventors evaluated whether M. vaccae immunization induces an anti-inflammatory immunophenotype in the aged brain. Overall, IL-10 mRNA was expressed at a low level and was not detectable in a number of samples (spread equally throughout the groups). In PCR samples that did amplify before 35 cycles, there was an age-related reduction in IL-10 mRNA expression ($F_{1,34}$=9.1, see Table 1). However, *M. vaccae* did not significantly upregulate IL-10 mRNA expression. TGF-β was not significantly regulated by age, surgery, or *M. vaccae* treatment (Table 1). In contrast, IL-4 mRNA expression was suppressed in the hippocampus of aged rats. *M. vaccae* treatment was protective against age associated decrements in IL-4 (age×*M. vaccae*: $F_{1,45}$=7.2, p<0.05; FIG. 2E): *M. vaccae* increased IL-4 expression in the hippocampus of aged, but not young adult rats (post hoc, p<0.05).

IL-4 induces anti-inflammatory (M2) polarization in peripheral macrophages as well as cluster of differentiation 200 (CD200) in the CNS, which inhibits pro-inflammatory activation in microglia through its cognate receptor cluster of differentiation 200 receptor 1 (CD200R1) expressed on microglia. Thus, we also evaluated several markers typical of M2 cells (arginase 1 (Arg1) and cluster of differentiation 206 (CD206)) and CD200. Arg1 and CD206 were reduced in aged rats and significantly upregulated by *M. vaccae* treatment (age×*M. vaccae*, p<0.05; FIG. 2F and Table 1).

There were also age-related reductions in CD200 (age: $F_{1,45}$=7.7, p<0.05), but no compensation by treatment with *M. vaccae* (p>0.05; Table 1). There was no effect of surgery or three-way interaction on Arg1, CD206, or CD200 gene expression. Of note, tissue for gene analyses was collected 8 days after the final *M. vaccae* injection so it is possible that upregulation of additional markers of alternative activation might occur at acute (earlier) post-injection time points.

To determine whether *M. vaccae* had persistent effects on neuroinflammatory phenotype, hippocampi were examined from rats that underwent fear conditioning (13 days following the final injection of *M. vaccae*). At this later time point-*M. vaccae* and -laparotomy, IL-4 and Arg1 were also significantly upregulated in the hippocampus of *M. vaccae*-immunized rats ($F_{1,36}$=7.6, p<0.05; Table 1). There were no differences in IL-1β at this later time point (p>0.05, Table 1). Thus, *M. vaccae* treatment in aged rats elicits an anti-inflammatory shift in the CNS milieu that persists for at least about 2 weeks post-immunization.

Example 4: Aged Rats Increased T Cell Markers in the Hippocampus

The peripheral anti-inflammatory effects of *M. vaccae* have been largely attributed to effects on T cells but T cells are not routinely detected in the brain parenchyma as access is tightly regulated by the blood-brain barrier. Here, the inventors showed that mRNA expression for the pan T cell marker, CD3, is upregulated in the hippocampus of aged rats and reduced by *M. vaccae* immunization (age×*M. vaccae* $F_{1,45}$=8.6, <0.05; FIG. 3A). CD4, a marker for helper T cells, was strongly upregulated in the hippocampus of aged rats (age: $F_{1,45}$=90.9, p<0.05; FIG. 3B). Furthermore, Forkhead Box P3 (FOXP3) mRNA expression, which directs development and function of regulatory T cells, was increased by *M. vaccae* treatment in aged subjects (age: $F_{1,45}$=5.2, *M. vaccae*: $F_{1,45}$=4.7, p<0.05; FIG. 3C). This suggests that *M. vaccae* treatment shifts the population of T cells gaining access to the CNS.

Example 5: *M. vaccae* Immunization Dampened Inflammatory Responses of Aged Microglia Ex Vivo Microglia are considered the predominant innate immune cell of the CNS and a key cellular substrate of aging-induced neuroinflammatory priming. Therefore, the inventors examined whether in vivo *M. vaccae* immunization in aged rats reduces ex vivo microglia reactivity. To test this possibility, microglia were isolated from the hippocampus of aged rats five days after the final injection of *M. vaccae* and directly exposed to an immune challenge (outlined in FIG. 4A). It is important to note here that in the findings presented thus far, laparotomy served as an immune challenge in vivo. In the present experiment, microglia were directly exposed to an immune challenge ex vivo to determine whether *M. vaccae* treatment in vivo blunts microglia priming. In this case, LPS served as the immune challenge instead of laparotomy given our prior findings that the microglial proinflammatory response to LPS ex vivo is potentiated in aged animals. Also, it is important to note that young animals were not included here given the lack of an *M. vaccae* effect on anti-inflammatory processes in these animals. Microglia were plated ex vivo and challenged with media alone (0 ng LPS control) or LPS (10 and 100 ng). *M. vaccae* immunization blunted aged microglia reactivity to LPS as indicated by IL-1β mRNA expression (*M. vaccae*×LPS: $F_{2,18}$=3.7, p<0.05; FIG. 4B) and IL-6 mRNA expression (LPS: $F_{2,18}$=30.7, *M. vaccae*: $F_{1,18}$=8.7, p<0.05; FIG. 4C). *M. vaccae* also reduced NFKBIA increases caused by LPS treatment (*M. vaccae*× LPS: $F_{2,18}$=4.6, p<0.05, FIG. 4D).

These data demonstrated that aged rats, but not young rats, showed post-operative learning/memory deficits in a fear conditioning paradigm. *M. vaccae* immunization protected aged rats from these surgery-induced cognitive impairments. *M. vaccae* immunization also shifted the aged proinflammatory hippocampal microenvironment towards an anti-inflammatory phenotype. Furthermore, *M. vaccae* immunization reduced age-related hyperinflammatory responses in isolated hippocampal microglia. Overall, these data suggest *M. vaccae* can induce an anti-inflammatory milieu in the aged brain and thus mitigate the neuroinflammatory and cognitive impairments induced by surgery.

Example 6: Attenuation of Stress-Induced Microglial Priming, Alarmins, And Anxiety-Like Behavior The following materials and methods were used to conduct the experiments described in this Example:

Animals: Adult male Sprague-Dawley rats (60-90 d old) were pair-housed with food and water available ad libitum. The colony was maintained at 22° C. on a 12 h light/dark cycle (lights on at 07:00 h).

*M. vaccae* treatment: *M. vaccae* is a saprophytic environmental *Mycobacterium*, which we have used previously to mitigate stress-induced anxiety-like behavior and peripheral proinflammatory responses. Briefly, whole heat-killed *M. vaccae* (strain NCTC 11659, batch ENG 1; Bio Elpida; 10 mg/ml) was suspended in sterile borate-buffered saline (BBS) to yield a final concentration of 1 mg/ml. Sterile BBS served as the vehicle control. Consistent with our prior work with *M. vaccae*, experimental animals received 3× subcutaneous (s.c.) immunizations with 0.1 mg whole heat-killed *M. vaccae* suspension (0.1 ml) or vehicle (0.1 ml). Injections occurred at −21 d, −14 d and −7 d prior to stress exposure. FIG. 5 provides a timeline of *M. vaccae* treatment relative to stress exposure, behavioral testing and tissue/microglia collection.

Recombinant rat IL4 (rIL4) treatment: Vehicle (sterile 1×PBS+0.1% BSA) or rIL4 (100 ng dissolved in vehicle; R & D Systems) was injected intra-cisterna magna (i.c.m.; 5 μl total volume). Two and 24 h post-injection, hippocampus was collected for gene expression analysis of IL4-sensitive target genes. The dose of rIL4 used here was based on findings that intracerebroventricular (i.c.v.) administration of this dose of rIL4 was sufficient to induce robust expression of IL4-sensitive genes in hippocampus. We have demonstrated that i.c.m. injections of substances reach distal target regions in the CNS (i.e., hippocampus) consistent with more typical i.c.v. procedures, and this procedure produces no detectable inflammatory responses. Rats were anesthetized with 5% isoflurane in oxygen and then maintained on 3% isoflurane during the brief procedure (approx. 3 min). The dorsal aspect of the skull was shaved and swabbed with 70% EtOH. A sterile 27-gauge needle attached via sterile PESO tubing to a 25 µl Hamilton syringe was inserted transcutaneously at midline between the base of the skull and first vertebrae into the cisterna magna (verified by withdrawing 2 µl of clear CSF), and drug was injected over a 30 s period. After injection, the needle was left in place for 30 s to allow for diffusion of drug.

Inescapable tailshock (IS): Details of the stressor protocol have been published previously and this protocol reliably potentiates proinflammatory cytokine responses in the hippocampus after peripheral immune challenge and sensitizes ex vivo lipopolysaccharide (LPS)-induced proinflammatory cytokine secretion from isolated hippocampal microglia. Briefly, animals were placed in Plexiglas® tubes (23.4 cm in length×7 cm in diameter) and exposed to 100 1.6 mA, 5-s tailshocks with a variable inter-trial interval (ITT) ranging from 30-90s (average ITI=60 s). All IS treatments occurred between 09:00 and 11:00 h. IS animals were returned to their home cages immediately after termination of shock. Home cage control (HCC) animals remained undisturbed in their home cages.

Tissue and blood collection: Animals were given a lethal dose of sodium pentobarbital. Cardiac blood was collected by cardiac puncture after opening the thoracic cavity. Transcardial perfusion was then performed with ice-cold saline (0.9%) for 3 min to remove peripheral immune leukocytes from the CNS vasculature. Brain was rapidly extracted, placed on ice and brain regions bilaterally dissected with each hemisphere designated for either protein or mRNA analysis. Hippocampus was collected given our prior findings of robust stress-induced priming effects in this region and amygdala was also collected as a stress-sensitive limbic structure. Choroid plexus was removed from hippocampus prior to tissue processing. For experiments involving measurement of in vivo cytokine mRNA expression and protein, hippocampus and amygdala were flash frozen in liquid nitrogen and stored at −80° C. For experiments involving measurement of IL4 mRNA expression and protein in dorsal, intermediate, and ventral hippocampus, hippocampus was dissected and each hemisphere was trisected into these distinct subregions based on the method of Lee et al. (Frontiers in Molecular Neuroscience, 10:331, 2017). Hippocampal subregions were flash frozen in liquid nitrogen and stored at −80° C. For experiments involving ex vivo LPS stimulation of isolated hippocampal microglia, hippocampal microglia were immediately isolated.

Serum corticosterone (CORT) assay: Blood was collected in untreated Eppendorf tubes, centrifuged (10 min, 14,000× g, 4° C.) and serum collected. CORT was measured in duplicate using a competitive immunoassay (Enzo Life Science) as described in the manufacturer's protocol (intra-assay mean % CV=7.7; inter-assay mean % CV=9.7).

Ex vivo immune stimulation of hippocampal microglia with LPS: Hippocampal microglia were isolated using a Percoll density gradient as previously described. We have previously shown that this microglia isolation procedure yields highly pure microglia (Iba-1+/Cd163-/Gfap-mRNA). In the present experiments, immunophenotype and purity of microglia were assessed using real time RT-PCR. Microglia were suspended in DMEM+10% FBS and microglia concentration was determined by trypan blue exclusion. Microglia concentration was adjusted to a density of $1 \times 10^4$ cells/100 µl and 100 µl added to individual wells of a 96-well v-bottom plate. LPS (*E. coli* serotype O111:B4; Sigma-Aldrich) was utilized to challenge microglia ex vivo as we have previously determined the optimal in vitro conditions under which LPS stimulates a microglial proinflammatory cytokine response. Cells were incubated with LPS (1, 10, and 100 ng/ml) or media alone for 2 h at 37° C., 5% $CO_2$. The plate was centrifuged at 1000× g for 10 min at 4° C. to pellet cells and cells were then washed 1× in ice-cold PBS and centrifuged at 1000×g for 10 min at 4° C. Cell lysis/homogenization and cDNA synthesis were performed according to the manufacturer's protocol using the SuperScript III CellsDirect cDNA Synthesis System (Invitrogen).

Real time RT-PCR measurement of gene expression: Total RNA was isolated from whole hippocampus and amygdala utilizing a standard method of phenol:chloroform extraction. For detailed descriptions of RNA isolation, cDNA synthesis and PCR amplification protocols refer to prior publication. cDNA sequences were obtained from Genbank at the National Center for Biotechnology Information (ncbi.nlm.nih.gov). Primer sequences were designed using the Operon Oligo Analysis Tool (operon.com/technical/toolkit.aspx) and tested for sequence specificity using the Basic Local Alignment Search Tool at NCBI. Primers were obtained from Invitrogen. Primer specificity was verified by melt curve analyses. All primers were designed to span exon/exon boundaries and thus exclude amplification of genomic DNA (see Table 2 for primer description and sequences).

| Gene Symbol | Primer Sequence 5'-3' | Function |
| --- | --- | --- |
| Actb | F: TTCCTTCCTGGGTATGGAAT (SEQ ID NO. 1) GAGGAGCAATGATCTTGATC (SEQ ID NO. 2) | Cytoskeletal protein (housekeeping gene) |
| Arg1 | F: CTACCTGCTGGGAAGGAAG (SEQ ID NO. 3) R: GTCCTGAAAGTAGCCCTGTC (SEQ ID NO. 4) | IL4-sensitive gene |
| Cd3e | F: AAAGCCAGAGTGTGCGAGAA (SEQ ID NO. 5) R: CCTTCCTTTTCTTGCTCCAG (SEQ ID NO. 6) | Epsilon chain of the T-cell receptor-CD3 complex |

-continued

| Gene Symbol | Primer Sequence 5'-3' | Function |
|---|---|---|
| Cd163 | F: GTAGTAGTCATTCAACCCTCAC (SEQ ID NO. 7)<br>R: CGGCTTACAGTTTCCTCAAG (SEQ ID NO. 8) | Hemoglobin receptor expressed by macrophages, but not microglia |
| Cd200 | F: CTCTCTATGTACAGCCCATAG (SEQ ID NO. 9)<br>R: GGGAGTGACTCTCAGTACTAT (SEQ ID NO. 10) | Neuronal antigen that binds CD200R1 to inhibit microglial function |
| Cd200r1 | F: TAGAGGGGGTGACCAATTAT (SEQ ID NO. 11)<br>R: TACATTTTCTGCAGCCACTG (SEQ ID NO. 12) | Cognate receptor for CD200 that inhibits microglial function |
| Gfap | F: AGATCCGAGAAACCAGCCTG (SEQ ID NO. 13)<br>R: CCTTAATGACCTCGCCATCC (SEQ ID NO. 14) | Astrocyte antigen |
| Iba1 | F: GGCAATGGAGATATCGATAT (SEQ ID NO. 15)<br>R: AGAATCATTCTCAAGATGGC (SEQ ID NO. 16) | Microglia/macrophage antigen |
| Il1b | F: CCTTGTGCAAGTGTCTGAAG (SEQ ID NO. 17)<br>R: GGGCTTGGAAGCAATCCTTA (SEQ ID NO. 18) | Pro-inflammatory cytokine |
| Il4 | F: GAACTCACTGAGAAGCTGCA (SEQ ID NO. 19)<br>R: GAAGTGCAGGACTGCAAGTA (SEQ ID NO. 20) | Anti-inflammatory cytokine in the CNS |
| Il6 | F: AGAAAAGAGTTGTGCAATGGCA (SEQ ID NO. 21)<br>R: GGCAAATTTCCTGGTTATATCC (SEQ ID NO. 22) | Pro-inflammatory cytokine |
| Il10 | F: GGACTTTAAGGGTTACTTGGG (SEQ ID NO. 23)<br>R: AGAAATCGATGACAGCGTCG (SEQ ID NO. 24) | Anti-inflammatory cytokine |
| Il13 | F: AGACCAGAAGACTTCCCTGT (SEQ ID NO. 25)<br>R: TCAATATCCTCTGGGTCCTG (SEQ ID NO. 26) | Anti-inflammatory cytokine |
| Mrc1 | F: GGGGTTGTTGCTGTTGATGT (SEQ ID NO. 27)<br>R: GCTCGAAACGGAAAAGGTTC (SEQ ID NO. 28) | Receptor for mannose that is induced by IL4 |
| Nts | F: TGCATCGAAGGTCAGCAAAG (SEQ ID NO. 29)<br>R: TCCTTTTCGCAACAAGGTCG (SEQ ID NO. 30) | A highly enriched mRNA in dorsal hippocampus |
| Nfkbia | F: CACCAACTACAACGGCCACA (SEQ ID NO. 31)<br>R: GCTCCTGAGCGTTGACATCA (SEQ ID NO. 32) | Induced by NFkB to inhibit NFkB function |
| Nlrp3 | F: AGAAGCTGGGGTTGGTGAATT (SEQ ID NO. 33)<br>R: GTTGTCTAACTCCAGCATCTG (SEQ ID NO. 34) | Inflammasome component mediating caspase-1/IL1B activation |
| Nr2f2 | F: TGTTCACCTCAGATGCCTGT (SEQ ID NO. 35)<br>R: AGGGAGACGAAGCAAAAGCT (SEQ ID NO. 36) | A highly enriched mRNA in ventral hippocampus |

-continued

| Gene Symbol | Primer Sequence 5'-3' | Function |
|---|---|---|
| Tgfb1 | F: TACTGCTTCAGCTCCACAGA (SEQ ID NO. 37) R: TGTCCAGGCTCCAAATGTAG (SEQ ID NO. 38) | Anti-inflammatory cytokine |
| Tnf | F: CAAGGAGGAGAAGTTCCCA (SEQ ID NO. 39) R: TTGGTGGTTTGCTACGACG (SEQ ID NO. 40) | Pro-inflammatory cytokine |

PCR amplification of cDNA was performed using the QuantiTect SYBR Green PCR Kit (Qiagen). Formation of PCR product was monitored in real time using the MyiQ Single-Color Real-Time PCR Detection System (Bio-Rad). Relative gene expression was determined by taking the expression ratio of the gene of interest to β-actin.

Isolation of lipids from *M. vaccae*: Wet cells (200 g of paste of sterile heat-killed whole cell *M. vaccae*) were extracted using 440 mL of petroleum ether, 400 mL of methanol, and 40 mL 0.3% aqueous sodium chloride overnight with gentle agitation. The mixture was then left to stand and the upper organic petroleum-ether supernatant fraction was separated by careful aspiration. The lower aqueous phase was extracted again using petroleum ether (400 mL) as described above. The petroleumether extracts were combined and dried to yield the apolar lipids. The lower aqueous phase was then extracted using chloroform/methanol/water (90:100:30; 520 mL) with gentle agitation, overnight. The resulting lipid extract was separated by vacuum filtration and the residual biomass extracted using chloroform/methanol/water (50:100:40; 170 mL) overnight with gentle agitation twice. The three polar lipid extractions were combined and chloroform (290 mL) and 0.3% aqueous sodium chloride (290 mL) were added. The entire mixture was briefly shaken, allowed to settle and the upper phase was carefully removed and discarded. The lower organic layer was dried to yield the polar lipids. The polar lipids were resuspended in a minimum volume of chloroform (20 mL) and added to chilled acetone (1.5 L) and left at 4° C., overnight. The resulting precipitate (lipid fraction 147) was separated by centrifugation from the acetone soluble lipids (220 mg) designated lipid fraction 148. Fraction 148 was further fractioned using column chromatography using increasing amounts of methanol in chloroform to afford seven lepidic fractions. These were screened for their immunomodulatory potential as described below. While a number of fractions were deemed interesting, fraction 148.2 (82 mg) was further analyzed. The resulting fraction was deemed pure by thin-layer chromatography (TLC) using chloroform as an eluant following charring with a heat gun after spraying with 5% ethanolic molybdophosphoric acid. Through a combination of high resolution mass spectrometry (HRMS), 1-dimensional (1D) (1H and 13C), and two-dimensional (2D) (correlation spectroscopy (COSY) and 1H/13C heteronuclear multiple bond correlation (HMBC)) nuclear magnetic resonance (NMR) spectroscopy, and gas chromatography-mass spectrometry (GC-MS) analyses, the structure of the triglyceride was completely determined.

Synthesis of triacylglycerol: Referring to FIG. 15, the acetylenic carboxylic acid (1) and trimethylsilyl chloride (0.1 equivalent) in anhydrous methanol were mixed at room temperature for 12 hours. The reaction was evaporated to dryness to yield the pure methyl ester product (2) as confirmed by thin layer chromatography (TLC) and 1H/13C-NMR analysis and was used directly in the next step without further purification. The carboxylic acid methyl ester (2) was dissolved in diethyl ether and 2 equivalents of lithium aluminum hydride were added and the reaction was stirred at room temperature for 4 hours. The reaction was quenched with glacial acetic acid and the acetylenic alcohol product (3) was extracted with diethyl ether and water. The ethereal layer was recovered and washed with water and then brine, then concentrated to dryness. To a solution of the acetylenic alcohol (3) (1 equivalent) in hexamethylphosphoramide (HMPA), n-butyl lithium (2 equivalents) was added at 0° C. under nitrogen over a period of 30 min. The reaction was stirred at 0° C. for 20 min. 1-iodopentane (1.4 equivalent) was added and the reaction mixture was left to warm to ambient temperature and stirred for 20 hours. The reaction was quenched with the addition of saturated aqueous ammonium chloride and the product (4) was extracted with diethyl-ether. The product (4) was concentrated and purified by column chromatography using a petroleum ether-ethyl acetate gradient, monitored by TLC and characterized by 1H/13C-NMR. A suspension of Lindlar's catalyst in dry benzene was saturated with hydrogen gas and cooled to 10° C. Then a solution of (4) in benzene and quinoline was added under a stream of nitrogen. The reaction mixture was stirred for 1 hour at 10° C. The reaction mixture was filtered, concentrated and the product (5) was purified by column chromatography using a petroleum ether-ethyl acetate gradient, monitored by TLC and characterized by 1H/13C-NMR. A solution of (5) in dichloromethane (1 volume) was added to a stirring solution of pyridinium dichromate (4 equivalents) in dimethylformamide (DMF, 10 volumes). The reaction mixture was stirred for 2 days at room temperature. Water was added and the product (6) was extracted into dichloromethane, washed with brine and concentrated. The product (6) was purified by column chromatography and characterized by MS and 1H/13C-NMR. The starting acid (6) was dissolved in dichloromethane/DMF and oxalyl chloride was added; the reaction mixture was then stirred at room temperature for 1 hour. The reaction mixture was evaporated and the crude acid chloride (7) was used in the next step. Glycerol (1 equivalent) in pyridine was added to the acid chloride (7) (3.3. equivalents) and the reaction mixture was left to stir overnight. Dichloromethane and water were added to the reaction mixture and the product was recovered in the organic layer and concentrated. The synthetic triacylglycerol was purified by column chromatography using increasing methanol in chloroform, monitored by TLC and characterized by MS, and 1H/13CNMR analyses.

Synthesis of 10(Z)-hexadecenoic acid; (10Z)-hexadec-10-enoic acid (CAS No. 2511-97-9): Unless otherwise noted, reagents were obtained commercially and used without further purification. Dichloromethane (CH2C12) was distilled over calcium hydride (CaH2) under a nitrogen atmosphere. Tetrahydrofuran (THF; (CH2)40) was distilled from sodium-benzophenone under a nitrogen atmosphere. Thin-layer chromatography analysis of reaction mixtures was performed on Dynamic Adsorbents, Inc., silica gel F-254 TLC plates. Flash chromatography was carried out on Zeoprep 60 ECO silica gel. 1H spectra were recorded with a Varian INOVA 500 spectrometer. Compounds were detected by monitoring UV absorbance at 254 nm. To a 5 mL sealed tube containing 1-heptene (0.50 mL, 3.55 mmol), methyl 10-undecenoate (0.080 mL, 0.36 mmol) and 0.35 mL THF was added to a Grubbs Z-selective metathesis catalyst (2.2 mg, 3.48 µmol, Sigma-Aldrich, Cat. No. 771082). The reaction was stirred at 45° C. for 8 h before cooling to room temperature. The slurry was filtrated through a short plug of silica gel and concentrated. The obtained oil was dissolved in 1.0 mL THF. The solution was cooled to 0° C., then 9-borabicyclo[3.3.1]nonane (9-BBN) solution in THF (1.28 mL, 0.50 M, 0.64 mmol) was added. After 2 h stirring at 0° C., the reaction was quenched with 60 µL EtOH, then 1.5 mL pH 7 potassium phosphate buffer and 1.5 mL 30% H2O2. The mixture was stirred at room temperature for 12 h, then extracted with 5 mL EtOAc three times. The combined organic layers were washed with 4 mL saturated Na2S2O3 and 3 mL brine, then dried over Na2SO4, filtered and concentrated. To the crude oil in 1.0 mL THF was added LiOH monohydrate (38 mg, 0.90 mmol) in 1.0 mL water. After 2 h, the reaction solution was cooled to 0° C. before addition of 0.91 mL 1.0 N HCl. After being concentrated under reduced pressure, the aqueous solution was saturated with NaCl and extracted with 3 mL dichloromethane three times. The combined organic layers were dried over Na2SO4, filtered and concentrated. Purification by flash chromatography (2:1:1 hexanes/dichloromethane/diethyl ether) provided (10Z)-hexadec-10-enoic acid (0.022 g, 90%) as a colorless oil. 1H NMR (500 MHz, CDCl3): δ 5.48-5.22 (m, 2H), 2.35 (t, J=7.5 Hz, 2H), 2.01 (q, J=6.6 Hz, 4H), 1.63 (p, J=7.4 Hz, 2H), 1.35-1.15 (m, 16H), 0.88 (t, J=6.9 Hz, 3H).

Enzyme-linked immunosorbent assay (ELISA): Hippocampus was sonicated in a mixture containing extraction buffer (Invitrogen) and protease inhibitors (Sigma-Aldrich). Ice-cold tissue sonicates were centrifuged at 14,000 rpm for 10 min at 4° C. The supernatant was removed and the total protein concentration for each sample was quantified using the Bradford method. High Mobility Group Box 1 (HMGB1; LifeSpan Biosciences, Inc.), IL1B (R & D Systems) and IL4 (R & D Systems) protein was measured using a standard colorimetric sandwich ELISA according to the manufacturer's instructions. Protein was quantified as pg/mg total protein.

Juvenile social exploration (JSE): Stress exposure (IS) produces robust decrements in JSE, which is a widely used and validated measure of anxiety and is sensitive to the neuroinflammatory effects of stress. Here, JSE was measured 24 h prior to (baseline) and 24 h after IS (test). Each experimental subject was transferred to a novel cage with shaved wood bedding in a dimly lit room (40 1x). After a 15-min habituation period, a 28-32 day-old juvenile male rat was introduced to the subject's cage for 5 min. Exploratory behaviors of the adult (sniffing, pinning, licking and allo-grooming of the juvenile) were timed by an observer blind to treatment condition. After the test, the juvenile was removed and the experimental adult rat was returned to its homecage. Although juvenile stimulus rats were reused for multiple tests, the adult was never re-tested with the same juvenile. For each animal, JSE test data were quantified as a percent of baseline JSE.

Statistical analysis and data presentation: All data are presented as mean+s.e.m. Statistical analyses consisted of Student's t-tests or ANOVA followed by post hoc tests (Newman-Keuls) using Prism 5 (Graphpad Software, Inc.). Threshold for statistical significance was set at two-tailed $\alpha=0.05$. Sample sizes are provided in figure captions. Area under the LPS concentration curve (AUC) was computed to capture the cumulative effect of stress and *M. vaccae* treatment on the cytokine response to LPS ex vivo.

The inventors examined the effect of *M. vaccae* NCTC11659 on neuroimmune regulation, stress-induced neuroinflammatory processes and anxiety-like behavior.

Example 7: Effect of *M. vaccae* on Hippocampal and Amygdalar Anti-Inflammatory Mediators and Markers of Alternative Activation

*M. vaccae* treatment has been found to increase peripheral levels of anti-inflammatory cytokines including IL10 and transforming growth factor beta (TGFB1). Therefore, the inventors conducted an initial investigation into whether *M. vaccae* treatment induces an anti-inflammatory immunophenotype in the CNS independent of stress exposure. Here, the effect of *M. vaccae* on the gene expression of several anti-inflammatory mediators (Il4, Il10, Il13, and Tgfb 1) was examined. As depicted in FIG. 6A, *M. vaccae* treatment increased expression of Il4 (t=3.61, df=18, p=0.002) in hippocampus; however, all other analytes were either not affected by *M. vaccae* treatment (Tgfb 1) or not detected due to low expression levels (Il10, Il13). *M. vaccae* also increased IL4 protein levels in hippocampus (contralateral hemisphere) of the same animals (see FIG. 6A inset; t=2.86, df=22, p=0.008). Interestingly, *M. vaccae* failed to affect the expression level of these analytes in the amygdala.

IL4 is considered a powerful stimulus of alternative macrophage activation also termed a wound healing macrophage phenotype. IL4 has been found to induce markers of alternative macrophage activation including arginase 1 (ARG1), the mannose receptor (MRC1) and CD200R1. In addition, IL4 is a stimulus of neuronal CD200 expression, which is thought to constrain microglial activation via ligation of CD200R1. Therefore, the inventors examined the effect of *M. vaccae* on these IL4-sensitive antigens in hippocampus. As depicted in FIG. 6B, *M. vaccae* treatment increased expression of Cd200r1 (t=2.71, df=22, p=0.01) as well as Mrc1 (t=2.48, df=22, p=0.02), but failed to alter expression of Cd200 and arg1. In the amygdala, M *vaccae* failed to significantly alter the expression levels of any of these IL4-sensitive targets, which is consistent with the lack of an *M. vaccae* effect on amygdalar IL4 as well as other anti-inflammatory cytokines. Because *M. vaccae* failed to induce an anti-inflammatory milieu in amygdala, subsequent experiments excluded amygdala analyses and focused solely on *M. vaccae*'s effects in hippocampus.

Example 8: Effect of *M. vaccae* on Hippocampal Proinflammatory Mediators

Under basal conditions, IL4 largely fails to modulate expression of proinflammatory cytokines; however, it attenuates the proinflammatory response to immune challenge. Interestingly, IL4 is capable of down-regulating basal mRNA levels of NLR family pyrin domain containing 3 (Nlrp3), which is an inflammasome component that mediates the processing of pro-IL1B into its mature, bioactive form. Here, the inventors tested whether basal levels of proinflammatory mediators in the hippocampus were altered in the context of increased hippocampal IL4. *M. vaccae* treatment failed to affect basal gene expression of proinflammatory cytokines (Il1b, Il6, and Tnf) as well as IL1B protein, but reduced expression of Nlrp3 ($t=2.25$, $df=22$, $p=0.035$) and nuclear factor of kappa light polypeptide gene enhancer in B-cells inhibitor, alpha (Nfkbia) ($t=2.71$, $df=22$, $p=0.013$) (FIG. 7).

Example 9: Effect of rIL4 on the Hippocampal Immunophenotype

The data presented thus far suggest that IL4 might play a pivotal role in *M. vaccae*'s anti-inflammatory effects in the CNS. To address this possibility, the inventors examined whether administration of rIL4 is sufficient to recapitulate the anti-inflammatory effects of *M. vaccae*. Here, rIL4 was administered i.c.m. and the effect on *M. vaccae*-sensitive antigens (Cd200, Cd200r1, Mrc1) was then examined in hippocampus 2 h and 24 h post-injection. As depicted in FIG. 8, rIL4 induced a significant increase in Mrc1 at 2 h post-injection ($t=3.09$, $df=12$, $p=0.009$) and Cd200r1 at 2 h ($t=2.7$, $df=12$, $p=0.04$) and 24 h post-injection ($t=5.1$, $df=6$, $p=0.002$), but failed to significantly alter expression of Cd200 at either timepoint, thus recapitulating the effects of *M. vaccae*.

Example 10: Effect of *M. vaccae* on Stress-Induced Microglial Priming

NLRP3 and NFKBIA signaling have been implicated in stress-induced microglial priming. Given the effects of *M. vaccae* on basal expression of these genes, we examined the possibility that *M. vaccae*'s anti-inflammatory effects may buffer the CNS against the neuroinflammatory priming effects of stress. Exposure to acute stress sensitizes microglia to proinflammatory immune challenges ex vivo such that acute stress exposure potentiates the microglial proinflammatory cytokine response to subsequent immune challenges (e.g., LPS). Here, animals were exposed to stress 7 d after the final *M. vaccae* injection. Hippocampal microglia were isolated 24 h after termination of the stressor and challenged with LPS ex vivo. Depicted in FIGS. 9A and 9C are data showing the proinflammatory response of microglia to several concentrations of LPS in vitro and the differential effects of stress and *M. vaccae* treatment. Area-under-the-curve (AUC) analysis (FIGS. 9B and 9D) was used to represent the overall magnitude of the proinflammatory response across LPS concentrations and to examine the interaction between stress and *M. vaccae* treatment on this response. The interaction between stress and *M. vaccae* treatment was significant for Il1b (interaction effect, $F=15.48$, $df=1$, $12$, $p=0.002$; FIG. 9B) and Nfkbia (interaction effect, $F=10.75$, $df=1$, $12$, $p=0.007$; FIG. 9D), while the interaction between these treatments on Il6 and Tnf failed to attain significance. Post hoc comparisons show that in vehicle-treated animals, stress potentiated the Il1b ($p<0.05$; FIG. 9B) and Nfkbia ($p<0.05$; FIG. 9D) responses to LPS compared to HCC animals. In IS-exposed animals, *M. vaccae* treatment significantly reduced the Il1b ($p<0.05$; FIG. 9B) and Nfkbia ($p<0.05$; FIG. 9D) responses compared to vehicle treatment, thus blunting the proinflammatory response to levels comparable to HCC animals.

Example 11: Effect of *M. vaccae* on Basal and Stress-Induced Serum CORT Levels

It is important to consider the possibility that *M. vaccae*'s effect on microglial priming could be due to *M. vaccae*'s effects on basal as well as stress-induced levels of glucocorticoids, which have profound anti-inflammatory effects as well as paradoxical effects on neuroinflammatory processes. Serum CORT levels were measured 24 h after IS exposure in animals immunized with *M. vaccae*. Consistent with our prior work, IS induced a persistent elevation in serum CORT 24 h after termination of the stressor independent of *M. vaccae* treatment (FIG. 10; main effect of IS, $F=29.88$, $df=1$, $39$, $p<0.0001$). In addition, *M. vaccae* treatment failed to alter basal levels of serum CORT in HCC animals.

Example 12: Effect of *M. vaccae* on Stress-Induced Reductions in Cd200r1

Recent evidence from our laboratory demonstrates that exposure to IS reduces Cd200r1 expression 0 h and 24 h after termination of the stressor. Additionally, the inventors found that IS disrupts CD200:CD200R1 signaling, thereby leading to microglial disinhibition and priming of microglial proinflammatory responses ex vivo. Considering that *M. vaccae* induces hippocampal Cd200r1 expression, we explored the possibility that *M. vaccae* treatment might prevent the stress-induced reductions in Cd200r1 gene expression. Consistent with prior findings, the inventors found that stress reduced expression of Cd200r1 compared to HCC animals (FIG. 11A; main effect of IS, $F=14.68$, $df=1$, $41$, $p<0.001$) and that *M. vaccae* treatment increased Cd200r1 expression compared to vehicle treatment (main effect of *M. vaccae*, $F=24.47$, $df=1$, $41$, $p<0.0001$), thus preventing stress-induced reductions in Cd200r1 expression. To examine whether these effects of stress and *M. vaccae* on Cd200r1 extended to microglia, hippocampal microglia were isolated 24 h after stress exposure in animals treated with vehicle or *M. vaccae*. Similar to observations in whole hippocampus, stress induced a reduction in microglial Cd200r1 expression, which was prevented by *M. vaccae* immunization (FIG. 11B; interaction effect, $F=9.82$, $df=1$, $12$, $p<0.01$). Post hoc comparisons demonstrated that in vehicle-treated animals, exposure to IS reduced Cd200r1 expression compared to HCCs ($p<0.001$); however, in IS-exposed animals, *M. vaccae* treatment abrogated this effect of IS on Cd200r1 compared to vehicle treatment ($p<0.001$).

Example 13: Effect of *M. vaccae* on Stress-Induced HMGB1

Alarmins are host biomolecules that can initiate and perpetuate a noninfectious inflammatory response, often in response to cell or tissue damage, or immune activation. Stress induces the alarmin HMGB1 in hippocampus and increases release of HMGB1 protein from hippocampal microglia ex vivo. Additionally, HMGB1 mediates stress-induced priming of microglial proinflammatory responses assessed ex vivo. Interestingly, the inventors also found that HMGB1 induces a primed phenotype in primary microglia, which was characterized by up-regulation of Nlrp3 and Nfkbia, but not proinflammatory cytokines, and that stress-induced increases in HMGB1 are a consequence of disrupted CD200:CD200R1 signaling.

Considering the effects of *M. vaccae* on Nlrp3, Nfkbia, and Cd200r1 (in the absence of any effects on proinflammatory cytokines) as well as its effects on stress-induced microglial priming, the inventors explored the possibility that *M. vaccae* might modulate stress-induced HMGB1. Consistent with our prior findings, exposure to IS resulted in a significant upregulation of hippocampal HMGB1 protein levels compared to levels in HCC animals; however, this effect of IS was blocked by prior immunization with *M. vaccae* (FIG. 12; interaction effect, $F=5.19$, $df=1$, $39$, $p=0.03$). Post hoc comparisons demonstrate that HMGB1 levels in vehicle-treated IS animals were significantly increased compared to levels observed in vehicle-treated HCC ($p<0.01$), *M. vaccae*-treated HCC ($p<0.01$) and *M. vaccae*-treated IS ($p<0.01$) animals.

Example 14: Effect of *M. vaccae* on stress-induced anxiety-like behavior

Exposure to acute and chronic stressors induces anxiety-like behavior in a number of behavioral tests including the juvenile social exploration (JSE) test, which is blocked by central administration of anti-inflammatory mediators such as IL1 receptor antagonist. Likewise, central administration of rIL4 blocks LPS-induced anxiety-like behavior. Therefore, given *M. vaccae*'s induction of an anti-inflammatory milieu in the CNS, we examined whether *M. vaccae* would mitigate the effects of stress on anxiety-like behavior. As depicted in FIG. 13, *M. vaccae* treatment differentially modulated the effect of IS on JSE (interaction effect, $F=5.41$, $df=1$, $42$, $p=0.02$). Consistent with prior findings, IS reduced JSE 24h after stress exposure in vehicle-treated animals ($p<0.05$). However, *M. vaccae* treatment blunted this effect of IS on JSE compared to vehicle treatment ($p<0.05$).

Example 15: Effect of *M. vaccae* on IL4 mRNA and Protein Expression in Subregions of the Hippocampus A number of studies now suggest that there is an anatomical segregation of hippocampal function such that the dorsal hippocampus mediates spatial navigation and contextual memory, while the ventral hippocampus plays a role in fear and anxiety. Indeed, the ventral hippocampus selectively provides input to the amygdala, a brain structure critical for mediating fear and anxiety responses. Furthermore, the anti-inflammatory cytokine IL4 has been found to regulate learning and memory as well as depressive- and anxiety-like behavior.

Therefore, given the effect of *M. vaccae* on IL4 and stress-elicited anxiety-like behavior described above, the inventors explored the possibility that *M. vaccae* might differentially induce IL4 in the ventral versus the dorsal hippocampus. Animals received vehicle or *M. vaccae* as outlined in FIG. 5, and 8 days post-injection, hippocampus was trisected into dorsal, intermediate, and ventral subregions according to the experimental approach described in Lee et al. (Lee et al., 2017, supra). Interestingly, a number of genes are differentially expressed at high levels in rat dorsal versus ventral hippocampus. For example, neurotensin (Nts) is highly expressed in dorsal relative to ventral hippocampus, while Nr2f2 is highly expressed in ventral relative to dorsal hippocampus. Therefore, we initially assessed these mRNAs in dorsal, intermediate and ventral hippocampus to verify that our trisection of hippocampus resulted in the anatomical segregation of the hippocampus into the desired subregions. Consistent with the findings of Lee and colleagues, we found that Nts was highly expressed in dorsal versus intermediate and ventral sub-regions ($F=52.99$, $df=2$, $14$, $p<0.0001$), while Nr2f2 was highly expressed in ventral versus intermediate and dorsal subregions ($F=108.2$, $df=2$, $14$, $p<0.0001$). The inventors also assessed expression of Cd3e, which Lee et al. found to be the most enriched transcript in dorsal hippocampus compared to ventral hippocampus and is a component of the T cell receptor-CD3 complex. Indeed, the dorsal hippocampus exhibited high levels of Cd3e expression compared to intermediate and ventral hippocampus ($F=189.2$, $df=2$, $14$, $p<0.0001$).

Interestingly, *M. vaccae* treatment increased Cd3e expression only in dorsal hippocampus (brain region×*M. vaccae* interaction, $F=6.24$, $df=2$, $14$, $p<0.01$). These findings support that our trisection method resulted in the anatomical segregation of the hippocampus into dorsal, intermediate, and ventral subregions. Therefore, the inventors examined the effects of *M. vaccae* on IL4 in these subregions. Consistent with our initial findings, *M. vaccae* treatment induced IL4 mRNA (main effect of *M. vaccae*, $F=8.17$, $df=1$, $14$, $p<0.05$) and protein (main effect of *M. vaccae*, $F=7.58$, $df=1$, $14$, $p<0.05$) and did so irrespective of hippocampal subregion (FIGS. 14A and 14B). It should be noted that dorsal hippocampus tended to show a greater effect of *M. vaccae* on IL4; however, the interaction between *M. vaccae* and hippocampal subregion was not significant for either mRNA or protein.

Example 16: Administration of *M. vaccae* Increase IL-4 Protein in Plasma

As generally shown in FIG. 16, the present inventors demonstrated that the administration of *M. vaccae* resulted in approximately a 2× increase IL-4 protein in plasma taken from treated rats. Specifically, Serum ELISA data demonstrates that *M. vaccae* increases IL4 protein in serum compared to vehicle, * $p<0.05$, where N=12/group.

Example 17: Anti-Inflammatory Effects of Increase of IL-4 in the Brain from Administration of *M. vaccae* are Present in Both Male and Females As generally shown in FIGS. 21-24, the present inventors demonstrated that administration of *M. vaccae* (at day −21, −14, and −7) prior to tissue collection showed an increase of anti-inflammatory IL-4 in the hippocampus of both male and female rats tested.

Example 18: Effects of *M. vaccae* on Hippocampal Gene Expression can be Blocked by Inhibiting IL-4

As generally shown in FIGS. 25-26, the present inventors demonstrated that the effect of *M. vaccae* administration could be blocked through inhibition of IL-4 in the bran. In this embodiment, rats were administered *M. vaccae* or BBC (at day −21, −14, and −7) and then administered 5 µg of soluble IL-4 receptor alpha or a control vehicle. Notably, the soluble form of IL-4 receptor alpha can inhibit IL4-mediated cell proliferation.

Example 19: ICM Administration of *M. vaccae*, but not Oral Administration of LGG Increased IL-4 mRNA in Hippocampus As generally shown in FIGS. 27-31, the present inventors demonstrate that the administration of *M. vaccae* (s.c., 3× weekly injection), but not 21 day oral administration of LGG (a common probiotic) in the drinking water increase IL-4 mRNA in hippocampus.

Example 20: Effect of M. vaccae on IL-4 Protein in the Dorsal Hippocampus

Previous studies have shown that immunization with *M. vaccae* NCTC 11659 can increase hippocampal IL-4 protein expression in home cage control animals. In alignment with findings outlined above with 11-4 mRNA expression, the 2×2 ANOVA did not reveal an effect of treatment, stress, or a treatment x stress interaction on IL-4 protein in the dorsal hippocampus, although an interaction effect of treatment x stress approached significance ($F_{(2, 34)}=2.458$, $p=0.101$). As previous studies have shown that immunization with *M. vaccae* NCTC 11659 increases IL-4 protein in the dorsal hippocampus, this prompted the present inventors to follow up the 2×2 ANOVA with post hoc testing. Post-hoc comparisons revealed that, among home cage control animals, immunization with *M. vaccae* ATCC 15483 increased IL-4 protein in the dorsal hippocampus compared to BBS-treated animals ($p<0.05$; FIG. 28).

Example 21: Effects of Immunization with *M. vaccae* NCTC 11659 (NCTC) and Inescapable Tail Shock Stress (IS) on mRNA Expression of Immune Signaling Genes in the Liver The 2×2 ANOVA did not reveal an effect of treatment, stress, or a treatment x stress interaction on Il4 mRNA expression in the left lobe of the liver, although an effect of stress approached statistical significance ($F_{(1, 39)}=3.926$, $p=0.055$; FIG. 8C). Post hoc comparisons revealed that among rats immunized with *M. vaccae* NCTC 11659, IS increased Il4 gene expression ($p<0.05$; FIG. 29C).

The various features and processes described above may be used independently of one another or may be combined in various ways. All possible combinations and sub combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

TABLES

TABLE 1

Relative gene expression. Gene expression was run in duplicate and analyzed with the $2^{-\Delta\Delta Ct}$ method relative to β-actin.

| | Adult | | | | Aged | | | |
| | Vehicle | | M. vaccae | | Vehicle | | M. vaccae | |
| Group | Sham | Laparotomy | Sham | Laparotomy | Sham | Laparotomy | Sham | Laparotomy |
| Gene | Three days post-laparotomy (behaviorally naïve rats) | | | | | | | |
| Arg1 | 1.00 ± 0.08 | 1.06 ± 0.07 | 1.09 ± 0.08 | 1.16 ± 0.11 | 0.94 ± 0.07 | 0.9 ± 0.07 | 1.26 ± 0.07 | 1.26 ± 0.05 |
| CD200L | 1.00 ± 0.08 | 1.02 ± 0.07 | 0.98 ± 0.06 | 0.99 ± 0.11 | 0.82 ± 0.06 | 0.79 ± 0.05 | 0.94 ± 0.06 | 1.03 ± 0.12 |
| CD206 | 1.00 ± 0.09 | 0.81 ± 0.09 | 0.88 ± 0.15 | 0.94 ± 0.11 | 0.59 ± 0.04 | 0.49 ± 0.06 | 0.69 ± 0.04 | 0.75 ± 0.08 |
| CD-4 | 1.00 ± 0.07 | 0.85 ± 0.05 | 0.92 ± 0.07 | 0.82 ± 0.07 | 2.00 ± 0.14 | 1.80 ± 0.17 | 1.8 ± 0.14 | 1.80 ± 0.05 |
| IL-4 | 1.00 ± 0.10 | 0.93 ± 0.16 | 0.94 ± 0.15 | 0.88 ± 0.10 | 0.81 ± 0.07 | 0.56 ± 0.04 | 1.05 ± 0.17 | 1.10 ± 0.10 |
| IL-10 | 1.00 ± 0.17 | 0.79 ± 0.16 | 1.02 ± 0.19 | 0.96 ± 0.31 | 0.50 ± 0.15 | 0.43 ± 0.11 | 0.70 ± 0.13 | 0.62 ± 0.23 |
| IL-1β | 1.00 ± 0.12 | 0.90 ± 0.07 | 0.97 ± 0.08 | 0.83 ± 0.09 | 0.95 ± 0.08 | 1.44 ± 0.15 | 0.83 ± 0.13 | 0.84 ± 0.16 |
| Foxp3 | 1.00 ± 0.10 | 1.09 ± 0.10 | 1.18 ± 0.12 | 1.16 ± 0.09 | 1.14 ± 0.14 | 1.11 ± 0.09 | 1.52 ± 0.23 | 1.55 ± 0.19 |

TABLE 1-continued

Relative gene expression. Gene expression was run in duplicate and analyzed with the 2^ΔΔCt method relative to β-actin.

| | Adult | | | | Aged | | | |
| | Vehicle | | M. vaccae | | Vehicle | | M. vaccae | |
| Group | Sham | Laparotomy | Sham | Laparotomy | Sham | Laparotomy | Sham | Laparotomy |
|---|---|---|---|---|---|---|---|---|
| NFKBIA | 1.00 ± 0.08 | 1.10 ± 0.10 | 0.96 ± 0.07 | 1.05 ± 0.09 | 1.21 ± 0.06 | 1.62 ± 0.15 | 1.05 ± 0.07 | 1.28 ± 0.17 |
| MHCII | 1.00 ± 0.12 | 0.73 ± 0.08 | 0.95 ± 0.14 | 0.73 ± 0.07 | 4.41 ± 0.29 | 3.98 ± 0.48 | 2.94 ± 0.19 | 2.84 ± 0.37 |
| TGF-β | 1.00 ± 0.08 | 0.84 ± 0.06 | 0.94 ± 0.06 | 0.82 ± 0.14 | 1.04 ± 0.04 | 0.93 ± 0.06 | 0.89 ± 0.05 | 0.97 ± 0.05 |
| Eight days post-laparotomy (behavior rats) | | | | | | | | |
| Arg1 | 1.00 ± 0.06 | 0.81 ± 0.09 | 0.90 ± 0.11 | 0.80 ± 0.09 | 0.71 ± 0.08 | 0.69 ± 0.06 | 0.90 ± 0.07 | 1.07 ± 0.07 |
| IL-4 | 1.00 ± 0.17 | 1.02 ± 0.07 | 1.19 ± 0.14 | 1.06 ± 0.10 | 0.71 ± 0.09 | 0.61 ± 0.10 | 1.06 ± 0.11 | 1.04 ± 0.07 |
| IL-1β | 1.00 ± 0.14 | 1.19 ± 0.09 | 1.07 ± 0.08 | 1.10 ± 0.05 | 1.11 ± 0.14 | 0.95 ± 0.13 | 1.13 ± 0.14 | 0.87 ± 0.09 |

REFERENCES

1. Agusti, G., Astola, O., Rodriguez-Guell, E., Julian, E., Luquin, M., 2008. Surface spreading motility shown by a group of phylogenetically related, rapidly growing pigmented mycobacteria suggests that motility is a common property of mycobacterial species but is restricted to smooth colonies. J. Bacteriol. 190, 6894-6902.
2. Altschul, S. F., Madden, T. L., Schaffer, A. A., Zhang, J., Zhang, Z., Miller, W., Lipman, D. J., 1997. Gapped BLAST and PSI-BLAST: a new generation of protein database search programs. Nucleic Acids Res. 25, 3389-3402.
3. Ambarus, C. A., Krausz, S., van Eijk, M., Hamann, J., Radstake, T. R., Reedquist, K. A., Tak, P. P., Baeten, D. L., 2012. Systematic validation of specific phenotypic markers for in vitro polarized human macrophages. J. Immunol. Methods 375, 196-206.
4. Awad, F., Assrawi, E., Jumeau, C., Georgin-Lavialle, S., Cobret, L., Duquesnoy, P., Piterboth, W., Thomas, L., Stankovic-Stojanovic, K., Louvrier, C., Giurgea, I., Grateau, G., Amselem, S., Karabina, S. A., 2017. Impact of human monocyte and macrophage polarization on NLR expression and NLRP3 inflammasome activation. PLoS One 12, e0175336.
5. Bharwani, A., Mian, M. F., Surette, M. G., Bienenstock, J., Forsythe, P., 2017. Oral treatment with *Lactobacillus rhamnosus* attenuates behavioural deficits and immune changes in chronic social stress. BMC Med. 15, 7.
6. Bluthe, R. M., Lestage, J., Rees, G., Bristow, A., Dantzer, R., 2002. Dual effect of central injection of recombinant rat interleukin-4 on lipopolysaccharide-induced sickness behavior in rats. Neuropsychopharmacology 26, 86-93.
7. Bravo, J. A., Forsythe, P., Chew, M. V., Escaravage, E., Savignac, H. M., Dinan, T. G., Bienenstock, J., Cryan, J. F., 2011. Ingestion of *Lactobacillus* strain regulates emotional behavior and central GABA receptor expression in a mouse via the vagus nerve. Proc. Natl. Acad. Sci. U.S.A. 108, 16050-16055.
8. Cain, D. W., Cidlowski, J. A., 2017. Immune regulation by glucocorticoids. Nat. Rev. Immunol. 17, 233-247. Cheng, Y., Pardo, M., Armini, R. S., Martinez, A., Mouhsine, H., Zagury, J. F., Jope, R. S.,
9. Beurel, E., 2016. Stress-induced neuroinflammation is mediated by GSK3-dependent TLR4 signaling that promotes susceptibility to depression-like behavior. Brain Behav. Immun.
10. Chomczynski, P., Sacchi, N., 1987. Single-step method of RNA isolation by acid guanidinium thiocyanate-phenol-chloroform extraction. Anal. Biochem. 162, 156-159.
11. Christianson, J. P., Paul, E. D., Irani, M., Thompson, B. M., Kubala, K. H., Yirmiya, R., Watkins, L. R., Maier, S. F., 2008. The role of prior stressor controllability and the dorsal raphe nucleus in sucrose preference and social exploration. Behav. Brain Res. 193, 87-93.
12. Costello, D. A., Lyons, A., Denieffe, S., Browne, T. C., Cox, F. F., Lynch, M. A., 2011. Long term potentiation is impaired in membrane glycoprotein CD200-deficient mice: a role for Toll-like receptor activation. J. Biol. Chem. 286, 34722-34732.
13. de Pablos, R. M., Villaran, R. F., Arguelles, S., Herrera, A. J., Venero, J. L., Ayala, A., Cano, J., Machado, A., 2006. Stress increases vulnerability to inflammation in the rat prefrontal cortex. J. Neurosci. 26, 5709-5719.
14. Dean, O. M., Kanchanatawan, B., Ashton, M., Mohebbi, M., Ng, C. H., Maes, M., Berk, L., Sughondhabirom, A., Tangwongchai, S., Singh, A. B., McKenzie, H., Smith, D. J., Malhi, G. S., Dowling, N., Berk, M., 2017. Adjunctive minocycline treatment for major depressive disorder: a proof of concept trial. Aust. N. Z. J. Psychiatry 51, 829-840.
15. Denieffe, S., Kelly, R. J., McDonald, C., Lyons, A., Lynch, M. A., 2013. Classical activation of microglia in CD200-deficient mice is a consequence of blood brain barrier permeability and infiltration of peripheral cells. Brain Behav. Immun. 34, 86-97.
16. Derecki, N. C., Cardani, A. N., Yang, C. H., Quinnies, K. M., Crihfield, A., Lynch, K. R., Kipnis, J., 2010. Regulation of learning and memory by meningeal immunity: a key role for IL-4. J. Exp. Med. 207, 1067-1080.
17. Desbonnet, L., Garrett, L., Clarke, G., Kiely, B., Cryan, J. F., Dinan, T. G., 2010. Effects of the probiotic *Bifidobacterium infantis* in the maternal separation model of depression. Neuroscience 170, 1179-1188.
18. DuPont, R. L., Rice, D. P., Miller, L. S., Shiraki, S. S., Rowland, C. R., Harwood, H. J., 1996. Economic costs of anxiety disorders. Anxiety 2, 167-172.
19. Edwards, J. P., Zhang, X., Frauwirth, K. A., Mosser, D. M., 2006. Biochemical and functional characterization of three activated macrophage populations. J. Leukoc. Biol. 80, 1298-1307.
20. Eraly, S. A., Nievergelt, C. M., Maihofer, A. X., Barkauskas, D. A., Biswas, N., Agorastos, A., O'Cconnor, D. T., Baker, D. G., Marine Resiliency Study, T., 2014. Assessment of plasma C-reactive protein as a biomarker of posttraumatic stress disorder risk. JAMA Psychiatry 71, 423-431.
21. Espinosa-Oliva, A. M., de Pablos, R. M., Villaran, R. F., Arguelles, S., Venero, J. L., Machado, A., Cano, J., 2011.

Stress is critical for LPS-induced activation of microglia and damage in the rat hippocampus. Neurobiol. Aging 32, 85-102.
22. Fanselow, M. S., Dong, H. W., 2010. Are the dorsal and ventral hippocampus functionally distinct structures? Neuron 65, 7-19.
23. M. G. Frank et al. *Brain, Behavior, and Immunity* 73 (2018) 352-363
24. File, S. E., Seth, P., 2003. A review of 25 years of the social interaction test. Eur. J. Pharmacol. 463, 35-53.
25. Frank, M. G., Wieseler-Frank, J. L., Watkins, L. R., Maier, S. F., 2006. Rapid isolation of highly enriched and quiescent microglia from adult rat hippocampus: immunophenotypic and functional characteristics. J. Neurosci. Methods 151, 121-130.
26. Frank, M. G., Baratta, M. V., Sprunger, D. B., Watkins, L. R., Maier, S. F., 2007. Microglia serve as a neuroimmune substrate for stress-induced potentiation of CNS pro-inflammatory cytokine responses. Brain Behav. Immun. 21, 47-59.
27. Frank, M. G., Barrientos, R. M., Thompson, B. M., Weber, M. D., Watkins, L. R., Maier, S. F., 2012a. IL-1RA injected intra-cisterna magna confers extended prophylaxis against lipopolysaccharide-induced neuroinflammatory and sickness responses. J. Neuroimmun. 252, 33-39.
28. Frank, M. G., Thompson, B. M., Watkins, L. R., Maier, S. F., 2012b. Glucocorticoids mediate stress-induced priming of microglial pro-inflammatory responses. Brain Behav. Immun. 26, 337-345.
29. Frank, M. G., Weber, M. D., Fonken, L. K., Hershman, S. A., Watkins, L. R., Maier, S. F., 2015a. The redox state of the alarmin HMGB1 is a pivotal factor in neuroinflammatory and microglial priming: a role for the NLRP3 inflammasome. Brain Behav. Immun. 55, 215-224.
30. Frank, M. G., Weber, M. D., Watkins, L. R., Maier, S. F., 2015b. Stress sounds the alarmin: the role of the danger-associated molecular pattern HMGB1 in stress-induced neuroinflammatory priming. Brain Behav. Immun. 48, 1-7.
31. Frank, M. G., Weber, M. D., Watkins, L. R., Maier, S. F., 2016. Stress-induced neuroinflammatory priming: a liability factor in the etiology of psychiatric disorders. Neurobiol. Stress 4, 62-70.
32. Frank, M. G., Fonken, L. K., Annis, J. L., Watkins, L. R., Maier, S. F., 2018. Stress disinhibits microglia via downregulation of CD200R: a mechanism of neuroinflammatory priming. Brain Behav. Immun. 69, 62-73.
33. Gadani, S. P., Cronk, J. C., Norris, G. T., Kipnis, J., 2012. IL-4 in the brain: a cytokine to remember. J. Immunol. 189, 4213-4219.
34. Gorczynski, R. M., 2005. CD200 and its receptors as targets for immunoregulation. Curr. Opin. Invest. Drugs 6, 483-488.
35. Goshen, I., Yirmiya, R., 2009. Interleukin-1 (IL-1): a central regulator of stress responses. Front. Neuroendocrinol. 30, 30-45.
36. Greenberg, P. E., Sisitsky, T., Kessler, R. C., Finkelstein, S. N., Berndt, E. R., Davidson, J. R., Ballenger, J. C., Fyer, A. J., 1999. The economic burden of anxiety disorders in the 1990s. J. Clin. Psychiatry 60, 427-435.
37. Hernangomez, M., Klusakova, I., Joukal, M., Hradilova-Svizenska, I., Guaza, C., Dubovy, P., 2016. CD200R1 agonist attenuates glial activation, inflammatory reactions, and hypersensitivity immediately after its intrathecal application in a rat neuropathic pain model. J Neuroinflammation 13, 43.
38. Hoarau, J. J., Krejbich-Trotot, P., Jaffar-Bandjee, M. C., Das, T., Thon-Hon, G. V., Kumar, S., Neal, J. W., Gasque, P., 2011. Activation and control of CNS innate immune responses in health and diseases: a balancing act finely tuned by neuroimmune regulators (NIReg). CNS Neurol. Disorders Drug Targets 10, 25-43.
39. Hodes, G. E., Pfau, M. L., Leboeuf, M., Golden, S. A., Christoffel, D. J., Bregman, D., Rebusi, N., Heshmati, M., Aleyasin, H., Warren, B. L., Lebonte, B., Horn, S., Lapidus, K. A., Stelzhammer, V., Wong, E. H., Bahn, S., Krishnan, V., Bolanos-Guzman, C. A., Murrough, J. W., Merad, M., Russo, S. J., 2014. Individual differences in the peripheral immune system promote resilience versus susceptibility to social stress. Proc. Natl. Acad. Sci. U.S.A. 111, 16136-16141.
40. Hoisington, A. J., Brenner, L. A., Kinney, K. A., Postolache, T. T., Lowry, C. A., 2015. The microbiome of the built environment and mental health. Microbiome 3, 60. Holt, W., Maren, S., 1999. Muscimol inactivation of the dorsal hippocampus impairs contextual retrieval of fear memory. J. Neurosci. 19, 9054-9062.
41. Janak, P. H., Tye, K. M., 2015. From circuits to behaviour in the amygdala. Nature 517, 284-292.
42. Johnson, J. D., O'Connor, K. A., Hansen, M. K., Watkins, L. R., Maier, S. F., 2003. Effects of prior stress on LPS-induced cytokine and sickness responses. Am. J. Physiol. Regul. Integr. Comp. Physiol. 284, R422-432.
43. Johnson, J. D., O'Connor, K. A., Watkins, L. R., Maier, S. F., 2004. The role of IL-1beta in stress-induced sensitization of proinflammatory cytokine and corticosterone responses. Neuroscience 127, 569-577.
44. Johnson, J. D., Campisi, J., Sharkey, C. M., Kennedy, S. L., Nickerson, M., Greenwood, B. N., Fleshner, M., 2005. Catecholamines mediate stress-induced increases in peripheral and central inflammatory cytokines. Neuroscience 135, 1295-1307.
45. Kessler, R. C., Greenberg, P. E., 2002. The economic burden of anxiety and stress disorders. Neuropsychopharmacology—5th Generation of Progress., pp. 981-992.
46. Khandaker, G. M., Pearson, R. M., Zammit, S., Lewis, G., Jones, P. B., 2014. Association of serum interleukin 6 and C-reactive protein in childhood with depression and psychosis in young adult life: a population-based longitudinal study. JAMA Psychiatry 71, 1121-1128.
47. Kim, J. J., Fanselow, M. S., 1992. Modality-specific retrograde amnesia of fear. Science 256, 675-677.
48. Kivimaki, M., Shipley, M. J., Batty, G. D., Hamer, M., Akbaraly, T. N., Kumari, M., Jokela, M., Virtanen, M., Lowe, G. D., Ebmeier, K. P., Brunner, E. J., Singh-Manoux, A., 2014. Long-term inflammation increases risk of common mental disorder: a cohort study. Mol. Psychiatry 19, 149-150.
49. Kjelstrup, K. G., Tuvnes, F. A., Steffenach, H. A., Murison, R., Moser, E. I., Moser, M. B., 2002. Reduced fear expression after lesions of the ventral hippocampus. Proc. Natl. Acad. Sci. U.S.A. 99, 10825-10830.
50. Kohler, O., Benros, M. E., Nordentoft, M., Farkouh, M. E., Iyengar, R. L., Mors, O., Krogh, J., 2014. Effect of anti-inflammatory treatment on depression, depressive symptoms, and adverse effects: a systematic review and meta-analysis of randomized clinical trials. JAMA Psychiatry 71, 1381-1391.
51. Koning, N., Swaab, D. F., Hoek, R. M., Huitinga, I., 2009. Distribution of the immune inhibitory molecules CD200 and CD200R in the normal central nervous system and multiple sclerosis lesions suggests neuron-glia and glia-glia interactions. J. Neuropathol. Exp. Neurol. 68, 159-167.
52. Lee, A. R., Kim, J. H., Cho, E., Kim, M., Park, M., 2017. Dorsal and ventral hippocampus differentiate in functional pathways and differentially associate with neurological disease-related genes during postnatal development. Front. Mol. Neurosci. 10, 331.
53. Leemans, J. C., Cassel, S. L., Sutterwala, F. S., 2011. Sensing damage by the NLRP3 inflammasome. Immunol. Rev. 243, 152-162.
54. Li, Y., Xiao, B., Qiu, W., Yang, L., Hu, B., Tian, X., Yang, H., 2010. Altered expression of CD4(+)CD25(+) regulatory T cells and its 5-HT(1a) receptor in patients with major depression disorder. J. Affect. Disord. 124, 68-75.
55. Lian, Y. J., Gong, H., Wu, T. Y., Su, W. J., Zhang, Y., Yang, Y. Y., Peng, W., Zhang, T., Zhou, J. R., Jiang, C. L., Wang, Y. X., 2017. Ds-HMGB1 and fr-HMGB induce depressive behavior through neuroinflammation in contrast to nonoxid-HMGB1. Brain Behav. Immun. 59, 322-332.
56. Liang, S., Wang, T., Hu, X., Luo, J., Li, W., Wu, X., Duan, Y., Jin, F., 2015. Administration of *Lactobacillus helveticus* NS8 improves behavioral, cognitive, and biochemical aberrations caused by chronic restraint stress. Neuroscience 310, 561-577.
57. Lowry, C. A., Smith, D. G., Siebler, P. H., Schmidt, D., Stamper, C. E., Hassell Jr., J. E., Yamashita, P. S., Fox, J. H., Reber, S. O., Brenner, L. A., Hoisington, A. J., Postolache, T. T., Kinney, K. A., Marciani, D., Hernandez, M., Hemmings, S. M., Malan-Muller, S., Wright, K. P., Knight, R., Raison, C. L., Rook, G. A., 2016. The microbiota, immunoregulation, and mental health: implications for public health. Curr. Environ. Health Rep. 3, 270-286.
58. Lyons, A., Downer, E. J., Crotty, S., Nolan, Y. M., Mills, K. H., Lynch, M. A., 2007. CD200 ligand receptor interaction modulates microglial activation in vivo and in vitro: a role for IL-4. J. Neurosci. 27, 8309-8313.
59. Maier, S. F., Watkins, L. R., 1995. Intracerebroventricular interleukin-1 receptor antagonist blocks the enhancement of fear conditioning and interference with escape produced by inescapable shock. Brain Res. 695, 279-282.
60. Maren, S., Fanselow, M. S., 1995. Synaptic plasticity in the basolateral amygdala induced by hippocampal formation stimulation in vivo. J. Neurosci. 15, 7548-7564.
61. Marin, I. A., Goertz, J. E., Ren, T., Rich, S. S., Onengut-Gumuscu, S., Farber, E., Wu, M., Overall, C. C., Kipnis, J., Gaultier, A., 2017. Microbiota alteration is associated with the development of stress-induced despair behavior. Sci. Rep. 7, 43859.
62. Miller, A. H., Raison, C. L., 2016. The role of inflammation in depression: from evolutionary imperative to modern treatment target. Nat. Rev. Immunol. 16, 22-34.
63. Mosser, D. M., Edwards, J. P., 2008. Exploring the full spectrum of macrophage activation. Nat. Rev. Immunol. 8, 958-969.
64. Munhoz, C. D., Lepsch, L. B., Kawamoto, E. M., Malta, M. B., Lima Lde, S., Avellar, M. C., Sapolsky, R. M., Scavone, C., 2006. Chronic unpredictable stress exacerbates lipopolysaccharide-induced activation of nuclear factor-kappaB in the frontal cortex and hippocampus via glucocorticoid secretion. J. Neurosci. 26, 3813-3820.
65. Niebuhr, M., Baumert, K., Heratizadeh, A., Satzger, I., Werfel, T., 2014. Impaired NLRP3 inflammasome expression and function in atopic dermatitis due to Th2 milieu. Allergy 69, 1058-1067.
66. Pervanidou, P., Kolaitis, G., Charitaki, S., Margeli, A., Ferentinos, S., Bakoula, C., Lazaropoulou, C., Papassotiriou, I., Tsiantis, J., Chrousos, G. P., 2007. Elevated morning serum interleukin (IL)-6 or evening salivary cortisol concentrations predict posttraumatic stress disorder in children and adolescents six months after a motor vehicle accident. Psychoneuroendocrinology 32, 991-999.
67. Raison, C. L., Rutherford, R. E., Woolwine, B. J., Shuo, C., Schettler, P., Drake, D. F., Haroon, E., Miller, A. H., 2013. A randomized controlled trial of the tumor necrosis factor antagonist infliximab for treatment-resistant depression: the role of baseline inflammatory biomarkers. JAMA Psychiatry 70, 31-41.
68. Ransohoff, R. M., Cardona, A. E., 2010. The myeloid cells of the central nervous system parenchyma. Nature 468, 253-262.
69. Ransohoff, R. M., Perry, V. H., 2009. Microglial physiology: unique stimuli, specialized responses. Annu. Rev. Immunol. 27, 119-145.
70. Reber, S. O., Langgartner, D., Foertsch, S., Postolache, T. T., Brenner, L. A., Guendel, H., Lowry, C. A., 2016a. Chronic subordinate colony housing paradigm: a mouse model for mechanisms of PTSD vulnerability, targeted prevention, and treatment-2016 Curt Richter Award Paper. Psychoneuroendocrinology 74, 221-230.
71. Reber, S. O., Siebler, P. H., Donner, N. C., Morton, J. T., Smith, D. G., Kopelman, J. M., Lowe, K. R., Wheeler, K. J., Fox, J. H., Hassell Jr., J. E., Greenwood, B. N., Jansch, C., Lechner, A., Schmidt, D., Uschold-Schmidt, N., Fuchsl, A. M., Langgartner, D., Walker, F. R., Hale, M. W., Lopez Perez, G., Van Treuren, W., Gonzalez, A., Halweg-Edwards, A. L., Fleshner, M., Raison, C. L., Rook, G. A., Peddada, S. D., Knight, R., Lowry, C. A., 2016b. Immunization with a heat-killed preparation of the environmental bacterium *Mycobacterium vaccae* promotes stress resilience in mice. Proc. Natl. Acad. Sci. U.S.A. 113, E3130-3139.
72. Rohleder, N., 2014. Stimulation of systemic low-grade inflammation by psychosocial stress. Psychosom. Med. 76, 181-189. Rook, G. A., 2013. Regulation of the immune system by biodiversity from the natural environment: an ecosystem service essential to health. Proc. Natl. Acad. Sci. U.S.A. 110, 18360-18367.
73. Rook, G. A., Adams, V., Hunt, J., Palmer, R., Martinelli, R., Brunet, L. R., 2004. Mycobacteria and other environmental organisms as immunomodulators for immunoregulatory disorders. Springer Semin. Immunopathol. 25, 237-255.
74. Rook, G. A., Lowry, C. A., 2008. The hygiene hypothesis and psychiatric disorders. Trends Immunol. 29, 150-158. Rook, G. A., Raison, C. L., Lowry, C. A., 2013. Childhood microbial experience, immunoregulation, inflammation and adult susceptibility to psychosocial stressors and depression in rich and poor countries. Evol. Med. Publ. Health 2013, 14-17.
75. Rook, G. A., Raison, C. L., Lowry, C. A., 2014. Microbiota, immunoregulatory old friends and psychiatric disorders. Adv. Exp. Med. Biol. 817, 319-356.
76. Rook, G. A., Lowry, C. A., Raison, C. L., 2015. Hygiene and other early childhood influences on the subsequent function of the immune system. Brain Res. 1617, 47-62.
77. Sagar, D., Foss, C., El Baz, R., Pomper, M. G., Khan, Z. K., Jain, P., 2012. Mechanisms of dendritic cell trafficking across the blood-brain barrier. J. Neuroimmune Pharmacol. 7, 74-94.

78. Sarkar, A., Lehto, S. M., Harty, S., Dinan, T. G., Cryan, J. F., Burnet, P. W., 2016. Psychobiotics and the manipulation of bacteria-gut-brain signals. Trends Neurosci. 39, 763-781.
79. Sommershof, A., Aichinger, H., Engler, H., Adenauer, H., Catani, C., Boneberg, E. M., Elbert, T., Groettrup, M., Kolassa, I. T., 2009. Substantial reduction of naive and regulatory T cells following traumatic stress. Brain Behav. Immun. 23, 1117-1124.
80. Sorrells, S. F., Caso, J. R., Munhoz, C. D., Sapolsky, R. M., 2009. The stressed CNS: when glucocorticoids aggravate inflammation. Neuron 64, 33-39.
81. Vecchiarelli, H. A., Gandhi, C. P., Gray, J. M., Morena, M., Hassan, K. I., Hill, M. N., 2016. Divergent responses of inflammatory mediators within the amygdala and medial prefrontal cortex to acute psychological stress. Brain Behav. Immun. 51, 70-91.
82. von Hertzen, L., Beutler, B., Bienenstock, J., Blaser, M., Cani, P. D., Eriksson, J., Farkkila, M., Haahtela, T., Hanski, I., Jenmalm, M. C., Kere, J., Knip, M., Kontula, K., Koskenvuo, M., Ling, C., Mandrup-Poulsen, T., von Mutius, E., Makela, M. J., Paunio, T., Pershagen, G., Renz, H., Rook, G., Saarela, M., Vaarala, O., Veldhoen, M., de Vos, W. M., 2015. Helsinki alert of biodiversity and health. Ann. Med. 47, 218-225.
83. Wachholz, S., Knorr, A., Mengert, L., Plumper, J., Sommer, R., Juckel, G., Friebe, A., 2017. Interleukin-4 is a participant in the regulation of depressive-like behavior. Behav. Brain Res. 326, 165-172.
84. Walker, D. G., Dalsing-Hernandez, J. E., Campbell, N. A., Lue, L. F., 2009. Decreased expression of CD200 and CD200 receptor in Alzheimer's disease: a potential mechanism leading to chronic inflammation. Exp. Neurol. 215, 5-19.
85. Walsh, J. T., Watson, N., Kipnis, J., 2014. T cells in the central nervous system: messengers of destruction or purveyors of protection? Immunology 141, 340-344.
86. Weber, M. D., Frank, M. G., Tracey, K. J., Watkins, L. R., Maier, S. F., 2015. Stress induces the danger-associated molecular pattern HMGB-1 in the hippocampus of male sprague dawley rats: a priming stimulus of microglia and the NLRP3 inflammasome. J. Neurosci. 35, 316-324.
87. Wohleb, E. S., Hanke, M. L., Corona, A. W., Powell, N. D., Stiner, L. M., Bailey, M. T., Nelson, R. J., Godbout, J. P., Sheridan, J. F., 2011. beta-Adrenergic receptor antagonism prevents anxiety-like behavior and microglial reactivity induced by repeated social defeat. J. Neurosci. 31, 6277-6288.
88. Wright, G. J., Puklavec, M. J., Willis, A. C., Hoek, R. M., Sedgwick, J. D., Brown, M. H., Barclay, A. N., 2000. Lymphoid/neuronal cell surface OX2 glycoprotein recognizes a novel receptor on macrophages implicated in the control of their function. Immunity 13, 233-242.
89. Yang, Han Z., Oppenheim, J. J., 2017. Alarmins and immunity. Immunol. Rev. 280, 41-56.
90. Zuany-Amorim, C., Sawicka, E., Manlius, C., Le Moine, A., Brunet, L. R., Kemeny, D. M., Bowen, G., Rook, G., Walker, C., 2002. Suppression of airway eosinophilia by killed *Mycobacterium vaccae*-induced allergen-specific regulatory T-cells. Nat. Med. 8, 625-629.

What is claimed is:

1. A method of inhibiting postoperative cognitive dysfunction (POCD) comprising administering a therapeutically effective amount of an isolated *Mycobacterium vaccae* to a mammalian subject before or after administering a surgical anesthetic to the subject.

2. The method of claim 1, wherein the *M. vaccae* is whole cell *M. vaccae*.

3. The method of claim 1, wherein the *M. vaccae* is non-pathogenic heat-killed *M. vaccae*.

4. The method of claim 1, wherein the *M. vaccae* is strain NCTC 11659.

5. The method of claim 1, wherein the *M. vaccae* is in the form of a vaccine composition, optionally comprising an adjuvant.

6. The method of claim 1, wherein the *M. vaccae* is formulated for administration via the parenteral, oral, sublingual, nasal, or pulmonary route.

7. The method of claim 1, wherein the method ameliorates at least one sign or symptom of POCD wherein the sign or symptom is selected from brain death, stroke, neuropsychological impairment comprising a decline in one or more of neuropsychological domains including memory, executive functioning, and speed processing.

8. A method of treating or ameliorating the incidence of postoperative cognitive dysfunction (POCD) in a mammalian patient comprising administering a therapeutically effective amount of an isolated *M. vaccae* to the subject.

9. The method of claim 8, wherein the *M. vaccae* is whole cell *M. vaccae*.

10. The method of claim 8, wherein the *M. vaccae* is a non-pathogenic heat-killed *M. vaccae*.

11. The method of claim 8, wherein the *M. vaccae* is strain NCTC 11659.

12. The method of claim 8, wherein the *M. vaccae* is in the form of a vaccine composition optionally comprising an adjuvant.

13. The method of claim 8, wherein the *M. vaccae* is formulated for administration via the parenteral, oral, sublingual, nasal, or pulmonary route.

14. The method of claim 8, wherein the method ameliorates at least one sign or symptom of POCD wherein the sign or symptom is selected from brain death, stroke, neuropsychological impairment comprising a decline in one or more of neuropsychological domains including memory, executive functioning, and speed processing.

* * * * *